(12) United States Patent
Lucchino et al.

(10) Patent No.: US 9,694,114 B2
(45) Date of Patent: Jul. 4, 2017

(54) ANTIMICROBIAL CATHETERS WITH PERMEABILIZATION AGENTS

(71) Applicant: SEMPRUS BIOSCIENCES CORP, Cambridge, MA (US)

(72) Inventors: David Lucchino, Charlestown, MA (US); Christopher R. Loose, Cambridge, MA (US)

(73) Assignee: ARROW INTERNATIONAL, INC., Wayne, PA (US)

( * ) Notice: Subject to any disclaimer, the term of this patent is extended or adjusted under 35 U.S.C. 154(b) by 0 days.

(21) Appl. No.: 14/910,473

(22) PCT Filed: Aug. 6, 2014

(86) PCT No.: PCT/US2014/049896
§ 371 (c)(1),
(2) Date: Feb. 5, 2016

(87) PCT Pub. No.: WO2015/021123
PCT Pub. Date: Feb. 12, 2015

(65) Prior Publication Data
US 2016/0235893 A1     Aug. 18, 2016

Related U.S. Application Data

(60) Provisional application No. 61/863,065, filed on Aug. 7, 2013, provisional application No. 61/869,482, filed on Aug. 23, 2013.

(51) Int. Cl.
*A61L 29/16* (2006.01)
*A61L 29/08* (2006.01)
*A61L 29/14* (2006.01)
*A61L 29/18* (2006.01)
*A61L 29/02* (2006.01)
*A61M 25/00* (2006.01)
*A61L 29/00* (2006.01)
*A61K 31/155* (2006.01)
*A61K 36/61* (2006.01)

(52) U.S. Cl.
CPC ............ *A61L 29/16* (2013.01); *A61K 31/155* (2013.01); *A61K 36/61* (2013.01); *A61L 29/005* (2013.01); *A61L 29/02* (2013.01); *A61L 29/085* (2013.01); *A61L 29/14* (2013.01); *A61L 29/18* (2013.01); *A61M 25/0045* (2013.01); *A61L 2300/202* (2013.01); *A61L 2300/206* (2013.01); *A61L 2300/30* (2013.01); *A61L 2300/404* (2013.01)

(58) Field of Classification Search
CPC ........ A61L 29/16; A61L 29/18; A61L 29/085; A61L 29/02; A61L 2300/206; A61L 2300/404; A61M 25/0045
See application file for complete search history.

(56) References Cited

U.S. PATENT DOCUMENTS

2012/0201902 A1     8/2012  Modak et al.
2013/0158517 A1     6/2013  Bouchard et al.

*Primary Examiner* — Michael C Miggins
(74) *Attorney, Agent, or Firm* — Baker & Hostetler LLP

(57) ABSTRACT

Catheters and a method of preparation thereof comprising a catheter body and at least one connector. The catheter body has an exterior surface and at least one lumen having an aspect ratio of at least 3:1 and an intraluminal surface comprising a hydrophilic polymer layer thereon, the hydrophilic polymer layer has an average dry thickness of at least about 50 nanometers, wherein the catheter body comprises one or more permeabilization agents and one or more antimicrobial agents.

23 Claims, 4 Drawing Sheets

ANTIMICROBIAL CATHETERS WITH PERMEABILIZATION AGENTS

CROSS-REFERENCE TO RELATED APPLICATIONS

This application is a National Stage of International patent application PCT/US2014/049896, filed on Aug. 6, 2014, which claims priority to U.S. Provisional Patent Application No. 61/863,065 filed Aug. 7, 2013 and U.S. Provisional Patent Application No. 61/869,482 filed Aug. 23, 2013, the disclosures of which are incorporated herein by reference in their entirety.

FIELD OF THE INVENTION

The present invention generally relates to catheters and more particularly to catheters used for introduction and removal of fluids from a human body.

BACKGROUND OF THE INVENTION

Catheters are commonplace in the medical field, finding importance in a variety of uses. Catheters, for example, come in many different forms and have many different uses including Venous, Arterial, Cardiac, Urinary, Biliary, Epidural, Cerebral, Guiding, Pleural, Peritoneal, Ophthalmic, Drainage, Gastrointestinal, Neurovascular, Nasogastric. The primary types of vascular catheters include the short peripheral, which is typically placed only a short distance (e.g., 5-7.5 cm) in a vein or artery in the hand or arm of the patient, venous catheters that are longer and include a midline catheter that is placed approximately 15-20 cm in the vein of a patient, and central venous catheters.

Central venous catheters ("CVC") are typically used to administer medications, blood products, or other fluids and there are several types. Non-tunneled central venous catheters are commonly used for administration of therapeutics and fluids in critical care patients and are fixed in place at the site of insertion, with the catheter and attachments protruding directly. Tunneled catheters are passed under the skin from the insertion site to a separate exit site, where the catheter and its attachments emerge from the skin; a hemodialysis catheter is a commonly used type of tunneled central venous catheter. A peripherally inserted central catheter ("PICC") is commonly used for acute and chronic care patients and is inserted peripherally, e.g., in the arm of a patient rather than in the neck, chest or groin, and fed a significant distance, e.g., to the superior vena cava. Central venous catheters provide necessary vascular access but they are associated with two common complications; infection and thrombotic occlusion.

The pathogenesis of most catheter-related bloodstream infections associated with the use of long-term catheters (>10 days) involve microbial contamination of the catheter lumen(s), followed by formation of a microbial biofilm and subsequent seeding of the blood with microbial cells. Approximately 80,000 catheter-related blood stream infections occur in intensive care units each year (Mermel, *Ann. Intern. Med.* 132:391-402 (2000)) with an estimated 250,000 cases of blood stream infections occurring if entire hospitals are reviewed (Maki et al., *Mayo Clin. Proc.* 81:1159-71 (2006)). Catheter-related blood stream infections increase the cost of patient care by extending the length of stay of a patient.

Catheter occlusion is the most common non-infectious complication in long-term use of central venous catheters (Andris, 1999; Calis, Herbst, & Sidawy, 1999). Thrombotic occlusions, which include the development of a thrombus within and/or around the catheter or surrounding vessel (Haire & Herbst, 2000; Herbst & McKinnon, 2001), increase the cost of patient care by the interruption and extending the time of therapy, possible infiltration or extravasation of infusate, or as a nidus of infection. The incidence of thrombotic occlusion in central venous catheters ranges from 3% to 79% of inserted catheters (Moureau, Poole, Murdock, Gray, & Semba, 2002; Walshe, Malak, Eagan, & Sepkowitz, 2002; Wingerter, 2003).

Various methods have been proposed to prepare catheters with surfaces that express antimicrobial and/or antithrombogenic activity. Such methods include dip or spray coating of polymer/drug mixtures, drug impregnation, plasma coating, covalently bonded drugs, drug-polymer conjugates, and direct incorporation of the antimicrobial or antithrombogenic agents into the polymeric matrix of the catheter. Each of these methods present challenges with respect to catheter lumen surfaces such as one or more of the following: non-uniform coating thickness, inaccessible lumens, lumen blockage/restriction, require that only high heat tolerant agents can be used, and/or the limited duration of activity of drug reservoir-based systems.

A vascular catheter typically consists of a hub and tubing or cannula through which fluid flows. Dependent on the type of catheter and its intended use, the number of tubes or cannula (lumen) through which fluid flows may range from one (monoluminal) to five or more; the more common are monoluminal, biluminal, or triluminal (1, 2 and 3 respectively). Typically, the different component parts (e.g., the hubs and tubing) are formed from different polymers. This presents challenges to create a single surface modification with similar properties across at least two catheter components.

There exists a need for techniques and catheters that can be effective at reducing microbial contamination/biofilm and thrombus attachment and accumulation on a catheter. Further a need exists in which one or more permeabilization agents are in the catheter formulation that enhance the penetration of release antimicrobial agents into surrounding tissue. Increased antimicrobial penetration may enhance the ability of the catheter to reduce tissue colonization near the device.

SUMMARY OF THE INVENTION

Among the various aspects of the present invention is the provision of catheters comprising a polymeric material on the exterior and/or intraluminal surfaces thereof that can be effective at reducing microbial attachment, biofilm formation, platelet attachment or thrombus formation.

Briefly, therefore, the present invention is directed to a catheter comprising as component parts thereof a catheter body and at least one connector. The catheter body has an exterior surface and at least one lumen having an aspect ratio of at least 250:1 and an intraluminal surface comprising a hydrophilic polymer layer thereon. The hydrophilic polymer layer has an average dry thickness of at least about 50 nanometers.

The present invention is further directed to a catheter comprising as component parts thereof a catheter body and at least one connector, the catheter body having an exterior surface and at least one lumen having an aspect ratio of at least 3:1 and an intraluminal surface comprising a hydrophilic polymer layer thereon. The hydrophilic polymer layer has an average dry thickness of at least about 200 nanometers.

The present invention is further directed to a catheter comprising as component parts thereof a catheter body and at least one connector, the catheter body having an exterior surface and at least one lumen having an aspect ratio of at least 3:1 and an intraluminal surface comprising a hydrophilic polymer layer thereon. The hydrophilic polymer layer having an Average Dry Thickness of at least about 50 nanometers and comprises repeat units, at least 30% of which are derived from a hydrophilic monomer.

The present invention is further directed to a catheter comprising as component parts thereof a catheter body and at least one connector. The catheter body has an exterior surface and at least one lumen having an aspect ratio of at least 3:1 and an intraluminal surface comprising a hydrophilic polymer layer thereon. The hydrophilic polymer layer has an average dry thickness of at least about 50 nanometers and a standard deviation of the average dry thickness that does not exceed 100% of the average dry thickness of the hydrophilic polymer layer.

The present invention is further directed to a catheter comprising as component parts thereof a catheter body and at least one connector. The catheter body has an exterior surface and at least one lumen having an aspect ratio of at least 3:1 and an intraluminal surface comprising a hydrophilic polymer layer thereon. The hydrophilic polymer layer has an average dry thickness of at least about 50 nanometers and is conformal at a level of 1 mm$^2$.

The present invention is further directed to a catheter comprising as component parts thereof a catheter body and at least one connector. The catheter body has an exterior surface and at least one lumen having an aspect ratio of at least 3:1 and an intraluminal surface having a global average $R_{rms}$ surface roughness and comprising a hydrophilic polymer layer thereon. The hydrophilic polymer layer has an average dry thickness that exceeds the global average $R_{rms}$ surface roughness of the intraluminal surface and is at least about 50 nm.

The present invention is further directed to a catheter comprising as component parts thereof a catheter body and at least one connector. The catheter body has an exterior surface and at least one lumen having an aspect ratio of at least 3:1 and an intraluminal surface having a global average $R_{rms}$ surface roughness and comprising a hydrophilic polymer layer thereon having a thickness of at least about 50 nm. The intraluminal surface and the hydrophilic polymer layer, in combination, constitute a modified surface having a global average $R_{rms}$ surface roughness that is less than the global average $R_{rms}$ surface roughness of the substrate surface.

The present invention is further directed to a catheter comprising as component parts thereof a catheter body and at least one connector. The catheter body has an exterior surface and at least one lumen having an aspect ratio of at least 3:1 and an intraluminal surface comprising a hydrophilic polymer layer thereon having a thickness of at least about 50 nm. The intraluminal surface and the hydrophilic polymer layer, in combination, constitute a modified surface having a fibrinogen adsorption of less than about 125 ng/cm$^2$ in a fibrinogen binding assay in which the modified surface is incubated for 60 minutes at 37° C. in a composition containing 70 µg/ml fibrinogen derived from human plasma and 1.4 µg/ml 1-125 radiolabeled fibrinogen.

The present invention is further directed to a multilumen catheter comprising a catheter body, a juncture hub, extension lines and connectors, the catheter body having a proximal end, a distal end, an exterior surface, a tip region having a length of 10 cm measured from the distal end of the catheter body, and at least two lumen. Each of the catheter body lumen have a proximal end, a distal end, a Lumen Aspect Ratio of at least 3:1, and an intraluminal surface. The distal ends of the at least two catheter body lumen are (i) non-coterminus or (ii) laser-cut. Additionally, the exterior surface of the catheter body in the tip region and the intraluminal surface of the two catheter body lumen comprise a hydrophilic polymer layer having an Average Dry Thickness of at least about 50 nanometers.

The present invention is further directed to a catheter comprising as component parts thereof a catheter body, a juncture hub, at least one extension line and at least one connector, each of said component parts comprising an exterior surface, at least one lumen having an intraluminal surface and a bulk polymer. The intraluminal or external surface of a first of said component parts and the exterior or intraluminal surface of a second of said component parts comprise a hydrophilic polymer layer thereon having an Average Dry Thickness of at least about 50 nanometers. The first and second component parts further comprise bulk polymers having different chemical compositions.

The present invention is further directed to a process for modifying the intraluminal surface of a lumen of a catheter body, the catheter comprising as component parts thereof the catheter body and at least one connector, the catheter body having an exterior surface and at least one lumen having an intraluminal surface and a Lumen Aspect Ratio of at least 3:1 (lumen length:lumen diameter). The process comprises forming a reaction mixture comprising monomer, a free radical initiator and a solvent system, charging the reaction mixture into said catheter body lumen and polymerizing the monomer in the reaction mixture to graft a polymer from the intraluminal surface of said lumen, the reaction mixture having a viscosity of less than 30 cP during polymerization and continuously or intermittently replacing the reaction mixture charged into said catheter body lumen until the grafted polymer layer has an Average Dry Thickness that exceeds at least about 50 nanometers.

Other objects and features will be in part apparent and in part pointed out hereinafter.

BRIEF DESCRIPTION OF THE DRAWINGS

Corresponding reference characters indicate corresponding parts throughout the drawings.

ABBREVIATIONS AND DEFINITIONS

Figure 1:
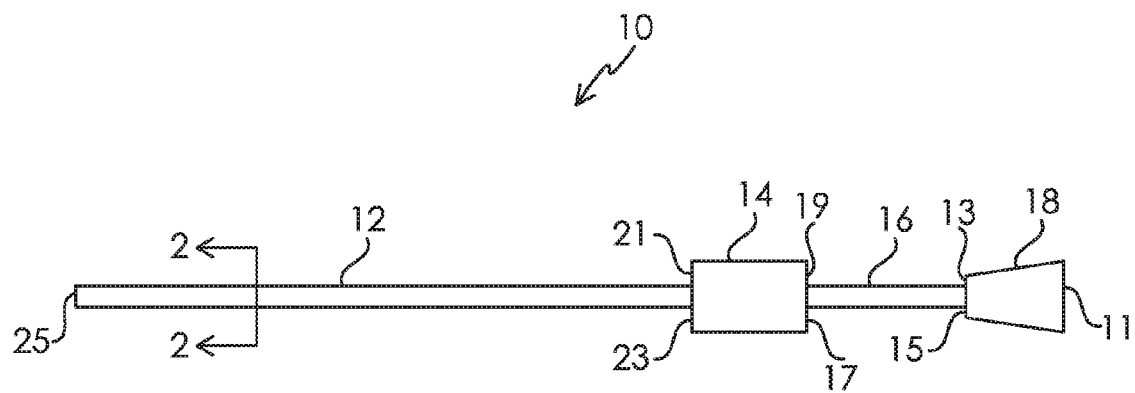
FIG. 1 is a perspective view of a catheter in accordance with one embodiment.

The following definitions and methods are provided to better define the present invention and to guide those of ordinary skill in the art in the practice of the present invention. Unless otherwise noted, terms are to be understood according to conventional usage by those of ordinary skill in the relevant art.

When introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

Aliphatic: unless otherwise indicated, "aliphatic" or "aliphatic group" means an optionally substituted, non-aromatic hydrocarbon moiety. The moiety may be, for example, linear, branched, or cyclic (e.g., mono or polycyclic such as fused, bridging, or spiro-fused polycyclic), or a combination thereof. Unless otherwise specified, aliphatic groups contain 1-20 carbon atoms.

Alkoxylated: unless otherwise indicated, the alkoxylated groups or moieties described herein are alkoxy pendant groups, or repeat units containing alkoxy pendant groups corresponding to the formula $—OR^3$ wherein $R^3$ is hydrocarbyl, substituted hydrocarbyl or heterocyclo, and preferably alkyl.

Alkyl: unless otherwise indicated, the alkyl groups described herein are preferably lower alkyl containing from one to eight carbon atoms in the principal chain and up to 20 carbon atoms. They may be linear, branched or cyclic and include methyl, ethyl, propyl, butyl, hexyl and the like.

Amino: unless otherwise indicated, the term "amino" as used herein alone or as part of another group denotes the moiety $—NR^1R^2$ wherein $R^1$, and $R^2$ are independently hydrogen, hydrocarbyl, substituted hydrocarbyl or heterocyclo.

Ammonium: unless otherwise indicated, the term "ammonium" as used herein alone or as part of another group denotes the moiety $—N^+R^1R^2R^3$ wherein $R^1$, $R^2$ and $R^3$ are independently hydrogen, hydrocarbyl, substituted hydrocarbyl or heterocyclo.

Amide or Amido: unless otherwise indicated, the "amide" or "amido" moieties represent a group of the formula $—CONR^1R^2$ wherein $R^1$ and $R^2$ are as defined in connection with the term "amino." "Substituted amide," for example, refers to a group of the formula $—CONR^1R^2$ wherein at least one of $R^1$ and $R^2$ are other than hydrogen. "Unsubstituted amido," for example, refers to a group of the formula $—CONR^1R^2$, wherein $R^1$ and $R^2$ are each hydrogen.

Anionic Monomer, Anionic Monomeric Unit or Anionic Repeat Unit: unless otherwise indicated, an "anionic monomer," "anionic monomeric unit" or "anionic repeat unit" is a monomer or monomeric unit bearing an anion or other anionic species, e.g., a group that is present in a negatively charged state or in a non-charged state, but in the non-charged state is capable of becoming negatively charged, e.g., upon removal of an electrophile (e.g., a proton (H+), for example in a pH dependent manner) or a protecting group (e.g., a carboxylic acid ester), or the addition of a nucleophile. In certain instances, the group is substantially negatively charged at an approximately physiological pH but undergoes protonation and becomes substantially neutral at a weakly acidic pH. The non-limiting examples of such groups include carboxyl groups, barbituric acid and derivatives thereof, xanthine and derivatives thereof, boronic acids, phosphinic acids, phosphonic acids, sulfinic acids, sulfonic acids, phosphates, and sulfonamides.

Anionic species or Anionic moiety: unless otherwise indicated, an "Anionic species" or an "Anionic moiety" is a group, residue or molecule that is present in a negatively charged or non-charged state, but in the non-charged state is capable of becoming negatively charged, e.g., upon removal of an electrophile (e.g., a proton (H+), for example in a pH dependent manner) or other protecting group (e.g., a carboxylic acid ester), or the addition of a nucleophile. In certain instances, the group, residue or molecule is substantially negatively charged at an approximately physiological pH but undergoes protonation and becomes substantially neutral at a weakly acidic pH.

Antibiofilm activity: unless otherwise indicated, "antibiofilm activity" may be quantified, for example, using a standard continuous flow assay. In one such assay, samples may be pre-incubated with 50% fetal bovine serum for 18-20 hours at 120 RPM at 37° C. Following preincubation, samples are then exposed to a subculture of bacteria via a modified CDC (mCDC) to make a bacterial suspension of $10^6$ CFU/mL in 1×PBS. The reactor is run in batch mode for 2 hours at 37° C. with agitation. Thereafter, the samples are transferred to a fresh reactor with a suitable growth media where flow of the sterile media (8 mL/min) runs 20-23 hours with agitation. In one preferred embodiment, the bacterial strain is *Staphylococcus epidermidis* (*S. epidermidis*, ATCC 35984), and the growth media used is 1:10 Tryptic soy broth (TSB)+0.25 wt % glucose. In an alternate preferred embodiment, the bacterial strain is *Escherichia coli* (*E. coli*, ATCC 25922) and the growth media is M63 media supplemented with 1 mM $MgSO_4$, 0.2% glucose, and 0.5% casamino acids. After incubation, the samples are rinsed five times in 100 mL of 1×PBS to remove bacteria not tightly attached. Then, accumulated bacteria on materials are macroscopically rated for biofilm surface coverage and are removed by sonication in a new solution of PBS and the total number of bacterial cells quantified through dilution plating. Preferably at least a 1, 2, 3 or 4 log reduction in bacterial count is found on the article with the non-fouling polymer layer relative to a reference substrate, that is, the same or an otherwise functionally equivalent substrate lacking the non-fouling polymer layer. An article that has a 1 log reduction in adhered bacteria relative to a reference substrate is said to have antibiofilm activity of 1 log. An article that has a 2 log reduction in adhered bacteria relative to a reference substrate is said to have antibiofilm activity of 2 log, and so forth.

Antimicrobial: unless otherwise indicated, "antimicrobial" refers to molecules and/or compositions that kill (i.e., microbicidal), inhibit the growth of (i.e., microbistatic), and/or prevent fouling by, microorganisms including bacteria, yeast, fungi, *mycoplasma*, viruses or virus infected cells, and/or protozoa. Antimicrobial activity with respect to bacteria may be quantified, for example, using a standard assay. In one such assay, samples may be pre-incubated with 50% fetal bovine serum for 18-20 hours at 120 RPM at 37° C. Following preincubation, samples are placed in *Staphylococcus aureus* (*S. aureus*, ATCC 25923) which has been diluted from an overnight culture to a planktonic concentration of $1-3 \times 10^5$ CFU/mL in 1% tryptone soy broth (TSB) diluted in 1×PBS or other suitable media. Samples are incubated with bacteria for 24-26 hrs with agitation (120 rpm) at 37° C. The concentration of TSB or other media can vary with the organism being used. After incubation, the samples are placed in 3 mL PBS for 5 min at 240 RPM at 37° C. to remove bacteria not tightly attached to the material. Then, accumulated bacteria on materials are removed by sonication in a new solution of PBS and the total number of bacterial cells are quantified through dilution plating. Preferably at least a 1, 2, 3 or 4 log reduction in bacterial count occurs relative to colonization on a reference substrate, that is, the same or an otherwise functionally equivalent substrate lacking the non-fouling polymer layer. A surface that has a lower bacterial count on it than the reference substrate may be said to reduce microbial colonization.

Anti-thrombogenic: unless otherwise indicated, "anti-thrombogenic" refers to the ability of a composition to resist thrombus formation. Anti-thrombogenic activity can be evaluated using an ex-vivo flow loop model of thrombosis. Briefly, up to 10 liters of fresh blood are collected from a single animal (bovine). This blood is heparinized to prevent coagulation, filtered to remove particulates, and autologous radio-labeled platelets are added. Within eight hours after blood harvesting, coated and uncoated articles are placed in a flow loop circuit, which pumps blood from a bath over the article and then back into the bath. A second internal flow loop circuit can be established for an article containing a lumen by connecting the two ports of the article through a 2nd peristaltic pump. The size of tubing into which the article is placed and speed of the blood flow may be adjusted based on the size of the article being tested. Preferably, when the articles are 14-15.5 French dialysis catheters, they are placed in a flow loop circuit with tubing diameter of approximately 12.5-25.4 mm inner diameter. Blood is pumped in the outer circuit at a rate of approximately 2.5 L/min, while blood in the inner circuit is pumped at a rate of approximately ~200-400 ml/min. When the articles are 10 French rods, they are placed in a flow loop circuit of approximately 6.4 mm inner diameter and blood flow rate is approximately 200 ml/min. After 60-120 minutes, the articles are removed, inspected visually for thrombus formation, and adhered platelets are quantified using a Gamma counter. For samples not containing a lumen, only an outer circuit may be used to measure thrombus on the outside of the device. Optionally, each of the ends of the articles may be trimmed up to 2 cm to eliminate end effects Aryl: unless otherwise indicated, the term "aryl" or "aryl group" refers to optionally substituted monocyclic, bicyclic, and tricyclic ring systems having a total of five to fourteen ring members, wherein at least one ring in the system is aromatic and wherein each ring in the system contains three to seven ring members. The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl groups.

Attached: unless otherwise indicated, two moieties or compounds are "attached" if they are held together by any interaction including, by way of example, one or more covalent bonds, one or more non-covalent interactions (e.g., hydrogen bonds, ionic bonds, static forces, van der Waals interactions, combinations thereof, or the like), or a combination thereof.

Biocompatibility: unless otherwise indicated, "biocompatibility" is the ability of a material to perform with an appropriate host response in a specific situation. This can be evaluated using International Standard ISO 10993. Biocompatible compositions described herein are preferably substantially non-toxic.

Biological fluids: unless otherwise indicated, "biological fluids" are fluids produced by organisms containing proteins and/or cells, as well as fluids and excretions from microbes. This includes, but is not limited to, blood, saliva, urine, cerebrospinal fluid, tears, semen, lymph, ascites, sputum, bone marrow, synovial fluid, aqueous humor, cerumen, broncheoalveolar lavage fluid, prostatic fluid, cowper's fluid or pre-ejaculatory fluid, sweat, fecal matter, cyst fluid, pleural and peritoneal fluid, chyme, chyle, bile, intestinal fluid, pus, sebum, vomit, mucosal secretion, stool water, pancreatic juice, lavage fluids from sinus cavities, bronchopulmonary aspirates, or any derivative thereof (e.g., serum, plasma).

Block Copolymer: unless otherwise indicated, a "block copolymer" comprises two or more homopolymer or copolymer subunits linked by covalent bonds. Block copolymers with two or three distinct blocks are called diblock copolymers and triblock copolymers, respectively. A schematic generalization of a diblock copolymer is represented by the formula $[A_aB_bC_c\ldots]_m\text{-}[X_xY_yZ_z\ldots]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: X-X-Y-Z-X-Y-Y-Z-Y-Z-Z . . . . A non-limiting, exemplary alternating random configuration may have the non-limiting form: X-Y-X-Z-Y-X-Y-Z-Y-X-Z . . . , and an exemplary regular alternating configuration may have the non-limiting form: X-Y-Z-X-Y-Z-X-Y-Z . . . . An exemplary regular block configuration may have the following non-limiting configuration: . . . X-X-X-Y-Y-Y-Z-Z-Z-X-X-X . . . , while an exemplary random block configuration may have the non-limiting configuration: . . . X-X-X-Z-Z-X-X-Y-Y-Y-Y-Z-Z-Z-X-X-Z-Z-Z- . . . . In a gradient polymer, the content of one or more monomeric units increases or decreases in a gradient manner from the a end of the polymer to the ω end. In none of the preceding generic examples is the particular juxtaposition of individual constitutional units or blocks or the number of constitutional units in a block or the number of blocks meant nor should they be construed as in any manner bearing on or limiting the actual structure of block copolymers forming a micelle described herein. As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

Branched: unless otherwise indicated, "branched" refers to a polymer structure in which a polymer chain divides into two or more polymer chains.

Brushes/Polymer Brushes: unless otherwise indicated, "brushes" or "polymer brushes" are used herein synonymously and refer to polymer chains that are bound to a surface generally through a single point of attachment using graft-from techniques. The polymers can be end-grafted (attached via a terminal group) or attached via a side chain or a position in the polymer chain other than a terminal position. The polymers can be linear or branched. For example, the polymer chains described herein can contain a plurality of side chains that contain zwitterionic groups. The side chains can consist of a single non-fouling moiety or monomer and/or a non-fouling oligomer (e.g., 2-10 monomeric residues) or polymer (e.g., >10 monomeric residues).

Carboxyammonium: unless otherwise indicated, a "carboxyammonium" moiety is a zwitterionic moiety comprising carboxylate and ammonium functionality and includes, for example, carboxyammonium monomers, carboxyammonium oligomers, carboxyammonium polymers, carboxyammonium repeat units, and other carboxyammonium-containing materials. Carboxybetaine monomers, oligomers, polymers, repeat units and other carboxybetaine materials are exemplary carboxyammonium moieties.

Catheter: is commonly used to identify a tubular instrument that is inserted into a human body cavity or orifice, naturally or surgically opened.

Catheter substrate: unless otherwise indicated, a "catheter substrate" is a catheter or one or more components thereof, such as a catheter body, juncture hub, extension line or connector.

Cationic Monomer, Cationic Monomeric Unit or Cationic Repeat Unit: unless otherwise indicated, a "cationic monomer," "cationic monomeric unit" or "cationic repeat unit" is a monomer or a monomeric or repeat unit (the terms "monomeric unit" and "repeat unit" being used interchangeably) bearing a cation or other cationic species, e.g., a moiety capable of having a positive charge upon addition of an electrophile (e.g., a proton (H+) or an alkyl cation, for example in a pH dependent manner) or removal of a protecting group or a nucleophile.

Cationic species or Cationic Moiety: unless otherwise indicated, a "Cationic species" or a "Cationic Moiety" is a group, residue or molecule that is present in a positively charged or non-charged state, but in the non charged state is capable of becoming positively charged, e.g., upon addition of an electrophile (e.g., a proton (H+), for example in a pH dependent manner) or removal of a protecting group or a nucleophile. In certain instances, the group, residue or molecule is permanently charged, e.g., comprises a quaternary nitrogen atom.

Coating: unless otherwise indicated, "coating" refers to any temporary, semi-permanent or permanent layer, or layers, treating or covering a surface. The coating may be a chemical modification of the underlying substrate or may involve the addition of new materials to the surface of the substrate. It includes any increase in thickness to the substrate or change in surface chemical composition of the substrate.

Complex Media: unless otherwise indicated, "complex media" refers to biological fluids or solutions containing proteins or digests of biological materials. Examples include, but are not limited to, cation-adjusted Mueller Hinton broth, tryptic soy broth, brain heart infusion, or any number of complex media, as well as any biological fluid.

Conformal and Conformality: unless otherwise indicated, "Conformal" or "Conformality," as used herein, in connection with a polymer layer on a surface such as an intraluminal surface or exterior surface of a catheter component shall mean the absence of individual regions on the surface that are uncoated by the polymer layer having a size greater than a specified area. For instance, a catheter component that is Conformal at a level of 1 $mm^2$ has no regions on the surface of that component larger than 1 $mm^2$ without a polymeric surface modification that is surrounded by regions on the surface having a surface modification; metaphorically, a catheter component having an intraluminal surface or exterior surface that has been modified with a polymer layer is Conformal at a level of 1 $mm^2$ has no "islands" on such surface larger than 1 $mm^2$ lacking the polymer layer surrounded by a "sea" on such surface having the polymer layer. As further example, an intraluminal surface of catheter component such as a catheter body lumen that is Conformal at a level of 1 $mm^2$ does not have any regions on the intraluminal surface of that component larger than 1 $mm^2$ without a hydrophilic surface modification surrounded by intraluminal surface of that component having a hydrophilic surface modification. This may be measured by staining the surface modification polymer, applying an IR probe or mapping technique, microscopy, laser profilometry, or other visual, physical or chemical characterization methods that provide sufficient resolution for the hydrophilic surface modification polymer.

Copolymer: unless otherwise indicated, "copolymer" refers to a polymer derived from two, three or more monomeric species and includes alternating copolymers, periodic copolymers, random copolymers, statistical copolymers and block copolymers.

Cysteine: unless otherwise indicated, "cysteine" refers to the amino acid cysteine or a synthetic analogue thereof, wherein the analogue contains a free sulfhydryl group.

Degradation Products: unless otherwise indicated, "degradation products" are atoms, radicals, cations, anions, or molecules other than water formed as the result of hydrolytic, oxidative, enzymatic, or other chemical processes.

The term "distal" refers to a direction relatively furthest from a clinician using a catheter described herein. For example, the end of a catheter placed within the catheter body of a patient is considered a distal end of the catheter, while the catheter end remaining outside the catheter body is a proximal end of the catheter.

Dry Thickness: unless otherwise indicated, "Dry Thickness," as used herein in connection with a polymer layer, shall mean the thickness of the polymer layer using a scanning electron microscope (SEM) or by analyzing the intensity of the chemical signals in the polymer layer, for instance, through the use of ATR-FTIR. To measure dry thickness using an SEM, the sample is freeze fractured for imaging by being submerged in liquid nitrogen then cracked with an ultra microtome blade. For metal substrates, they may be scored with a notch before a primer or the hydrophilic polymer is applied to make freeze fracturing easier. The freeze fracturing should break the article at a plane approximately orthogonal to the polymer modified surface in order to measure the thickness of the polymer layer normal to the substrate. The samples are sputter coated in gold for 90 seconds using a sputter coater and then imaged under high vacuum at 5 kV using an SE2 detector under a Field Emission Scanning Electron Microscope (SEM). Exemplary microtome blades include the Leica Ultracut UCT Ultramicrotome, exemplary sputter coaters include the Cressington 208HR, exemplary SEMs include the Supra55VP FESEM, Zeiss.

Fibrinogen Adsorption Assay: unless otherwise indicated, a "Fibrinogen Adsorption Assay" is an assay used to assess the capacity of a surface for fibrinogen. In the assay, test samples are placed in a suitable sized container, which may be a 96-well manifold, microcentrifuge tube, or other container. The volumes in the following are appropriate for a deep 96-well plate, but may be scaled to properly cover a device being tested. The samples are sterilized with 70% ethanol solution for thirty minutes and the test groups run with an n per run of 3-4. The sample container is blocked with 20 mg/mL Bovine Serum Albumin (BSA) in 1×PBS for 1 hour at 4° C., followed by three rinses with 1×PBS before samples are added. The sample is exposed to a solution containing 70 μg/mL unlabeled human fibrinogen, 1.4 μg/mL 1-125 radiolabeled human fibrinogen, 35-55 μg/mL BSA in water, optionally tri-sodium citrate, and optionally sodium chloride. The BSA is a common agent co-lyophilized with the radiolabeled fibrinogen. Optionally, the BSA and radiolabeled fibrinogen may have been dissolved from a lyophilized form that contains tri-sodium citrate and sodium chloride. To measure the protein adsorption on the intraluminal surface of a lumen, the lumen is completely filled with the fibrinogen test solution and the ends sealed, taking care to avoid exposing the protein solution to an air interface. The samples are incubated for one hour at 37° C. on an orbital shaker at 150 RPM. The test solution is then removed and four 1-minute rinses with a 10 mM NaI and one 1-minute rinse with 1×PBS are performed. The samples, optionally cut into smaller sections, are loaded into a gamma counter. The counter measures the radioactivity in 1-125 counts per minute for each sample and these data are used to calculate the absolute fibrinogen adsorption or a percent reduction of the non-fouling polymer layer samples versus a reference substrate, that is, the same or an otherwise functionally equivalent substrate lacking the non-fouling polymer layer. The percent reduction is equal to: (1−non-fouling sample CPM/Average CPM of the reference substrate)*100%.

Average Dry Thickness: unless otherwise indicated, "Average Dry Thickness," as used herein in connection with a polymer layer, shall mean the mean calculated by averaging the Dry Thickness of at least 3, and preferably at least 5, representative locations spaced approximately evenly across the portion of the catheter component carrying the polymer layer. For example, if a polymer layer is applied to a surface of a lumen in a catheter body, the representative locations (at the surface of the lumen) are approximately evenly spaced along the length of the lumen. It is preferred to measure the thickness at representative points across the longest dimension of the portion of the catheter component that is covered with the polymer layer. The standard deviation of the Average Dry Thickness is found by calculating the standard deviation of the Dry Thickness across at least 5, and preferably at least 10, representative locations spaced approximately evenly across the portion of the catheter component carrying the polymer layer.

Global Average Humidified Thickness: unless otherwise indicated, "Global Average Humidified Thickness," as used herein in connection with a polymer layer, shall mean the mean calculated by averaging the Humidified Thickness of at least 3, and preferably at least 5, representative locations spaced approximately evenly across the portion of the catheter component carrying the polymer layer. For example, if a polymer layer is applied to a surface of a lumen in a catheter body, the representative locations (at the surface of the lumen) are approximately evenly spaced along the length of the lumen. It is preferred to measure the thickness at representative points across the longest dimension of the portion of the catheter component that is covered with the polymer layer. The standard deviation of the Global Average Humidified Thickness is found by calculating the standard deviation of the Humidified Thickness across at least 5, and preferably at least 10, representative locations spaced approximately evenly across the portion of the catheter component carrying the polymer layer.

Global Average $R_{rms}$ Surface Roughness: unless otherwise indicated, "Global Average $R_{rms}$ Surface Roughness," as used herein in connection with a polymer layer, shall mean the mean calculated by averaging the $R_{rms}$ surface roughness of at least 5, and preferably at least 10, representative locations spaced approximately evenly across the portion of the catheter component carrying the polymer layer. For example, if a polymer layer is applied to a surface of a lumen in a catheter body, the representative locations (at the surface of the lumen) are approximately evenly spaced along the length of the lumen. It is preferred to measure the thickness at representative points across the longest dimension of the portion of the catheter component that is covered with the polymer layer. The standard deviation of the Global Average $R_{rms}$ Surface Roughness is found by calculating the standard deviation of the $R_{rms}$ Surface Roughness across at least 5, and preferably at least 10, representative locations spaced approximately evenly across the portion of the catheter component carrying the polymer layer.

Graft: unless otherwise indicated, the term "graft," as used herein in connection with a polymer, means the modification of the surface of a material with a polymer by a "graft-from", "graft-through", or a "graft-to" approach, or a combination thereof to form a grafted polymer.

Graft-from method: unless otherwise indicated, the term "graft-from," as used herein in connection with a method for the modification of a material with a polymer, shall mean the in situ polymerization and growth of a polymer at the surface of, or within a material.

Graft-from polymer: unless otherwise indicated, the term "graft-from polymer," as used herein, shall mean a polymer formed by a graft-from method.

Graft-through method: unless otherwise indicated, the term "graft-through," as used herein in connection with a method for the modification of a material with a polymer, shall mean the in situ polymerization of monomers in the neighborhood of the material that may polymerize through functional groups presented from the material surface. For example, the material may have vinyl groups presented from the surface through which polymerization occurs.

Graft-through polymer: unless otherwise indicated, the term "graft-through polymer," as used herein, shall mean a polymer formed by a graft-through method.

Graft-to method: unless otherwise indicated, the term "graft-to," as used herein in connection with a method for the modification of a material with a polymer shall mean the modification of the surface of a material with a presynthesized polymer Graft-to polymer: unless otherwise indicated, the term "graft-to polymer," as used herein, shall mean a grafted polymer formed by a graft-to method.

Heteroalkyl: unless otherwise indicated, the term "heteroalkyl" means an alkyl group wherein at least one of the backbone carbon atoms is replaced with a heteroatom.

Heteroaryl: unless otherwise indicated, the term "heteroaryl" means an aryl group wherein at least one of the ring members is a heteroatom, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., ═O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heteroatom: unless otherwise indicated, the term "heteroatom" means an atom other than hydrogen or carbon, such as a chlorine, iodine, bromine, oxygen, sulfur, nitrogen, phosphorus, boron, arsenic, selenium or silicon atom.

Heterocyclo: unless otherwise indicated, the terms "heterocyclo" and "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heterohydrocarbyl: unless otherwise indicated, the term "heterohydrocarbyl" means a hydrocarbyl group wherein at least one of the chain carbon atoms is replaced with a heteroatom.

Humidified Thickness: unless otherwise indicated, "humidified thickness," as used herein in connection with a polymer layer, shall mean the thickness of the polymer layer using an environmental scanning electron microscope (ESEM and approximately 26% relative humidity). To measure humidified thickness, the sample is freeze fractured for imaging by being submerged in liquid nitrogen then cracked with an ultra microtome blade. The freeze fracturing should break the catheter component at a plane orthogonal to the polymer modified surface in order to measure the thickness of the polymer layer normal to the substrate. After fracturing, the samples are soaked in water for at least one hour and then submerged in liquid nitrogen and fixed to a cold stage at −8° C. to −12° C. The samples are then imaged using a VPSE detector at the highest resolvable humidity (approximately 26% or 81 Pa) under a Scanning Electron Microscope (SEM) with an Environmental Scanning Electron Microscope (E-SEM). Exemplary microtome blades include the Leica Ultracut UCT Ultramicrotome, exemplary SEMs include the Supra55VP FESEM, Zeiss, and exemplary E-SEMs include the Zeiss EVO 55.

Hydrocarbon or Hydrocarbyl: unless otherwise indicated, the terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms Hydrophilic: unless otherwise indicated, "hydrophilic" refers to solvents, molecules, compounds, polymers, mixtures, materials, or functional groups which have an affinity for water. Such materials typically include one or more hydrophilic functional groups, such as hydroxyl, zwitterionic, carboxy, amino, amide, phosphate, sulfonyl, hydrogen bond forming, and/or ether groups.

Hydrophobic: unless otherwise indicated, "hydrophobic" refers to solvents, molecules, compounds, polymers, mixtures, materials, or functional groups that are repelled by water. Such materials typically contain non-polar functional groups.

Immobilization/Immobilized: unless otherwise indicated, "immobilization" or "immobilized" refers to a material or bioactive agent that is covalently or non-covalently attached directly or indirectly to a substrate. "Co-immobilization" refers to immobilization of two or more agents.

Initiator: unless otherwise indicated, "initiator" refers to a substance or a combination of substances that can produce a radical or other species under relatively mild conditions and promote polymerization reactions. For example, redox pairs as described elsewhere herein may be an initiator.

Humidified Thickness: unless otherwise indicated, "Humidified Thickness" is the mean Humidified Thickness calculated by averaging Humidified Thickness measurements of at least 3, and preferably at least 5, representative locations spaced approximately evenly across a cross section of a catheter component that spans approximately 10-40 micrometers. The standard deviation of the Humidified Thickness may be determined by calculating the standard deviation of the Humidified Thickness across at least 5, and preferably at least 10, representative locations spaced approximately evenly across a cross-section of a catheter component that spans approximately 10-40 micrometers.

Lumen Diameter: unless otherwise indicated, "Lumen Diameter," as used herein in connection with a catheter, shall mean the diameter of a circle with the same cross-sectional area of a lumen of a catheter component. For example, if a catheter has an oval lumen with cross-sectional area of 1 mm$^2$, the Lumen Diameter is the diameter of a circle with cross-sectional area of 1 mm$^2$.

Lumen Aspect Ratio: unless otherwise indicated, "Lumen Aspect Ratio," as used herein in connection with a catheter component, shall mean the ratio of the length of a lumen for a catheter component divided by the diameter of that lumen.

Midpoint Region: unless otherwise indicate, "Midpoint Region" as used herein in connection with a lumen refers to the region of the lumen at distances between 40% and 60% of the distance between the two ends of the lumen. For example, if the distance between the two ends of a lumen is 10 cm, the Midpoint Region would be the region of the lumen at distances between 4 and 6 cm measured from one of the lumen ends and in the direction of the other lumen end.

Non-Degradable: unless otherwise indicated, "non-degradable" refers to material compositions that do not react significantly within a biological environment either hydrolytically, reductively, enzymatically or oxidatively to cleave into smaller or simpler components.

Non-Fouling Composition/Non-Fouling Material/Non-Fouling Polymer/Non-Fouling Polymer Layer: unless otherwise indicated, a "non-fouling composition" or "non-fouling material" or "non-fouling polymer" or "non-fouling polymer layer" as used interchangeably herein, is a composition that provides or increases the protein resistance of a surface of an article to which the composition is attached. For example, when attached to a substrate such a composition may resist the adhesion of proteins, including blood proteins, plasma, cells, tissue and/or microbes to the substrate relative to the amount of adhesion to a reference substrate, that is, the same or an otherwise functionally equivalent substrate lacking the composition. Preferably, a substrate surface will be substantially non-fouling in the presence of human blood. Preferably the amount of adhesion will be decreased 20%, 30%, 40%, 50%, 60%, 70%, 80%, or more, for example, 85%, 90%, 95%, 99%, 99.5%, 99.9%, or more, relative to the reference substrate. One particularly preferred measure of the non-fouling character or protein resistance of a surface is the amount of fibrinogen adsorbed in a Fibrinogen Adsorption Assay as described herein. Preferably, the amount of adsorbed fibrinogen using the Fibrinogen Adsorption Assay described herein is <125 $ng/cm^2$, <90 $ng/cm^2$, <70 $ng/cm^2$, <50 $ng/cm^2$, <30 $ng/cm^2$, <20 $ng/cm^2$, <15 $ng/cm^2$, <12 $ng/cm^2$, <10 $ng/cm^2$, <8 $ng/cm^2$, <6 $ng/cm^2$, <4 $ng/cm^2$, <2 $ng/cm^2$, <1 $ng/cm^2$, <0.5 $ng/cm^2$, or <0.25 $ng/cm^2$.

Permeabilization agent: unless otherwise indicated, "permeabilization agent" includes substances that may be delivered from a medical device along with an antimicrobial in order to enhance the penetration of that antimicrobial into surrounding tissue. Examples of permeabilization agents include vegetable oils and *Eucalyptus* oil.

The term "proximal" refers to a direction relatively closer to a clinician using a catheter described herein. For example, the end of a catheter placed within the body of a patient is considered a distal end of the catheter, while the catheter end remaining outside the body is a proximal end of the catheter.

Polymer: unless otherwise indicated, "polymer" includes natural and synthetic, homopolymers and copolymers comprising multiple repeat units and, unless otherwise indicated, may be linear, branched, or dendritic. Examples of copolymers include, but are not limited to, random copolymers and block copolymers, smart polymers, temperature responsive (e.g., NIPAM), and pH responsive (e.g., pyridyl based) polymers.

Polypeptide/Peptide/Oligopeptide: unless otherwise indicated, "polypeptide," "peptide," and "oligopeptide" encompass organic compounds composed of amino acids, whether natural, synthetic or mixtures thereof, that are linked together chemically by peptide bonds. Peptides typically contain 3 or more amino acids, preferably more than 9 and less than 150, more preferably less than 100, and most preferably between 9 and 51 amino acids. The polypeptides can be "exogenous," or "heterologous," i.e., production of peptides within an organism or cell that are not native to that organism or cell, such as human polypeptide produced by a bacterial cell. Exogenous also refers to substances that are not native to the cells and are added to the cells, as compared to endogenous materials, which are produced by the cells. The peptide bond involves a single covalent link between the carboxyl group (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

Quaternary Nitrogen: unless otherwise indicated, "quaternary nitrogen," as used herein, refers to a nitrogen atom that is a member of a quaternary ammonium cation.

$R_{rms}$ Surface Roughness: unless otherwise indicated, "$R_{rms}$ Surface Roughness" refers to root mean squared roughness of a surface, which measures the vertical deviations of a real surface from its ideal form. The roughness refers to surface micro-roughness which may be different than measurements of large scale surface variations. Preferably, this may be measured using atomic force microscopy (MFP-3D, Aslyum) across a field of approximately 1-30 μm by 1-30 μm, preferably 20 μm by 20 μm. The sample is washed with purified water to remove surface salts and then air dried. A standard silicon cantilever (Olympus AC160TS, spring constant 42 N/m) is employed for the measurement with an AC/Tapping mode. The $R_{rms}$ surface roughness is calculated by the software (IGOR Pro) attached with the AFM machine. Alternatively the roughness can be measured using a stylus profilometer. For example, the sample surface roughness can be measured by a Tencor P-16+ profilometer with a 60 degree, 2 μm diamond tip stylus. Preferably, an 800 μm scan length is chosen with 20 μm/second scan rate, 50 Hz scan frequency, and 2 μg loading force. At least three different sites are measured for the same sample, and the surface roughness is averaged from at least three samples. Alternatively, the $R_{rms}$ surface roughness can be measured preferably by non-contact methods, including using optical profilometers. For example, the sample surface roughness is measured by an optical profilometer (Zeta Z20 or Olympus Lext OLS4000). Preferably a 3-D image is taken by the optical profilometer under a 50× objective lens, and the sample's surface roughness is then measured along at least three different lines across the image. At least three different spots are measured and the surface roughness is averaged from at least three samples. In a preferred example an Olympus LEXT OLS4000 3D Laser Measuring Microscope is employed for roughness measurements and 3D imaging. A LEXT microscope utilizing low wavelength optical technology with a 408 nm laser in combination with confocal scanning can be used for the measurement. Samples to be measured are mounted on a glass slide by double-sided tape. Digital 3-D images are taken with the Olympus LEXT OLS4000 laser confocal microscope ("LEXT") under an Olympus MPLAPON 50× objective lens. The digital images taken in this way have a 256×256 μm field area. The Z-direction repeatability for this LEXT machine has been certified by Olympus to be less than 0.012 μm. To measure the roughness, at least three images have been taken from each sample and the $R_{rms}$ roughness is calculated using a 9 μm cut-off length.

Solvent Extractable Polymerization Initiator: unless otherwise indicated, "Solvent Extractable Polymerization Initiator" refers to any compound capable of starting radical polymerization that has been incorporated within an article, wherein either the initiator or its degradation products may be extracted from the article using a suitable solvent. In general, extractions can use nonpolar or polar solvents. For example, extraction solvents such as water, acetone or ethanol; and/or other extraction solvents in which the solubility of the initiator and/or its degradation products is at least 1 mg/L can be used. The extraction should be carried out for a sufficient time such that the change in concentration of the extract is not increasing more than 5% per hour. Alternatively, extraction can be performed until the amount of extracted material in a subsequent extraction is less than 10% of that detected in the initial extraction, or until there is no analytically significant increase in the cumulative extracted material levels detected. Extraction conditions include: 37° C. for 72 h; 50° C. for 72 h; 70° C. for 24 h; 121° C. for 1 h. Extraction ratio includes 6 $cm^2$/mL surface area/volume and/or 0.2 g sample/mL. In some instances, complete dissolution of the substrate may be appropriate. Materials shall be cut into small pieces before extraction to enhance submersion in the extract media, for example, for polymeric substrates, pieces approximately 10 mm×50 mm or 5 mm×25 mm are appropriate. The instrumentation used includes high-performance liquid chromatography-photo-diode array detection-mass spectrometry (HPLC-PDA-MS) for organics analysis; gas chromatography-mass spectrometry (GC-MS) for organics analysis; inductively coupled plasma-optical emission spectroscopy or mass spectrometry (ICP-OES or ICP-MS) for metals analysis; and sometimes ion chromatography (IC) for inorganics and ion analysis. Sometimes more advanced MS detectors such as time-of-flight (TOF) are used to obtain accurate mass information. Hexane and alcohol extractions are analyzed by GC-MS. Water and alcohol extractions are analyzed by HPLC. The initiator or its degradation products may be quantified and/or detected in the substrate or grafted polymer by the previously described methods. These include ATR-FTIR, electron spectroscopy for chemical analysis (ESCA, also called X-ray photoelectron spectroscopy, XPS), Secondary Ion Mass Spectrometry (SIMS), and surface-enhanced Raman spectroscopy (SERS). For example, peroxide may be detected spectrophotometrically using any of the following three methods: the iodide method (oxidation of sodium iodide by peroxides in the presence of ferric chloride), the DPPH method (treatment with 1,1-diphenyl-2-picrylhydrazyl, a radical scavenger, to decompose the peroxides), or the peroxidase method (reduction with glutathione, catalyzed by glutathione peroxidase, followed by measuring the coupled oxidation of NADPH in the presence of glutathione reductase). See, for example, Fujimoto et al., Journal of Polymer Science Part A: Polymer Chemistry, Vol. 31, 1035-1043 (1993).

Stable: unless otherwise indicated, "stable," as used herein in reference to a material, means that the material retains functionality over extended periods of time. In one embodiment, the referenced material retains at least 90% of a referenced activity (or property) for at least 30 days at 37° C. in at least one of phosphate buffered saline containing protein, media, or serum, or in vivo. In one embodiment, the reference material retains at least 80% of a referenced activity (or property) for at least 90 days at 37° C. in at least one of phosphate buffered saline containing protein, media, or serum, or in vivo. In one embodiment, the referenced material retains at least 90% of the referenced activity (or property) for at least 30 days at 37° C. and at least 80% of the referenced activity (or property) for at least 90 days at 37° C. The referenced activity or property may include surface contact angle, non-fouling, anti-thrombogenic, and/or antimicrobial activity.

Static Contact Angle: unless otherwise indicated, "Static Contact Angle" is the angle at which a water/vapor interface meets a substrate surface at or near equilibrium conditions. The contact angle is measured by first soaking the samples with pure ethanol for 5 minutes and washing with PBS three times. The samples are then soaked within PBS (150 mM, pH 7.4) for 24 hours and washed three times with purified water. Then the samples are dried under a flow of air for 5 min before testing. A drop of purified water (e.g., 1 μL) is deposited on the test surface, the shape of the droplet is photographed by a microscope with a CCD camera using a video contact angle system (e.g., VCA 2000, AST Inc.), and the contact angle is then determined (using, for example, a VCA Optima XE). The size of the water droplet used to determine the contact angle may vary depending upon the substrate type and composition. For a 5 French device, for instance, an 0.1 μL drop of purified water may be used.

Substantially Hemocompatible: unless otherwise indicated, "substantially hemocompatible" means that the composition is substantially non-hemolytic, in addition to being non-thrombogenic and non-immunogenic, as tested by appropriately selected assays for thrombosis, coagulation, and complement activation as described in ISO 10993-4.

Substantially Non-Cytotoxic: unless otherwise indicated, "substantially non-cytotoxic" refers to a composition that does not substantially change the metabolism, proliferation, or viability of mammalian cells that contact the surface of the composition. These may be quantified by the International Standard ISO 10993-5 which defines three main tests to assess the cytotoxicity of materials including the extract test, the direct contact test and the indirect contact test.

Substantially Non-Hemolytic Surface: unless otherwise indicated, "substantially non-hemolytic surface" means that the composition does not lyse 50%, preferably 20%, more preferably 10%, even more preferably 5%, most preferably 1%, of human red blood cells when the following assay is applied: a stock of 10% washed pooled red blood cells (Rockland Immunochemicals Inc, Gilbertsville, Pa.) is diluted to 0.25% with a hemolysis buffer of 150 mM NaCl and 10 mM Tris at pH 7.0. A 0.5 $cm^2$ antimicrobial sample is incubated with 0.75 mL of 0.25% red blood cell suspension for 1 hour at 37° C. The solid sample is removed and cells are spun down at 6000 g, the supernatant is removed, and the OD414 measured on a spectrophotometer. Total hemolysis is defined by diluting 10% of washed pooled red blood cells to 0.25% in sterile deionized (DI) water and incubating for 1 hour at 37° C., and 0% hemolysis is defined using a suspension of 0.25% red blood cells in hemolysis buffer without a solid sample.

Substantially Non-Toxic: unless otherwise indicated, "substantially non-toxic" means a surface that is substantially hemocompatible and substantially non-cytotoxic.

Substituted/Optionally Substituted: unless otherwise indicated, the term "substituted" and "optionally substituted" means that the referenced group is or may be substituted with one or more additional suitable group(s), which may be individually and independently selected, for example, from acetals, acyl, acyloxy, alkenoxy, alkoxy, alkylthio, alkynoxy, amido, amino, aryl, aryloxy, arylthio, azido, carbonyl, carboxamido, carboxyl, cyano, esters, ethers, hydrocarbyl, substituted hydrocarbyl, heterohydrocarbyl, substituted heterohydroalkyl, cycloalkyl, halogen, heteroalicyclic, heteroaryl, hydroxy, isocyanato, isothiocyanato, ketals, keto, mercapto, nitro, perhaloalkyl, silyl, sulfamoyl, sulfate, sulfhydryl, sulfonamido, sulfonate, sulfonyl, sulfoxido, thiocarbonyl, thiocyanato, thiol, and/or the protected derivatives thereof. It will be understood that "substitution" or "substituted" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Substrate: unless otherwise indicated, "substrate" refers to the material from which a hydrophilic polymer is grafted.

Sulfoammonium: unless otherwise indicated, a "sulfoammonium" moiety is a zwitterionic moiety comprising sulfate and ammonium functionality and includes, for example, sulfoammonium monomers, sulfoammonium oligomers, sulfoammonium polymers, sulfoammonium repeat units, and other sulfoammonium-containing materials. Sulfobetaine monomers, oligomers, polymers, repeat units, and other sulfobetaine materials are exemplary sulfoammonium moieties.

Tether/Tethering Agent/Linker: unless otherwise indicated, "tether" or "tethering agent" or "linker," as used herein synonymously, refers to any molecule, or set of molecules, or polymer used to covalently or non-covalently immobilize one or more non-fouling materials, one or more bioactive agents, or combinations thereof on a material where the molecule remains as part of the final chemical composition. The tether can be either linear or branched with one or more sites for immobilizing bioactive agents. The tether can be any length. However, in one embodiment, the tether is greater than 3 angstroms in length. The tether may be non-fouling, such as a monomer, oligomer, or polymer or a non-fouling non-zwitterionic material. The tether may be immobilized directly on the substrate or on a polymer, either of which may be non-fouling.

Tip Region: unless otherwise indicated, "Tip Region," as used herein, shall mean the terminal 10 cm length of the catheter body at the distal end of the catheter body.

Undercoating Layer: unless otherwise indicated, "undercoating layer" refers to any coating, or combination of coatings, incorporated into a substrate from which a hydrophilic polymer is grafted.

Zwitterion/Zwitterionic Material: unless otherwise indicated, "zwitterion" or "zwitterionic material" refers to a macromolecule, material, or moiety possessing both cationic and anionic groups. In most cases, these charged groups are balanced, resulting in a material with zero net charge.

Zwitterionic Polymers: unless otherwise indicated, "zwitterionic polymers" may be homopolymers or copolymers and include both polyampholytes (e.g., polymers with the charged groups on different monomer units) and polybetaines (polymers with the anionic and cationic groups on the same monomer unit). Exemplary zwitterionic polymers include alternating copolymers, statistical copolymers, random copolymers and block copolymers of two, three or more monomers.

DETAILED DESCRIPTION OF THE PREFERRED EMBODIMENTS

In accordance with the present invention, the intraluminal and exterior surfaces of a catheter, or at least those intraluminal and exterior catheter surfaces that are designed to be placed within a human body, to contact the bloodstream or to introduce a fluid to or withdraw a fluid from a patient may be modified with a hydrophilic polymer, sometimes referred to herein as a non-fouling polymer, to reduce microbial contamination/biofilm and thrombus attachment. Although certain catheter types and styles are described herein, the present invention is not limited to any specific type of catheter and the structures and combinations described herein are intended to be merely exemplary. It should be appreciated that the surface modifications described herein can be applied to any type of known catheter design.

In accordance with one aspect of the present invention, it has been found that surfaces of a catheter or a component thereof may be modified with a hydrophilic polymer layer by incorporating one or more polymerization initiator(s) into the catheter substrate, for example, by imbibing the substrate with the initiator(s) or depositing a layer onto the catheter substrate that comprises the initiator(s), and grafting a polymer from the catheter substrate. In a particularly preferred embodiment, the hydrophilic polymeric material is grafted from the catheter substrate in a polymerization mixture comprising monomer and a solvent system wherein the catheter substrate is not significantly swelled by the solvent system and the incorporated initiator has limited solubility in the solvent system. Stated differently, the initiator(s) incorporated into the catheter substrate have reversed phase properties compared to the solvent system especially in terms of hydrophilicity. Without being bound to any particular theory, it is believed that this method provides a relatively high local concentration of initiator(s) at or near the catheter substrate surface/polymerization mixture interface, and favors grafting from the catheter substrate and the grafted polymer to form a branched polymer.

Regardless of the theory, the grafted polymers of the present invention preferably comprise a relatively dense, branched and hydrophilic structure that uniformly covers catheter (or catheter component) surface defects and enhances performance. As a result, catheters or one or more components thereof having a surface modified by the grafted polymers possess improved anti-fouling, and/or antithrombotic characteristics and, in certain embodiments, improved antimicrobial characteristics.

Generally speaking, small initiator molecules can be concentrated at or near the catheter substrate surface, where polymerization is initiated and propagated, more readily than larger polymer molecules synthesized in solution. As a result, and as compared to graft-to coatings, greater surface densities can be achieved with graft-from coatings which, in turn, tends to improve non-fouling performance. Additionally, longer polymer chains and/or branched non-fouling chains may further improve performance.

Catheters typically comprise any of a wide range of materials. Certain of these materials, by virtue of their intrinsic characteristics, exhibit a greater resistance to protein adsorption and cell/microorganism adhesion; for example, the hydrophilic materials tend to exhibit less protein adsorption than hydrophobic materials. In addition, methods of manufacture can greatly affect the surface characteristics of such materials; for example, manufacturing methods may affect the porosity of a material, its roughness (micro-roughness and macro-roughness), incorporation of foreign-body inclusions that project from the surface of the material, and similar surface characteristics. Each of these, and other factors, may contribute to a material's resistance (or lack thereof) to protein adsorption and/or cell/microorganism adhesion.

Without being bound to any particular theory, it is presently believed that the polymerization methods of the present invention provide a surface modification, that is, a hydrophilic polymer layer, having a branched structure which disfavors protein adsorption and/or cell/microorganism adhesion and which may, in addition, conceal or otherwise alter the sites in a catheter substrate that favor the adhesion of cells, bacteria or other microorganisms. Thus, for example, and relative to the (unmodified) surface of the catheter (or component thereof), the grafted polymer layer may cover or even, partially or completely fill, scratches, pinholes, voids or other defects in the surface of the catheter (or component thereof) that could potentially otherwise serve as a site for a performance failure. By way of further example, grafted polymer layers having a thickness that is at least as great as the surface roughness of the (unmodified) surface of the catheter (or component thereof), that are relatively uniform, that are sufficiently dense, and/or are significantly hydrophilic can significantly increase a material's resistance to protein adsorption and/or cell/microorganism adhesion.

The modified surfaces of the catheters or catheter components of the present invention that comprise a hydrophilic polymer exhibit low fibrinogen adsorption in a fibrinogen adsorption assay. In general, the modified surface exhibits a fibrinogen adsorption of less than 125 ng/cm$^2$ in a fibrinogen adsorption assay in which samples are incubated for 60 minutes at 37° C. in 70 μg/mL fibrinogen derived from human plasma, and the amount of adsorbed fibrinogen is determined using a standard protocol, preferably by using radiolabeled fibrinogen. In one embodiment, the modified surface exhibits a fibrinogen adsorption of less than 90 ng/cm$^2$ in a fibrinogen adsorption assay in which samples are incubated for 60 minutes at 37° C. in 70 μg/mL fibrinogen derived from human plasma, and the amount of adsorbed fibrinogen is determined using a standard protocol, preferably by using radiolabeled fibrinogen. In one embodiment, the modified surface exhibits a fibrinogen adsorption of less than 70 ng/cm$^2$ in a fibrinogen adsorption assay in which samples are incubated for 60 minutes at 37° C. in 70 µg/mL fibrinogen derived from human plasma, and the amount of adsorbed fibrinogen is determined using a standard protocol, preferably by using radiolabeled fibrinogen. In one embodiment, the modified surface exhibits a fibrinogen adsorption of less than 50 ng/cm$^2$ in a fibrinogen adsorption assay in which samples are incubated for 60 minutes at 37° C. in 70 µg/mL fibrinogen derived from human plasma, and the amount of adsorbed fibrinogen is determined using a standard protocol, preferably by using radiolabeled fibrinogen. Preferably, the modified surface exhibits a fibrinogen adsorption of less than 30 ng/cm$^2$ in such an assay. More preferably, in certain embodiments the modified surface exhibits a fibrinogen adsorption of less than 20 ng/cm$^2$ in such an assay. Still more preferably, in certain embodiments the modified surface exhibits a fibrinogen adsorption of less than 15 ng/cm$^2$ in such an assay. In some embodiments, the modified surface exhibits a fibrinogen adsorption of less than 12 ng/cm$^2$ in such an assay. In some embodiments, the modified surface exhibits a fibrinogen adsorption of less than 10 ng/cm$^2$ in such an assay. In some embodiments, the modified surface exhibits a fibrinogen adsorption of less than 8 ng/cm$^2$ in such an assay. In some embodiments, the modified surface exhibits a fibrinogen adsorption of less than 6 ng/cm$^2$ in such an assay. In some embodiments, the modified surface exhibits a fibrinogen adsorption of less than 4 ng/cm$^2$ in such an assay. In some embodiments, the modified surface exhibits a fibrinogen adsorption of less than 2 ng/cm$^2$ in such an assay. In some embodiments, the modified surface exhibits a fibrinogen adsorption of less than 1 ng/cm$^2$ in such an assay. In some embodiments, the modified surface exhibits a fibrinogen adsorption of less than 0.5 ng/cm$^2$ in such an assay. In some embodiments, the modified surface exhibits a fibrinogen adsorption of less than 0.25 ng/cm$^2$ in such an assay. In one embodiment, the grafted polymer in each of the foregoing examples recited in this paragraph is a zwitterionic polymer. In one embodiment, the grafted polymer in each of the foregoing examples and embodiments recited in this paragraph is a polymer containing phosphorylcholine, carboxyammonium or sulfoammonium repeat units. In one embodiment, the grafted polymer in each of the foregoing examples and embodiments recited in this paragraph is a polymer containing sulfobetaine or carboxybetaine repeat units. In one embodiment, the grafted polymer in each of the foregoing examples and embodiments recited in this paragraph is a zwitterionic polymer and the zwitterionic polymer is grafted from a polyurethane polymer or copolymer. In one embodiment, the grafted polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the grafted polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

Preferred embodiments also show reduction in thrombus for catheter substrates having a hydrophilic polymer layer of the present invention. For example, thrombus reduction of modified catheter substrates, i.e., catheter substrates having a grafted polymer layer can be assessed relative to a reference catheter substrate, i.e., the same or an otherwise functionally equivalent substrate lacking the hydrophilic polymer layer, by exposing them to freshly harvested bovine blood, heparinized, with radiolabeled platelets, in a flow loop for 2 hours. As an assessment of anti-thrombogenic performance, samples are placed in an ex-vivo flow loop model of thrombosis. Anti-thrombogenic activity can be evaluated using an ex-vivo flow loop model of thrombosis. Briefly, up to 10 liters of fresh blood are collected from a single animal (bovine). This blood is heparinized to prevent coagulation, filtered to remove particulates, and autologous radio-labeled platelets are added. Within eight hours after blood harvesting, coated and uncoated articles are placed in a flow loop circuit, which pumps blood from a bath over the article and then back into the bath. A second internal flow loop circuit can be established for a substrate containing a lumen by connecting the two ports of the substrate through a second peristaltic pump. The size of tubing into which the article is placed and speed of the blood flow may be adjusted based on the size of the article being tested. Preferably, when the articles are 14-15.5 French dialysis catheters, they are placed in a flow loop circuit with tubing diameter of approximately 12.5-25.4 mm inner diameter. Blood is pumped in the outer circuit at a rate of approximately 2.5 L/min, while blood in the inner circuit is pumped at a rate of approximately ~200-400 ml/min. When the articles are 5 French PICC catheter shafts, they are placed in a flow loop circuit of approximately 6.4 mm inner diameter and blood flow rate is approximately 200 mL/min. The lumens may be locked with a solution, for example saline, during evaluation. Alternatively, the distal tip may be sealed, for example with epoxy, during evaluation. When the articles are 10 French rods, they are placed in a flow loop circuit of approximately 6.4 mm inner diameter and blood flow rate is approximately 200 ml/min. After 60-120 minutes, the articles are removed, inspected visually for thrombus formation, and adhered platelets are quantified using a Gamma counter. For samples not containing a lumen, only an outer circuit may be used to measure thrombus on the outside of the device. In this assay, preferred embodiments show at least an 80% reduction relative to reference substrate in adsorbed platelets and substantial visual reduction of thrombus. For example, in certain embodiments there is at least a 90% reduction in adsorbed platelets for modified substrates relative to reference substrates. Preferred embodiments show at least a 98% reduction in adsorbed platelets for modified substrates relative to reference substrates. Alternatively, in a preferred embodiment, the thrombogenecity of a modified substrate is reduced relative to the non-modified substrate, after exposure to a 47% (w/v) sodium citrate solution in DI water for greater than 3 days. Embodiments show a visual reduction of thrombus relative to for modified substrates relative to reference substrates. Preferred embodiments show at least an 80% reduction of a modified substrate relative to a reference substrate in adsorbed platelets and substantial visual reduction of thrombus. Preferred embodiments show at least a 90% reduction in adsorbed platelets for modified substrates relative to reference substrates. Preferred embodiments show at least a 98% reduction in adsorbed platelets for modified substrates relative to reference substrates. Alternatively, the thrombogenecity of preferred embodiments are reduced relative to the non-modified substrate after exposure to animal serum and/or plasma. For example, the thrombogenecity of preferred embodiments are reduced after 55 day exposure to citrated human plasma at 37° C. for modified substrates relative to reference substrates. Embodiments show a visual reduction of thrombus for modified substrates relative to reference substrates. Preferred embodiments show at least an 80% reduction for modified substrates relative to reference substrates in adsorbed platelets and substantial visual reduction of thrombus. Preferred embodiments show at least a 90% reduction in adsorbed platelets for modified substrates relative to reference substrates. Preferred embodiments show at least a 98% reduction in adsorbed platelets for modified substrates relative to reference substrates.

Preferred embodiments show antibiofilm activity for modified catheter substrates of at least 0.5 log, 1 log, 1.5 log, 2 log, 2.5 log, 3 log, or 4 log. More preferred embodiments have antibiofilm activity after extended exposures to PBS, serum, or plasma products. In one preferred embodiment, antibiofilm activity of 1 log is achieved after 30 days storage in PBS at 37° C. In a further preferred embodiment, antibiofilm activity of 1 log is achieved after 90 days storage in PBS at 37° C. In one preferred embodiment, antibiofilm activity of 2 log is achieved after 30 days storage in PBS at 37° C. In a further preferred embodiment, antibiofilm activity of 2 log is achieved after 90 days storage in PBS at 37° C. In one preferred embodiment, antibiofilm activity of 1 log is achieved after 30 days storage in citrated human plasma at 37° C. In a further preferred embodiment, antibiofilm activity of 1 log is achieved after 90 days storage in citrated human plasma at 37° C. In one preferred embodiment, antibiofilm activity of 2 log is achieved after 30 days storage in citrated human plasma at 37° C. In a further preferred embodiment, antibiofilm activity of 2 log is achieved after 90 days storage in citrated human plasma at 37° C.

Preferred embodiments show resistance to protein adsorption after extended exposure to PBS, which may indicate hydrolytic stability. In some embodiments, the modified surface of the catheter substrate exhibits a fibrinogen adsorption of less than 125 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 90 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 70 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 50 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 30 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 20 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 15 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 12 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 10 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 8 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 6 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 4 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 2 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 1 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 0.5 $ng/cm^2$ in a fibrinogen adsorption assay in which samples are incubated for 60 minutes at 37° C. in 70 µg/mL fibrinogen derived from human plasma after 30 days exposure to PBS at 37° C. In some embodiments, the modified surface of the catheter substrate exhibits a fibrinogen adsorption of less than 0.25 $ng/cm^2$ in a fibrinogen adsorption assay in which samples are incubated for 60 minutes at 37° C. in 70 µg/mL fibrinogen derived from human plasma after 30 days exposure to PBS at 37° C.

Preferred embodiments show resistance to protein adsorption after extended exposure to PBS, which may indicate hydrolytic stability. In some embodiments, the modified surface of the catheter substrate exhibits a fibrinogen adsorption of less than 125 $ng/cm^2$ in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 90 $ng/cm^2$ in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 70 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 50 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 30 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 20 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 15 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 12 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 10 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 8 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 6 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 4 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 2 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 1 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 0.5 ng/cm² in a fibrinogen adsorption assay in which samples are incubated for 60 minutes at 37° C. in 70 µg/mL fibrinogen derived from human plasma after 90 days exposure to PBS at 37° C. In some embodiments, the modified surface of the catheter substrate exhibits a fibrinogen adsorption of less than 0.25 ng/cm² in a fibrinogen adsorption assay in which samples are incubated for 60 minutes at 37° C. in 70 µg/mL fibrinogen derived from human plasma after 90 days exposure to PBS at 37° C.

In one embodiment the surface modification, i.e., the hydrophilic polymer, has a thickness which is at least equal to the surface roughness of the catheter substrate surface. For example, if the surface of a catheter substrate has a global average $R_{rms}$ surface roughness of 100 nm, it is preferred in this embodiment that the hydrophilic polymer layer have an Average Dry Thickness of at least 100 nm. In some embodiments, the catheter substrate surface is relatively smooth, e.g., a global average $R_{rms}$ surface roughness of 2 nm. In other embodiments, the catheter substrate surface is significantly rougher, e.g., a global average $R_{rms}$ surface roughness of 1 µm. In other embodiments, the catheter substrate surface will have a surface roughness intermediate of these values, e.g., a global average $R_{rms}$ surface roughness of 75-250 nm. In each of these embodiments, it is preferred that the thickness of the hydrophilic polymer layer exceed the global average $R_{rms}$ surface roughness of the catheter substrate surface. Thus, for example, in one embodiment the Average Dry Thickness of the hydrophilic polymer layer is at least 110% of the global average $R_{rms}$ surface roughness of the catheter substrate surface. By way of further example, the Average Dry Thickness may be at least 200% of the global average $R_{rms}$ surface roughness of the catheter substrate surface. By way of yet further example, the Average Dry Thickness may be at least 500% of the global average $R_{rms}$ surface roughness of the catheter substrate surface. By way of yet further example, the Average Dry Thickness may be at least 1,000% of the global average $R_{rms}$ surface roughness of the catheter substrate surface. In a preferred embodiment, the Average Dry Thickness of the hydrophilic polymer layer is determined using a scanning electron microscope (SEM) under vacuum or by analyzing the intensity of the chemical signals in the polymer layer, for instance, through the use of ATR-FTIR and global average $R_{rms}$ surface roughness is determined using an atomic force microscope. The hydrophilic polymer is preferably a non-fouling hydrophilic polymer. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In one embodiment, the hydrophilic polymer layer does not significantly increase the surface roughness. For example, in one embodiment, the modified surface, i.e., the surface of the catheter substrate (i.e., the catheter or one or more components thereof) with the hydrophilic polymer, has a surface roughness value that is less than 300% of the global average $R_{rms}$ surface roughness of the catheter substrate surface without the hydrophilic polymer layer. By way of further example, in one such embodiment, the global average $R_{rms}$ surface roughness of the modified surface is no more than 250% of the global average $R_{rms}$ surface roughness of the catheter substrate surface without the hydrophilic polymer layer. By way of further example, in one such embodiment, the global average $R_{rms}$ surface roughness of the modified surface is no more than 200% of the global average $R_{rms}$ surface roughness of the catheter substrate surface without the hydrophilic polymer layer. By way of further example, in one such embodiment, the global average $R_{rms}$ surface roughness of the modified surface is no more than 150% of the global average $R_{rms}$ surface roughness of the catheter substrate surface without the hydrophilic polymer layer. By way of further example, in one such embodiment, the global average $R_{rms}$ surface roughness of the modified surface is no more than the global average $R_{rms}$ surface roughness of the catheter substrate surface without the hydrophilic polymer layer.

In one embodiment, and particularly for catheters or one or more components thereof having surfaces with relatively large surface roughness values, the hydrophilic polymer layer may reduce the surface roughness; stated differently, the modified surface, i.e., the surface of the catheter substrate with the hydrophilic polymer, has less surface roughness than the surface of the catheter substrate. For example, in one such embodiment the global average $R_{rms}$ surface roughness of the modified surface is at least 50% less than the global average $R_{rms}$ surface roughness of the surface of the article without the hydrophilic polymer layer. By way of further example, in one such embodiment the global average $R_{rms}$ surface roughness of the modified surface is at least 25% less than the global average $R_{rms}$ surface roughness of the catheter substrate surface without the hydrophilic polymer layer. By way of further example, in one such embodiment the global average $R_{rms}$ surface roughness of the modified surface is at least 10% less than the global average $R_{rms}$ surface roughness of the catheter substrate surface without the hydrophilic polymer layer. By way of further example, in one such embodiment global average $R_{rms}$ surface roughness of the modified surface is at least 5% less than the global average $R_{rms}$ surface roughness of the catheter substrate surface without the hydrophilic polymer layer.

Independent of the relative surface roughness, the modified surface preferably has a relatively low surface roughness value. For example, the modified surface preferably has a global average $R_{rms}$ surface roughness of less than 500 nm. By way of further example, the modified surface may have a global average $R_{rms}$ surface roughness of less than 400 nm. By way of further example, the modified surface may have a global average $R_{rms}$ surface roughness of less than 300 nm. By way of further example, the modified surface may have a global average $R_{rms}$ surface roughness of less than 200 nm. By way of further example, the modified surface may have a global average $R_{rms}$ surface roughness of less than 150 nm. By way of further example, the modified surface may have a global average $R_{rms}$ surface roughness of less than 100 nm. By way of further example, the modified surface may have a global average $R_{rms}$ surface roughness of less than 75 nm. By way of further example, the modified surface may have a global average $R_{rms}$ surface roughness of less than 50 nm. By way of further example, the modified surface may have a global average $R_{rms}$ surface roughness of less than 25 nm. By way of further example, the modified surface may have a global average $R_{rms}$ surface roughness of less than 10 nm. By way of further example, the modified surface preferably has a global average $R_{rms}$ surface roughness of less than 5 nm. By way of further example, the modified surface preferably has a global average $R_{rms}$ surface roughness of less than 2 nm. By way of further example, the modified surface preferably has a global average $R_{rms}$ surface roughness of less than 1 nm. In a preferred embodiment, the hydrophilic polymer comprised by the modified surface in each of the foregoing examples recited in this paragraph is non-fouling. In one embodiment, the hydrophilic polymer comprised by the modified surface in each of the foregoing examples recited in this paragraph is a zwitterionic polymer. In one embodiment, the hydrophilic polymer comprised by the modified surface in each of the foregoing examples and embodiments recited in this paragraph is a polymer containing neutral hydrophilic pendant groups such as alkoxylated moieties. In one embodiment, the hydrophilic polymer comprised by the modified surface in each of the foregoing examples and embodiments recited in this paragraph is a polymer containing phosphorylcholine, carboxyammonium or sulfoammonium repeat units. In one embodiment, the hydrophilic polymer comprised by the modified surface in each of the foregoing examples and embodiments recited in this paragraph is a polymer containing sulfobetaine or carboxybetaine repeat units. In one embodiment, the hydrophilic polymer comprised by the modified surface in each of the foregoing examples and embodiments recited in this paragraph is a zwitterionic polymer and the zwitterionic polymer is grafted from a polyurethane polymer or copolymer. In one embodiment, the hydrophilic polymer comprised by the modified surface in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer comprised by the modified surface in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In one embodiment, the hydrophilic polymer layer may reduce the number of visual protrusions having a size greater than 0.1 micrometers relative to a reference substrate, that is, the same or an otherwise functionally equivalent catheter substrate lacking the non-fouling polymer layer. For example, the number of such visual protrusions may be reduced by at least 25%. By way of further example, the number of such visual protrusions may be reduced by at least 50%. By way of further example, the number of such visual protrusions may be reduced by at least 75%. By way of further example, the number of such visual protrusions may be reduced by at least 90%. In one embodiment, the hydrophilic polymer layer may reduce the number of visual protrusions having a size greater than 0.5 micrometers relative to a reference substrate, that is, the same or an otherwise functionally equivalent substrate lacking the non-fouling polymer layer. For example, the number of such visual protrusions may be reduced by at least 25%. By way of further example, the number of such visual protrusions may be reduced by at least 50%. By way of further example, the number of such visual protrusions may be reduced by at least 75%. By way of further example, the number of such visual protrusions may be reduced by at least 90.

Depending upon the catheter substrate to which the surface modification is being applied and its working environment, the hydrophilic polymer layer may have any of a wide range of thicknesses. For some applications, for example, the non-fouling polymer layer will have an Average Dry Thickness of at least about 50 nm. For some applications, substantially thicker hydrophilic polymer layers may be desirable. For example, the polymer layer may have an Average Dry Thickness of 50 micrometers. Typically, however, the polymer layer will have an average thickness that is less. For example, in some embodiments the polymer layer will have an Average Dry Thickness of up to 10 micrometers. By way of further example, in some embodiments the polymer layer will have an Average Dry Thickness in the range of about 100 nm to about 5,000 nm. By way of further example, in some embodiments the polymer layer will have an Average Dry Thickness in the range of about 300 nm to about 3,000 nm. By way of further example, in some embodiments the polymer layer will have an Average Dry Thickness in the range of about 500 nm to about 2,500 nm. By way of further example, in some embodiments the polymer layer will have an Average Dry Thickness of up to 1 micrometer. By way of further example, in some embodiments the polymer layer will have an Average Dry Thickness of up to 500 nm. By way of further example, in some embodiments the polymer layer will have an Average Dry Thickness in the range of about 100 nm to about 1,000 nm. By way of further example, in some embodiments the polymer layer will have an Average Dry Thickness in the range of about 300 nm to about 600 nm. By way of further example, in some embodiments the polymer layer will have an Average Dry Thickness in the range of about 200 nm to about 400 nm. In a preferred embodiment, the Average Dry Thickness of the polymer layer is determined using a scanning electron microscope (SEM) under vacuum or by analyzing the intensity of the chemical signals in the polymer layer, for instance, through the use of ATR-FTIR. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In general, the surface modification for a catheter component preferably has a relatively uniform thickness. For example, in one embodiment it is generally preferred that the standard deviation of the Average Dry Thickness of the hydrophilic polymer layer not exceed 100% of the Average Dry Thickness of the hydrophilic polymer layer. By way of further example, in one embodiment the standard deviation of the Average Dry Thickness of the hydrophilic polymer layer will not exceed 50% of the Average Dry Thickness of the hydrophilic polymer layer By way of further example, in one embodiment the standard deviation of the Average Dry Thickness of the hydrophilic polymer layer will not exceed 20% of the Average Dry Thickness of the hydrophilic polymer layer. By way of further example, in one embodiment the standard deviation of the Average Dry Thickness of the hydrophilic polymer layer will not exceed 10% of the Average Dry Thickness of the hydrophilic polymer layer. The standard deviation of the thickness is preferably determined by taking at least 5, and more preferably at least 6-10, randomly spaced measurements of the grafted polymer layer thickness. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In general, the surface modifications of the present invention are relatively hydrophilic. In general, the modified surface of a catheter substrate exhibits a static contact angle of less than 40 degrees. For example, modified surfaces of articles comprising hydrophilic polymeric materials of the present invention grafted from a relatively hydrophobic polymer such as silicone, hydrocarbon rubbers, fluorosilicones, fluoropolymers and other polymers having a native contact angle of at least 90 degrees may exhibit a static contact angle of less than 40 degrees. By way of further example, modified surfaces of articles comprising hydrophilic polymeric materials of the present invention grafted from a relatively hydrophobic substrate having a contact angle of at least 90 degrees may exhibit a static contact angle of less than 30 degrees. By way of further example, modified surfaces of articles comprising hydrophilic polymeric materials of the present invention grafted from a relatively hydrophobic substrate having a contact angle of at least 90 degrees may exhibit a static contact angle of less than 25 degrees. By way of further example, modified surfaces of articles having hydrophilic polymeric materials of the present invention grafted from a relatively hydrophobic substrate having a contact angle of at least 90 degrees may exhibit a static contact angle of less than 20 degrees. By way of further example, modified surfaces of articles having hydrophilic polymeric materials of the present invention grafted from a relatively hydrophobic substrate having a contact angle of at least 90 degrees may exhibit a static contact angle of less than 15 degrees. In a preferred embodiment, the hydrophilic polymer in each of the foregoing examples recited in this paragraph is hydrophilic. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

Catheters or components thereof having hydrophilic polymeric materials grafted from a less hydrophobic substrate such as polyurethane (including aliphatic polycarbonate-based polyurethanes) having a contact angle less than 90 degrees but greater than 25 degrees (without the surface modification) may exhibit a static contact angle of less than 25 degrees (with the surface modification). For example, in one embodiment modified surfaces of a catheter component having hydrophilic polymeric materials of the present invention grafted from a substrate having a contact angle of at least 25 degrees exhibit a static contact angle of less than 24 degrees. By way of further example, in one embodiment modified surfaces of catheter components having hydrophilic polymeric materials of the present invention grafted from a substrate having a contact angle of at least 25 degrees exhibit a static contact angle of less than 23 degrees. By way of further example, in one embodiment modified surfaces of catheter components having hydrophilic polymeric materials of the present invention grafted from a substrate having a contact angle of at least 25 degrees exhibit a static contact angle of less than 22 degrees. By way of further example, in one embodiment modified surfaces of catheter components having hydrophilic polymeric materials of the present invention grafted from a substrate having a contact angle of at least 25 degrees exhibit a static contact angle of less than 21 degrees. By way of further example, in one embodiment modified surfaces of catheter components having hydrophilic polymeric materials of the present invention grafted from a substrate having a contact angle of at least 25 degrees exhibit a static contact angle of less than 20 degrees. By way of further example, in one embodiment modified surfaces of catheter components having hydrophilic polymeric materials of the present invention grafted from a substrate having a contact angle of at least 25 degrees exhibit a static contact angle of less than 19 degrees. By way of further example, in one embodiment modified surfaces of catheter components having hydrophilic polymeric materials of the present invention grafted from a substrate having a contact angle of at least 25 degrees exhibit a static contact angle of less than 18 degrees. By way of further example, in one embodiment modified surfaces of catheter components having hydrophilic polymeric materials of the present invention grafted from a substrate having a contact angle of at least 25 degrees exhibit a static contact angle of less than 17 degrees. By way of further example, in one embodiment modified surfaces of catheter components having hydrophilic polymeric materials of the present invention grafted from a substrate having a contact angle of at least 25 degrees exhibit a static contact angle of less than 16 degrees. By way of further example, in one embodiment modified surfaces of catheter components having hydrophilic polymeric materials of the present invention grafted from a substrate having a contact angle of at least 25 degrees exhibit a static contact angle of less than 15 degrees. By way of further example, in one embodiment modified surfaces of articles having hydrophilic polymeric materials of the present invention grafted from a catheter component having a contact angle of at least 25 degrees exhibit a static contact angle of about 5 to about 15 degrees. In a preferred embodiment, the hydrophilic polymer in each of the foregoing examples recited in this paragraph is hydrophilic. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

Advantageously, the process of the present invention may be tuned to provide independent control of the thickness, the thickness uniformity, the degree of hydrophilicity (contact angle), and/or the swelling capacity of the grafted polymer layer, as well as the surface roughness of the surface-modified article, i.e., the catheter or one or more components thereof. Thus, for example, the process may be controlled to provide a catheter (or a component thereof) having a grafted polymer layer with an Average Dry Thickness that is at least 110% of the global average $R_{rms}$ surface roughness of the substrate, a standard deviation for the thickness of the hydrophilic polymer layer that does not exceed 100% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 200% of the Average Dry Thickness. By way of further example, the process may be controlled to provide a catheter component having a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 200% of the Average Dry Thickness. By way of further example, the process may be controlled to provide a catheter component having a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 100% of the Average Dry Thickness. By way of further example, the process may be controlled to provide a catheter component having a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 50% of the Average Dry Thickness. By way of further example, the process may be controlled to provide a catheter component having a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 25% of the Average Dry Thickness. By way of further example, the process may be controlled to provide a catheter component having a grafted polymer layer with a Average Dry Thickness that is at least 200% of the global average $R_{rms}$ surface roughness of the substrate, a standard deviation for the thickness of the hydrophilic polymer layer that does not exceed 20% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 25% of the Average Dry Thickness. By way of further example, the process may be controlled to provide a catheter component having a grafted polymer layer with a Average Dry Thickness that is at least 200% of the global average $R_{rms}$ surface roughness of the substrate, a standard deviation for the thickness of the hydrophilic polymer layer that does not exceed 10% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 25% of the Average Dry Thickness. By way of further example, the process may be controlled to provide a catheter component exhibiting a static contact angle of less than 25 degrees and a grafted polymer layer with an Average Dry Thickness that is at least 110% of the global average $R_{rms}$ surface roughness of the substrate, a standard deviation for the thickness of the hydrophilic polymer layer that does not exceed 100% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 200% of the Average Dry Thickness. By way of further example, the process may be controlled to provide a catheter component exhibiting a static contact angle of less than 25 degrees and a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 100% of the Average Dry Thickness. By way of further example, the process may be controlled to provide a catheter component exhibiting a static contact angle of less than 25 degrees and a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 50% of the Average Dry Thickness. By way of further example, the process may be controlled to provide a catheter component exhibiting a static contact angle of less than 25 degrees and a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 25% of the Average Dry Thickness. By way of further example, the process may be controlled to provide a catheter component exhibiting a static contact angle of less than 25 degrees and a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 10% of the Average Dry Thickness. By way of further example, the process may be controlled to provide a catheter component exhibiting a static contact angle of less than 25 degrees and a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 10% of the Average Dry Thickness. By way of further example, the process may be controlled to provide a catheter component exhibiting a static contact angle of less than 25 degrees and a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 5% of the Average Dry Thickness. By way of further example, the process may be controlled to provide a catheter component exhibiting a static contact angle of less than 25 degrees and a grafted polymer layer with an Average Dry Thickness that is at least 200% of the global average $R_{rms}$ surface roughness of the substrate, a standard deviation for the thickness of the hydrophilic polymer layer that does not exceed 50% of the Average Dry Thickness of the hydrophilic polymer layer, and a magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM) that is less than 5% of the Average Dry Thickness. By way of further example, in each of the foregoing examples, the grafted polymer layer may have an Average Dry Thickness in the range of 100 nm to 1,000 nm. By way of further example, in each of the foregoing examples, the polymer layer will have an Average Dry Thickness in the range of about 100 nm to about 5,000 nm. By way of further example, in each of the foregoing examples, the polymer layer will have an Average Dry Thickness in the range of about 300 nm to about 3,000 nm. By way of further example, in each of the foregoing examples, the polymer layer will have an Average Dry Thickness in the range of about 500 nm to about 2,500 nm.

In general, grafted polymeric material may be detected in a near-surface zone of the substrate using EDS mapping, XPS, or TOF-SIMS. The sample may be freeze fractured in liquid nitrogen to expose the coating/substrate interface. Fractured surface may then be coated with a thin layer of Au/Pt and observed under a scanning electron microscope with Energy Dispersive X-ray Analyser (EDAX) for element analysis. Suitable instruments include a FEI/Philips XL30 FEG ESEM. In order to assess if the polymeric material extends into the near-surface zone, at least 25, and preferably at least 50, representative locations spaced approximately evenly across the portion of the article carrying the grafted polymer layer should be analyzed to identify a detectable enhancement of polymeric material in the near-surface zone. For example, if a grafted polymer layer is applied to the indwelling portion of a catheter, the representative locations are approximately evenly spaced across the indwelling portion of the catheter. It is preferred to measure the thickness at representative points across the longest dimension of the portion of the article that is covered with the grafted polymer layer.

As described in greater detail elsewhere herein, incorporation of initiator into the substrate (i.e., a catheter or one or more components thereof) enables polymeric material to be grafted from surface and from within near-surface zone of the substrate. In general, however, it is preferred that polymeric material not extend too far into the substrate; thus, in one embodiment polymeric material is present in the near-surface zone but not at greater depths, i.e., not in the bulk. The maximum depth to which near-surface zone extends is, at least in part, a function of the initiator and the technique used to incorporate initiator in the substrate. Typically, however, it is generally preferred that lower boundary of the near-surface zone not be greater than 20 micrometers from the substrate surface as measured in a direction normal to the surface. By way of example, the lower boundary may not be greater than 15 micrometers from the substrate surface as measured in a direction normal to the surface. By way of further example, the lower boundary may not be greater than 10 micrometers from the substrate surface as measured in a direction normal to the surface. Similarly, the minimum depth of near-surface zone, i.e., the distance of the upper boundary from the substrate surface is, at least in part, also a function of the initiator and the technique used to incorporate initiator in the substrate. Typically, however, the upper boundary will be at least 0.1 micrometers from the substrate surface as measured in a direction normal to the surface. By way of example, the upper boundary may be at least 0.2 micrometers from the substrate surface as measured in a direction normal to the surface. By way of further example, the upper boundary may be at least 0.3 micrometers from the substrate surface as measured in a direction normal to the surface.

Referring to FIG. 1, a central venous catheter 10 in accordance with one embodiment of the present invention includes a catheter body 12 containing one or more lumens (not shown), a juncture hub 14 containing one or more lumens (not shown) connected to and in fluid communication with a respective catheter body lumen, extension line(s) 16, each containing a lumen (not shown) connected to and in fluid communication with a respective juncture hub lumen, and connector(s) 18 containing a lumen (not shown) connected to and in fluid communication with a respective extension line lumen. To permit a fluid to be administered to or removed from a patient, a lumen in the catheter tube is connected, in series, to a respective lumen in the juncture hub, extension line and connector.

Catheter body 12 will generally contain one to six lumens and a corresponding number of extension line(s) 16 and connector(s) 18. Juncture hub 14 includes a number of lumens, with the number corresponding to the number of lumens comprised by catheter body 12; each juncture hub lumen also has a distal end at the junction between juncture hub 14 and catheter body 12 and a proximal end at the junction between juncture hub 14 and an extension line 16. Similarly, each extension line 16 comprises a lumen having a distal end at the junction between the extension line and juncture hub 14 and a proximal end at the junction between the extension line and a connector 18. Each connector also comprises a lumen having a distal end at the junction between the connector and an extension line 16 and a proximal end at the opposite end thereof. As illustrated in FIG. 1, the distal end of extension line 16 and the proximal end of catheter body 12 appear to abut juncture hub 14; in certain embodiments, however, extension line 16 and catheter body 12 may extend a short distance into juncture hub 14 such that the distal end of extension line 16 and the proximal end of catheter body 12 is located within juncture hub 14.

Catheter body 12 will typically have a round or oval cross-sectional shape with an outer diameter ranging from 1 French (0.3 mm) to 16 French (5.4 mm). The lumen(s) within catheter body 12 may have any of a range of cross-sectional geometrical shapes (e.g., circular, oval, semi-circular, rectangular, triangular, trapezoidal, or crescent) and will typically have a cross-sectional surface area equivalent to that of a 0.1 mm diameter circle to a 5.0 mm diameter circle. The lumens may terminate at the distal end of the catheter body or at various points along the length of the catheter body between the proximal and distal ends of the catheter body. Additionally, catheter body 12 may taper from the proximal to the distal end with the outer diameter at the proximal end commonly being 125% to 300% of the outer diameter of the catheter body at the distal end.

Figure 2:
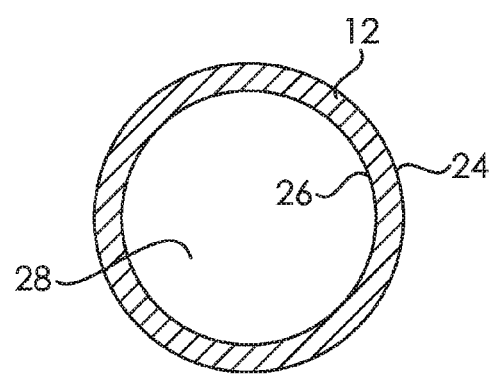
FIG. 2 is a cross-sectional view of the catheter of FIG. 1 taken along line 2-2.

In accordance with the present invention, the intraluminal and external surfaces of catheter 10, or at least one or more of the surfaces of the catheter components that are designed to be placed within a human body, to contact the bloodstream or to introduce a fluid to or withdraw a fluid from a patient are preferably modified with a hydrophilic polymer to reduce microbial contamination and thrombus attachment. Thus, for example, and referring now to FIG. 2, catheter body 12 has an exterior surface 24 and a lumen 28 extending from catheter body proximal end 23 to catheter body distal end 25 (See FIG. 1). Lumen 28 has intraluminal surface 26 (See FIG. 2). In one embodiment the exterior surface 24 and intraluminal surface 26 are modified with a hydrophilic polymer with the surface modification extending substantially from catheter body distal end 11 to catheter body proximal end 13 (See FIG. 1). By way of further example, in one embodiment the exterior surface of the juncture hub and the intraluminal surface(s) of the juncture hub lumen(s) (not shown in FIG. 1 or 2) are modified with a hydrophilic polymer with the surface modification extending substantially from juncture hub proximal end 19 to juncture hub distal end 21. By way of further example, in one embodiment the exterior surface of the extension line(s) or the intraluminal surface(s) of the extension line lumen(s) (not shown in FIG. 1 or 2) are modified with a hydrophilic polymer with the surface modification extending substantially from juncture hub proximal end 15 to juncture hub distal end 17. By way of further example, in one embodiment the exterior surface of the extension line(s) or the intraluminal surface(s) of the extension line lumen(s) (not shown in FIG. 1 or 2) are modified with a hydrophilic polymer with the surface modification extending substantially from juncture hub proximal end 15 to juncture hub distal end 17. By way of further example, in one embodiment the exterior surface of the connector(s) 18 (e.g., luer hubs) and the intraluminal surface(s) of the connector lumen(s) (not shown in FIG. 1 or FIG. 2) are modified with a hydrophilic polymer with the surface modification extending substantially from extension line proximal end(s) 11 to extension line distal end(s) 13. By way of further example, in one embodiment the exterior surface of the connector(s) 18 (e.g., luer hubs) or the intraluminal surface(s) of the connector lumen(s) (not shown in FIG. 1 or FIG. 2) are modified with a hydrophilic polymer with the surface modification extending substantially from extension line proximal end(s) 11 to extension line distal end(s) 13. By way of further example, In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer. In general, the hydrophilic polymer surface modification, where present, is preferably relatively thick, conformal and substantially uniform as further described herein.

The catheter body may be fabricated from any of a range of biocompatible polymers. For example, in certain embodiments the catheter body may be comprised of thermoplastic polyurethanes ("TPU"), thermoplastic polyurethane-silicones, silicones, or a combination thereof. Exemplary polyurethanes include Lubrizol Tecothane®, Lubrizol Carbothane®, Lubrizol Tecoflex®, Lubrizol Pellethane®, Lubrizol Estane®, Bayer Desmopan®, Bayer Texin®, DSM Bionate®, DSM Biospan®, DSM Bionate® II, DSM Elasthane®, BASF Elastollan™, Biomerics Quadrathane™, Biomerics Quadraflex™' Biomerics Quadraphilic™, or a blend thereof, in a range of hardnesses from 100A to 80A durometer. Alternatively, exemplary polyurethanes will have a range of hardnesses from 70A to 72D. Exemplary polyurethane-silicones include AorTech Elast-Eon™, AorTech ECSiI™, DSM CarboSil®, DSM Pursil®, or a blend thereof in a range of hardnesses from 80A to 60D durometer. Alternatively, exemplary polyurethane-silicones will have a range of hardnesses from 70A to 72D. Exemplary silicones include peroxide-cured and platinum cured silicones in a range of hardnesses from 50A to 60D durometer. Alternatively, exemplary silicones will have a range of hardnesses from 50A to 70D. Additionally, the biocompatible polymer may optionally contain a radiopacifier such as barium sulfate, bismuth trioxide, bismuth subcarbonate, bismuth oxychloride, tungsten, or tantalum, or a combination thereof. If included, the radiopacifier will typically be added at 5 wt % to 40 wt %. Colorants may also be included in the biocompatible polymer and the catheter body would then be opaque.

The juncture hub facilitates attachment of the catheter to the patient and provides a means of connecting each of the lumen(s) of the catheter body to individual extension line(s). The juncture hub contains within its construction a number of round or oval lumens corresponding in number to that of the number of lumens of the catheter body with the size and shape of the juncture hub determined by the number of lumens, lumen size, and outer diameter of the extension lines.

The extension line(s) are typically round or oval tubes with a single lumen having an inner diameter that is typically at least as great as the equivalent inner diameter (i.e., the diameter of a lumen assuming it is round based on the cross-sectional area of the lumen) of the corresponding lumen in the catheter body to which is connected. The extension line inner diameter may be up to ten times larger than that of the inner diameter of the corresponding lumen equivalent inner diameter (i.e., the diameter of a lumen assuming it is round based on the cross-sectional area of the lumen) in the catheter body to which it is connected. The outer diameter of an extension line will typically be 105% to 300% of the inner diameter of the extension line and be 1 cm to 20 cm in length.

The juncture hub and extension lines may also be fabricated from any of a range of biocompatible polymers. For example, in certain embodiments they may independently comprise thermoplastic polyurethanes, thermoplastic polyurethane-silicones, silicone or a combination thereof. Exemplary polyurethanes include Lubrizol Tecothane®, Lubrizol Carbothane®, Lubrizol Tecoflex®, Lubrizol Pellethane®, Lubrizol Estane®, Bayer Desmopan®, Bayer Texin®, DSM Bionate®, DSM Biospan®, DSM Bionate® II, DSM Elasthane®, BASF Elastollan™, Biomerics Quadrathane™, Biomerics Quadraflex™, Biomerics Quadraphilic™, or a blend thereof, in a range of hardnesses 100A to 80A durometer. Alternatively, exemplary polyurethanes will have a range of hardnesses from 70A to 72D durometer. Exemplary polyurethane-silicones include AorTech Elast-Eon™, AorTech ECSiI™, DSM CarboSil®, DSM Pursil®, or a blend thereof in a range of hardnesses from 80A to 60D durometer. Alternatively, exemplary polyurethane-silicones will have a range of hardnesses from 70A to 72D durometer. Exemplary silicones include peroxide-cured and platinum cured silicones in a range of hardnesses from 50A to 60D durometer. Alternatively, exemplary silicones will have a range of hardnesses from 50A to 70D durometer The juncture hub may be transparent, translucent, or opaque, and colorants may be added. The extension lines will typically be transparent or translucent, but colorants may be added. The connectors, preferably luer hubs, allow the independent connection of each catheter lumen to various medical devices by means of a standardized press fit or threaded juncture as described in ISO 594-1 and ISO 594-2. The inner diameter of the luer hub will typically be the same as the inner diameter of the attached extension line, except for the most proximal portion of the connector where the shape and size of the lumen is defined by ISO 594-1 and ISO 594-2. The connectors may be fabricated from one or more types/grades of rigid engineering thermoplastic polymers such as TPU, polyvinyl chloride, and polyetherimide, in a range of hardnesses from 100A to 75D durometer. The connectors can be fabricated from thermoplastic polyurethanes, polyetherimide, or polyvinyl chloride. Exemplary polyurethanes include Biomerics Quadraplast™, Lubrizol Tecoplast®, Lubrizol Isoplast®, Bayer Texin®, or SABIC Ultem® or a blend thereof in a range of hardnesses from 100A to 75D durometer. The connector may be transparent, translucent, or opaque, and colorants may be added. In one preferred embodiment the catheter body, juncture hub and extension lines of a catheter are fabricated from one or more aliphatic polyether thermoplastic polyurethanes (TPUs) and the connectors are made from one or more rigid aromatic TPUs. In one preferred embodiment the catheter body and juncture hub are fabricated from one or more aliphatic polyether thermoplastic polyurethanes (TPUs), the extension lines of a catheter are fabricated from one or more aromatic polyether thermoplastic polyurethanes TPUs and the connectors are made from one or more rigid aromatic TPUs. In one preferred embodiment the catheter body and juncture hub are fabricated from one or more aliphatic polyether thermoplastic polyurethanes (TPUs), the extension lines of a catheter are fabricated from one or more aromatic polyether thermoplastic polyurethanes TPUs and the connectors are made from one or more rigid PVCs. In one preferred embodiment the catheter body and juncture hub are fabricated from one or more aliphatic polyether thermoplastic polyurethanes (TPUs), the extension lines of a catheter are fabricated from one or more aromatic polyether thermoplastic polyurethanes TPUs and the connectors are made from one or more rigid polyetherimides (PEIs). In one preferred embodiment the catheter body is fabricated from one or more aliphatic polyether thermoplastic polyurethane (TPU), the juncture hub and extension lines are fabricated from one or more aromatic polyether thermoplastic polyurethanes (TPUs) and the connectors are made from one or more rigid aromatic TPUs. In one preferred embodiment the catheter body is fabricated from one or more aliphatic polyether thermoplastic polyurethane (TPU), the juncture hub and extension lines are fabricated from one or more aromatic polyether thermoplastic polyurethanes (TPUs) and the connectors are made from one or more rigid PVCs. In one preferred embodiment the catheter body is fabricated from one or more aliphatic polyether thermoplastic polyurethane (TPU), the juncture hub and extension lines are fabricated from one or more aromatic polyether thermoplastic polyurethanes (TPUs) and the connectors are made from one or more polyetherimides. In one preferred embodiment the catheter body and extension lines of a catheter are fabricated from one or more aromatic polyether thermoplastic polyurethanes (TPUs), the juncture hub is fabricated from one or more aliphatic polyether thermoplastic polyurethanes (TPUs) and the connectors are made from one or more rigid aromatic TPUs. In one preferred embodiment the catheter body, juncture hub and extension lines of a catheter are fabricated from one or more aromatic polyether thermoplastic polyurethanes (TPUs) and the connectors are made from one or more rigid aromatic TPUs. In another preferred embodiment the catheter body, juncture hub and extension lines of a catheter are fabricated from one or more aromatic polyether TPUs and the connectors are made from one or more grades of rigid PVC. In another preferred embodiment the catheter body and juncture hub are fabricated from one or more aliphatic polycarbonate TPUs, the extension lines are made from one or more aromatic polyether TPUs and the connectors are fabricated from one or more rigid aromatic TPUs. In another preferred embodiment the catheter body and juncture hub are fabricated from one or more aliphatic polycarbonate TPUs, the extension lines are made from one or more aromatic polyether TPUs and the connectors are fabricated from one or more grades of rigid PVC. In another preferred embodiment the catheter body and juncture hub are fabricated from one or more aliphatic polycarbonate TPUs, the extension lines are made from one or more aromatic polyether TPUs and the connectors are fabricated from one or more grades of polyetherimide. In one preferred embodiment the catheter body, juncture hub and extension lines of a catheter are fabricated from one or more peroxide or platinum cured silicones and the connectors are made from one or more rigid aromatic TPUs. In one preferred embodiment the catheter body, juncture hub and extension lines of a catheter are fabricated from one or more peroxide or platinum cured silicones and the connectors are made from one or more rigid PVCs. In one preferred embodiment the catheter body, juncture hub and extension lines of a catheter are fabricated from one or more peroxide or platinum cured silicones and the connectors are made from one or more rigid polyetherimides. In one preferred embodiment the catheter body and juncture hub of a catheter are fabricated from one or more peroxide or platinum cured silicones and the extension lines are fabricated from one or more aromatic polyether thermoplastic polyurethane and the connectors are made from one or more rigid aromatic TPUs. In one preferred embodiment the catheter body and juncture hub of a catheter are fabricated from one or more peroxide or platinum cured silicones and the extension lines are fabricated from one or more aliphatic polycarbonate thermoplastic polyurethane and the connectors are made from one or more rigid aromatic TPUs. In one preferred embodiment the catheter body and juncture hub of a catheter are fabricated from one or more peroxide or platinum cured silicones and the extension lines are fabricated from one or more aliphatic polyether thermoplastic polyurethane and the connectors are made from one or more rigid aromatic TPUs. In one embodiment a catheter has a Tecothane® catheter body and juncture hub with Pellethane® extension lines and Isoplast® luer hub connectors. In one embodiment a catheter has a Tecothane® catheter body and Tecoflex® juncture hub with Pellethane® extension lines and Isoplast® luer hub connectors. In another embodiment a catheter has a Tecothane® catheter body and juncture hub with Pellethane® extension lines and luer hub connectors. In one embodiment a catheter has a Tecothane® catheter body and Pellethane® juncture hub and extension lines and Isoplast® luer hub connectors. In another embodiment a catheter has a Tecothane® catheter body and juncture hub with Tecoflex® extension lines and Isoplast® luer hub connectors. In another embodiment a catheter has a Tecothane® catheter body and juncture hub with silicone extension lines and PVC connectors. In another embodiment a catheter has a Tecothane® catheter body and juncture hub with silicone extension lines and polyetherimide (Ultem®) luer hub connectors. In another embodiment a catheter has a Tecothane® catheter body and juncture hub with silicone extension lines and polycarbonate (Lexan®, Makrolon®) luer hub connectors.

In one embodiment a catheter has a Quadrathane™ catheter body and juncture hub with Pellethane® extension lines and Isoplast® luer hub connectors. In one embodiment a catheter has a Quadrathane™ catheter body and juncture hub with Pellethane® extension lines and Quadraplast™ luer hub connectors. In one embodiment a catheter has a Quadrathane™ catheter body, juncture hub, and extension lines and Isoplast® luer hub connectors. In one embodiment a catheter has a Quadrathane™ catheter body, extension lines and Quadraflex™ juncture hub and Quadraplast™ luer hub connectors. In one embodiment a catheter has a Quadrathane™ catheter body, Quadraflex™ extension lines and juncture hub and Quadraplast™ luer hub connectors. In one embodiment a catheter has a Quadrathane™ catheter body and Tecoflex® juncture hub with Pellethane® extension lines and Isoplast® luer hub connectors. In another embodiment a catheter has a Quadrathane™ catheter body and juncture hub with Pellethane® extension lines and luer hub connectors. In one embodiment a catheter has a Quadrathane™ catheter body and Pellethane® juncture hub and extension lines and Isoplast® luer hub connectors. In another embodiment a catheter has a Quadrathane™ catheter body and juncture hub with Tecoflex® extension lines and Isoplast® luer hub connectors. In another embodiment a catheter has a Quadrathane™ catheter body and juncture hub with silicone extension lines and PVC connectors. In another embodiment a catheter has a Quadrathane™ catheter body and juncture hub with silicone extension lines and polyetherimide (Ultem®) luer hub connectors. In another embodiment a catheter has a Quadrathane™ catheter body and juncture hub with silicone extension lines and polycarbonate (Lexan®, Makrolon®) luer hub connectors.

In one embodiment a catheter has a Quadraflex™ catheter body and juncture hub with Pellethane® extension lines and Isoplast® luer hub connectors. In one embodiment a catheter has a Quadraflex™ catheter body and Tecoflex® juncture hub with Pellethane® extension lines and Isoplast® luer hub connectors. In another embodiment a catheter has a Quadraflex™ catheter body and juncture hub with Pellethane® extension lines and luer hub connectors. In one embodiment a catheter has a Quadraflex™ catheter body and Pellethane® juncture hub and extension lines and Isoplast® luer hub connectors. In another embodiment a catheter has a Quadraflex™ catheter body and juncture hub with Tecoflex® extension lines and Isoplast® luer hub connectors. In another embodiment a catheter has a Quadraflex™ catheter body and juncture hub with silicone extension lines and PVC connectors. In another embodiment a catheter has a Quadraflex™ catheter body and juncture hub with silicone extension lines and polyetherimide (Ultem®) luer hub connectors. In another embodiment a catheter has a Quadraflex™ catheter body and juncture hub with silicone extension lines and polycarbonate (Lexan®, Makrolon®) luer hub connectors.

In another embodiment a catheter has a Carbothane® catheter body and juncture hub with Pellethane® extension lines and Isoplast® luer hub connectors. In another embodiment a catheter has a Carbothane® catheter body, Tecoflex® juncture hub with Pellethane® extension lines and Isoplast® luer hub connectors. In another embodiment a catheter has a Carbothane® catheter body, Tecothane® juncture hub with Pellethane® extension lines and Isoplast® luer hub connectors. In another embodiment a catheter has a Carbothane® catheter body and juncture hub with Pellethane® extension lines and luer hub connectors. In another embodiment a catheter has a Carbothane® catheter body and juncture hub with Tecoflex® extension lines and Isoplast® luer hub connectors. In another embodiment a catheter has a Carbothane® catheter body and juncture hub with silicone extension lines and PVC luer hub connectors. In another embodiment a catheter has a Carbothane® catheter body and juncture hub with silicone extension lines and polyetherimide (Ultem®) luer hub connectors. In another embodiment a catheter has a Carbothane® catheter body and juncture hub with silicone extension lines and polycarbonate (Lexan®, Makrolon®) luer hub connectors.

In another embodiment a catheter has a Texin® catheter body, Tecoflex® juncture hub with Pellethane® extension lines and Isoplast® luer hub connectors. In another embodiment a catheter has a Texin® catheter body, Tecothane® juncture hub with Pellethane® extension lines and Isoplast® luer hub connectors. In another embodiment a catheter has a Texin® catheter body and juncture hub with Pellethane® extension lines and luer hub connectors. In another embodiment a catheter has a Texin® catheter body and juncture hub with Tecoflex® extension lines and Isoplast® luer hub connectors. In another embodiment a catheter has a Texin® catheter body and juncture hub with Pellethane® extension lines and Isoplast® luer hub connectors. In another embodiment a catheter has a Texin® catheter body and juncture hub with silicone extension lines and PVC luer hubs. In another embodiment a catheter has a Texin® catheter body and juncture hub with silicone extension lines and polyetherimide (Ultem®) luer hub connectors. In another embodiment a catheter has a Texin® catheter body and juncture hub with silicone extension lines and polycarbonate (Lexan®, Makrolon®) luer hub connectors.

In another embodiment a catheter has a Tecoflex® catheter body and juncture hub with Pellethane® extension lines and Isoplast® luer hub connectors. In another embodiment a catheter has a Tecoflex® catheter body and juncture hub with Pellethane® extension lines and luer hub connectors. In another embodiment a catheter has a Tecoflex® catheter body and juncture hub with Tecoflex® extension lines and Isoplast® luer hub connectors. In another embodiment a catheter has a Tecoflex® catheter body and juncture hub with Pellethane® extension lines and Isoplast® luer hub connectors. In another embodiment a catheter has a Tecoflex® catheter body and juncture hub with silicone extension lines and PVC luer hub connectors. In another embodiment a catheter has a Tecoflex® catheter body and juncture hub with silicone extension lines and polyetherimide (Ultem®) luer hub connectors. In another embodiment a catheter has a Tecoflex® catheter body and juncture hub with silicone extension lines and polycarbonate (Lexan®, Makrolon®) luer hub connectors.

In another embodiment a catheter has a Pellethane® catheter body, juncture hub, and extension lines and Isoplast® luer hub connectors. In another embodiment a catheter has a Pellethane® catheter body and juncture hub with Tecoflex® extension lines and Isoplast® luer hub connectors. In another embodiment a catheter has a Pellethane® catheter body and extension lines and Tecothane® juncture hub and Isoplast® luer hub connectors. In another embodiment a catheter has a Pellethane® catheter body and extension lines and Tecothane® juncture hub and polyetherimide (Ultem®) luer hub connectors. In another embodiment a catheter has a Pellethane® catheter body and extension lines and Tecothane® juncture hub and PVC luer hub connectors. In another embodiment a catheter has a Pellethane® catheter body, Tecoflex® juncture hub and extension lines and Isoplast® luer hub connectors. In another embodiment a catheter has a Pellethane® catheter body and juncture hub with silicone extension lines and PVC luer hub connectors. In another embodiment a catheter has a Pellethane® catheter body and juncture hub with silicone extension lines and polyetherimide (Ultem®) luer hub connectors. In another embodiment a catheter has a Pellethane® catheter body and juncture hub with silicone extension lines and polycarbonate (Lexan®, Makrolon®) luer hub connectors.

In another embodiment a catheter has a PurSil® catheter body and juncture hub with Pellethane® extension lines and Isoplast® luer hub connectors. In another embodiment a catheter has a PurSil® catheter body and juncture hub with Pellethane® extension lines and luer hub connectors. In another embodiment a catheter has a PurSil® catheter body and juncture hub with Tecoflex® extension lines and Isoplast® luer hub connectors. In another embodiment a catheter has a PurSil® catheter body and juncture hub with Pellethane® extension lines and Isoplast® luer hub connectors. In another embodiment a catheter has a PurSil® catheter body and Tecoflex® juncture hub and extension lines and Isoplast® luer hub connectors. In another embodiment a catheter has a PurSil® catheter body and Tecothane® juncture hub with Pellethane® extension lines and Isoplast® luer hub connectors. In another embodiment a catheter has a PurSil® catheter body and juncture hub with Tecoflex® extension lines and Isoplast® luer hub connectors. In another embodiment a catheter has a PurSil® catheter body and Tecothane® juncture hub with Tecoflex® extension lines and Isoplast® luer hub connectors. In another embodiment a catheter has a PurSil® catheter body and juncture hub with Pellethane® extension lines and polyetherimide (Ulteml®) luer hub connectors. In another embodiment a catheter has a PurSil® catheter body and juncture hub with Pellethane® extension lines and PVC luer hub connectors. In another embodiment a catheter has a PurSil® catheter body and juncture hub with silicone extension lines and PVC luer hub connectors. In another embodiment a catheter has a PurSil® catheter body and juncture hub with silicone extension lines and polyetherimide (Ultem®) luer hub connectors. In another embodiment a catheter has a PurSil® catheter body and juncture hub with silicone extension lines and polycarbonate (Lexan®, Makrolon®) luer hub connectors.

In another embodiment a catheter has a Biospan® catheter body and juncture hub with Pellethane® extension lines and Isoplast® luer hub connectors. In another embodiment a catheter has a Biospan® catheter body and juncture hub with Pellethane® extension lines and luer hub connectors. In another embodiment a catheter has a Biospan® catheter body and juncture hub with Tecoflex® extension lines and Isoplast® luer hub connectors. In another embodiment a catheter has a Biospan® catheter body and Tecoflex® juncture hub and extension lines and Isoplast® luer hub connectors. In another embodiment a catheter has a Biospan® catheter body and Tecothane® juncture hub with Pellethane® extension lines and Isoplast® luer hub connectors. In another embodiment a catheter has a Biospan® catheter body and juncture hub with Tecoflex® extension lines and Isoplast® luer hub connectors. In another embodiment a catheter has a Biospan® catheter body and Tecothane® juncture hub with Tecoflex® extension lines and Isoplast® luer hub connectors. In another embodiment a catheter has a Biospan® catheter body and juncture hub with Pellethane® extension lines and polyetherimide (Ulteml®) luer hub connectors. In another embodiment a catheter has a Biospan® catheter body and juncture hub with Pellethane® extension lines and PVC luer hub connectors. In another embodiment a catheter has a Biospan® catheter body and juncture hub with Pellethane® extension lines and Isoplast® luer hub connectors. In another embodiment a catheter has a Biospan® catheter body and juncture hub with silicone extension lines and PVC luer hub connectors. In another embodiment a catheter has a Biospan® catheter body and juncture hub with silicone extension lines and polyetherimide (Ultem®) luer hub connectors. In another embodiment a catheter has a Biospan® catheter body and juncture hub with silicone extension lines and polycarbonate (Lexan®, Makrolon®) luer hub connectors.

In another embodiment a catheter has a Bionate® catheter body and juncture hub with Pellethane® extension lines and Isoplast® luer hubs. In another embodiment a catheter has a Bionate® catheter body and juncture hub with Pellethane® extension lines and luer hub connectors. In another embodiment a catheter has a Bionate® catheter body and juncture hub with Tecoflex® extension lines and Isoplast® luer hub connectors. In another embodiment a catheter has a Bionate® catheter body and Tecoflex® juncture hub and extension lines and Isoplast® luer hub connectors. In another embodiment a catheter has a Bionate® catheter body and Tecothane® juncture hub with Pellethane® extension lines and Isoplast® luer hub connectors. In another embodiment a catheter has a Bionate® catheter body and juncture hub with Tecoflex® extension lines and Isoplast® luer hub connectors. In another embodiment a catheter has a Bionate® catheter body and Tecothane® juncture hub with Tecoflex® extension lines and Isoplast® luer hub connectors. In another embodiment a catheter has a Bionate® catheter body and juncture hub with Pellethane® extension lines and polyetherimide (Ulteml®) luer hub connectors. In another embodiment a catheter has a Bionate® catheter body and juncture hub with Pellethane® extension lines and PVC luer hub connectors. In another embodiment a catheter has a Bionate® catheter body and juncture hub with Pellethane® extension lines and Isoplast® luer hub connectors. In another embodiment a catheter has a Bionate® catheter body and juncture hub with silicone extension lines and PVC luer hub connectors. In another embodiment a catheter has a Bionate® catheter body and juncture hub with silicone extension lines and polyetherimide (Ultem®) luer hub connectors. In another embodiment a catheter has a Bionate® catheter body and juncture hub with silicone extension lines and polycarbonate (Lexan®, Makrolon®) luer hub connectors.

In another embodiment a catheter has a silicone catheter body, juncture hub, and Pellethane® extension lines and Isoplast® luer hub connectors. In another embodiment a catheter has a silicone catheter body, juncture hub and Pellethane® extension lines and PVC luer hub connectors. In another embodiment a catheter has a silicone catheter body, juncture hub, and Pellethane® extension lines and polyetherimide (Ultem®) luer hub connectors. In another embodiment a catheter has a silicone catheter body, juncture hub, and Tecoflex® extension lines and Isoplast® luer hub connectors. In another embodiment a catheter has a silicone catheter body, juncture hub, and Quadraflex™ extension lines and Isoplast® luer hub connectors. In another embodiment a catheter has a silicone catheter body, juncture hub, and Quadraflex™ extension lines and Qudraplast™ luer hub connectors. In another embodiment a catheter has a silicone catheter body, juncture hub, and Tecoflex® extension lines and PVC luer hub connectors. In another embodiment a catheter has a silicone catheter body, juncture hub, and Quadraflex™ extension lines and PVC luer hub connectors. In another embodiment a catheter has a silicone catheter body, juncture hub, and Tecoflex® extension lines and polyetherimide (Ultem®) luer hub connectors. In another embodiment a catheter has a silicone catheter body, juncture hub, and Quadraflex™ extension lines and polyetherimide (Ultem®) luer hub connectors. In another embodiment a catheter has a silicone catheter body, juncture hub, and extension lines and PVC luer hub connectors. In another embodiment a catheter has a silicone catheter body, juncture hub, and extension lines and polyetherimide (Ultem®) luer hub connectors. In another embodiment a catheter has a silicone catheter body, juncture hub, and extension lines and polycarbonate (Lexan®, Makrolon®) connectors.

If not specifically stated in the proceeding paragraphs 139 to 147, polyvinyl chloride (PVC) or polyetherimide (PEI) may be used to fabricate the connectors instead of rigid aromatic thermoplastic polyurethane (Quadraplast™, Isoplast®, Tecoplast®).

Figure 3:
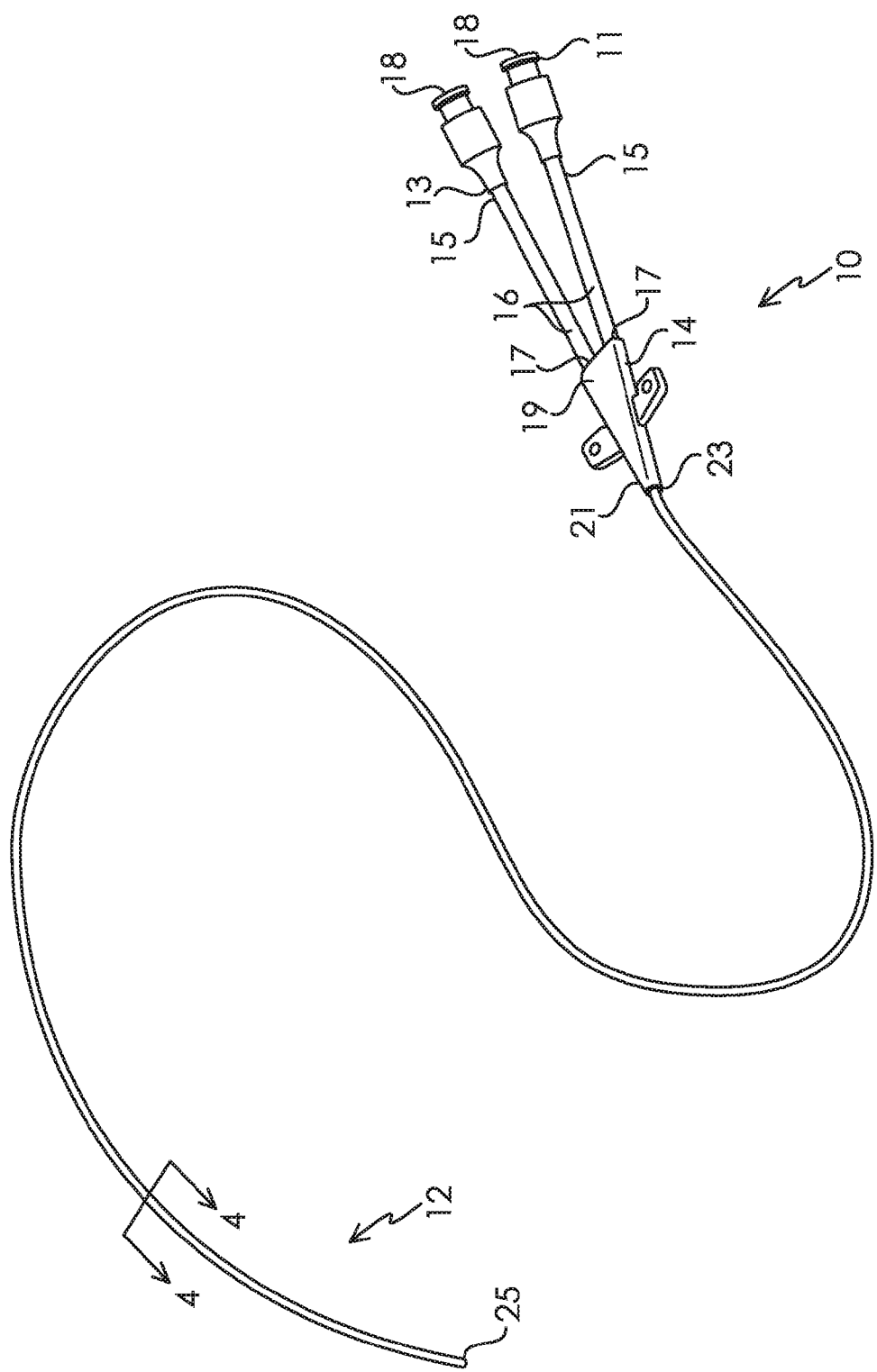
FIG. 3 is a perspective view of a peripherally inserted central catheter ("PICC") in accordance with one embodiment.

Referring now to FIG. 3, a peripherally inserted central catheter ("PICC") in accordance with one embodiment is illustrated. As illustrated, catheter 10 includes a catheter body 12 having proximal end 23 and distal end 25, defining two lumens 28 (see FIG. 4). A juncture hub 14 having juncture hub proximal end 19 and juncture hub distal end 21 is connected to catheter body proximal end 23 to interconnect the two lumens of catheter body 12 each to a respective one of two extension lines 16. Each extension line 16 is fitted with a luer connector 18. As illustrated in FIG. 3, the distal end of extension lines 16 and the proximal end of catheter body 12 appear to abut juncture hub 14; in certain embodiments, however, extension lines 16 and catheter body 12 may extend a short distance into juncture hub 14 such that the distal end of extension lines 16 and the proximal end of catheter body 12 is located within juncture hub 14.

Figure 4:
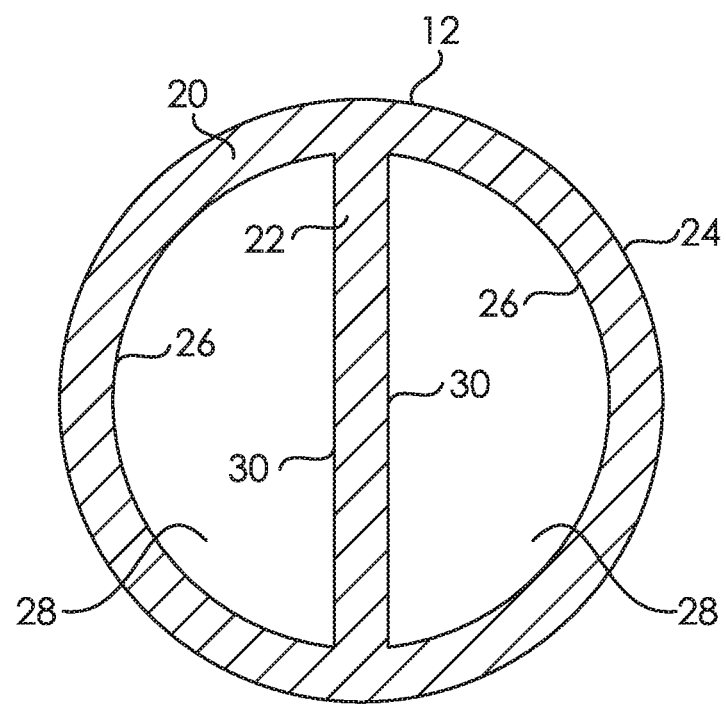
FIG. 4 is a cross-sectional view of the peripherally inserted central catheter of FIG. 3, taken along line 3-3.

Referring now to FIG. 4, catheter body 12 comprises catheter body wall 20 and septum 22. Lumens 28 are bounded by intraluminal surfaces 26 and 30, and extend from proximal end 23 to distal end 25 of the catheter body (See FIG. 3).

Catheter 10 and each of the components thereof (e.g., catheter body 12, juncture hub 14, extension lines 16 and luer connectors 18) may be made of any suitable biocompatible material. In one embodiment, for example, the component parts may independently comprise biocompatible polymer such as polyurethane or a copolymer thereof, a polyether or copolymer thereof, a polycarbonate or copolymer thereof, a polysilicone or a copolymer thereof. Additionally, the catheter body 12 may comprise barium sulfate or other radiopacifier. Typically, each of the component parts comprises a biocompatible material, but not necessarily the same material. Thus, for example, in one embodiment catheter body 12 may comprise polyurethane or a copolymer thereof, while one or more of juncture hub 14, extension lines 16 and luer connectors 18 comprise a different polyurethane (co)polymer or even a different polymer type relative to catheter body 12 and, in some embodiments, relative to each other.

In accordance with the present invention, the intraluminal and exterior surfaces of catheter 10, or at least one or more of the intraluminal and exterior surfaces of the catheter components that are designed to be placed within a human body, to contact the bloodstream or to introduce a fluid to or withdraw a fluid from a patient are preferably modified with a hydrophilic polymer to reduce microbial contamination and thrombus attachment. For example, in one embodiment the exterior surface 24 of catheter body wall 20 and intraluminal surfaces 26, 30 (see FIG. 4) comprise a hydrophilic, preferably non-fouling polymer surface modification having a thickness of least about 50 nm; preferably, the thickness is substantially uniform and conformal as described elsewhere herein. By way of further example, in one embodiment catheter body wall 20 and septum 22 comprise a polyurethane polymer (or copolymer) and one or more of juncture hub 14, extension lines 16 and luer connectors 18 comprise a different polymer relative to catheter body wall 20 and septum 22, and the exterior surfaces of each of these components and the lumens contained therein have been modified with a hydrophilic polymer grafted from the surface of the component. In each such instance, it is generally preferred that the thickness of the hydrophilic polymer be at least about 50 nm, and the surface modification will be substantially conformal and substantially uniform. By way of further example, in a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer, silicone, fluoronated polymer, polyvinyl chloride, polyetherimide, or polycarbonate. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer, silicone, fluoronated polymer, polyvinyl chloride, polyetherimide, or polycarbonate. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer, silicone, fluoronated polymer, polyvinyl chloride, polyetherimide, or polycarbonate.

As illustrated in FIG. 3, catheter 10 is a peripherally inserted central catheter ("PICC") and is but one embodiment of a catheter in accordance with the present invention; other types and configurations of catheters to establish vascular or other access to a catheter body of a patient can also benefit from the present disclosure and thus the principles of the present disclosure should not be limited to what is explicitly shown and described herein. It should be appreciated that many different configurations of the disclosed preferred embodiment are possible, including variations with regard to shape of the tubes, catheter materials and standard catheter features. For example, the distal tip portions of the catheter body could be shaped differently. In addition, the catheter body (and correspondingly the juncture hub) may contain one lumen and could be manufactured having different durometers or radiopacifiers to improve physical properties such as reducing kinking, minimizing wall thickness, or radiopacity (different radiopacity could be used, for example, to help a physician distinguish between arterial and venous tips when viewed under x-ray). In addition, the catheter body (and correspondingly the juncture hub) may contain three or more lumens and could be manufactured having different durometers or radiopacifiers to improve physical properties such as reducing kinking, minimizing wall thickness, or radiopacity (different radiopacity could be used, for example, to help a physician distinguish between arterial and venous tips when viewed under x-ray).

To tailor a catheter for a given medical procedure, a catheter tip may be subjected to a processing step comprising heating and bending, laser-cutting or the like to provide the catheter tip with a complex geometric shape, cut-out or both. See, for example, the dual lumen catheter tips depicted in FIGS. 5a-5f. As illustrated, the lumens may have non-coterminus distal ends (FIGS. 5a, 5c, 5d, and 5e). The lumen distal ends may be split (FIGS. 5c and 5d). The split lumen distal ends may also be curved with each of the lumens having a different center of curvature (FIGS. 5c and 5d). The walls of the catheter body may also be laser-cut or otherwise machined to introduce cut-outs or other complex geometric shapes (FIGS. 5b, 5e and 5f). In some embodiments such processing steps may provide the catheter body in the Tip Region with a radius of curvature of less than 10 cm. By way of further example, in some embodiments such processing steps may provide the catheter body in the Tip Region with a radius of curvature of less than 5 cm. By way of further example, in some embodiments such processing steps may provide the catheter body in the Tip Region with a radius of curvature of less than 2.5 cm. By way of further example, in some embodiments such processing steps may provide the catheter body in the Tip Region with a radius of curvature of less than 1 cm. By way of further example, in some embodiments such processing steps may provide the catheter body in the Tip Region with a radius of curvature of less than 0.5 cm. Such steps, however, may alter the chemical or physical properties of the Tip Region of the catheter tube relative to other parts of the catheter tube which, in turn, may affect the extent of modification of the surface by the zwitterionic polymer.

Figure 5A:
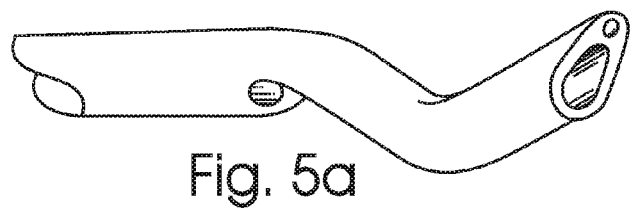
FIGS. 5a-5f are alternative configurations for the Tip Region of a dual lumen catheter in accordance with one embodiment.
Figure 5B:
Figure 5C:
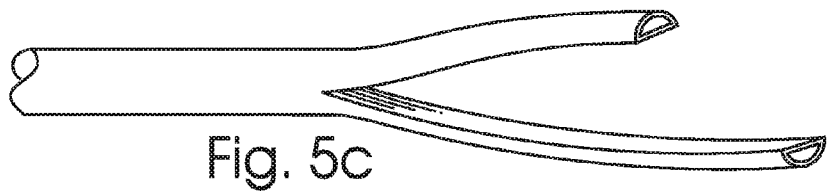
Figure 5D:
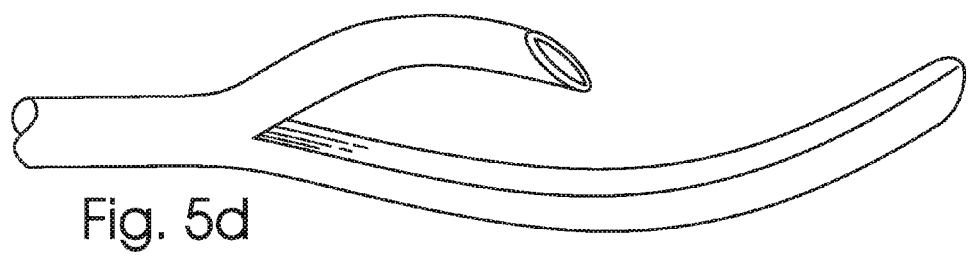
Figure 5E:
Figure 5F:
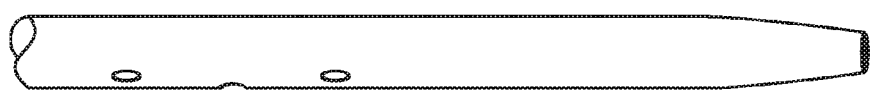

In a step-tip catheter, the Tip Region of which is shown in FIG. 5a, the outlet for one lumen at the distal end of the catheter body is at least 2 cm distal of the outlet for one or more additional lumens. In a split-tip catheter, as shown in FIGS. 5b and 5c, two or more lumens are surrounded by polymer walls that do not share a common wall or septum at some point within the Tip Region. Commonly, a split tip catheter may be created by separately extruding a DD catheter body and two individual D-shaped single lumen tip segments, and attaching the two tip segments to the body using heat. In a curved-tip catheter, the tip region of two embodiments of which are shown in FIGS. 5a and 5d, the tip region contains a molded shape that upon deployment in the body has a radius of curvature in the axial direction of the catheter of 0.25 to 2 inches (0.6 cm to 5 cm). Alternatively, as deployed in the body, a catheter may be considered to be a curved-tip catheter if any portion of the Tip Region extends at least 0.75 cm in a radial direction from the radial center of the catheter body.

In preferred embodiments, the Local Average Dry Thickness as determined for the Tip Region is at least 25% of the Average Dry Thickness as measured along the length of the lumen of that catheter component. For example, in one such embodiment the Local Average Dry Thickness as measured on the Tip Region is at least 50% of the Average Dry Thickness as measured along the length of the lumen of that catheter component. By way of further example, in one such embodiment the Local Average Dry Thickness as measured on the Tip Region is at least 80% of the Average Dry Thickness as measured along the length of the lumen of that catheter component. By way of further example, in one such embodiment the Local Average Dry Thickness as measured on the Tip Region is at least 90% of the Average Dry Thickness as measured along the length of the lumen of that catheter component. By way of further example, in one such embodiment the Local Average Dry Thickness as measured on the Tip Region is at least 95% of the Average Dry Thickness as measured along the length of the lumen of that catheter component.

Further, the Tip Region of catheters are particularly at risk for thrombus formation because of the disturbances to blood flow that may be created at the point of insertion into the vascular system during device use. To minimize the risk for thrombus formation, therefore, it is preferred that the zwitterionic polymer surface modification be relatively uniform and conformal. For example, in some embodiments, the Tip Region is Conformal at a level of 0.5 $mm^2$. By way for further example, in some embodiments, the Tip Region is Conformal at a level of 0.25 $mm^2$. By way for further example, in some embodiments, the Tip Region is Conformal at a level of 0.1 $mm^2$. By way for further example, in some embodiments, the Tip Region is Conformal at a level of 0.05 $mm^2$. By way of further example, in some embodiments the Tip Region is Conformal at a level of 0.01 $mm^2$. By way of further example, in some embodiments the Tip Region is Conformal at a level of 0.005 $mm^2$. By way of further example, in some embodiments the Tip Region is Conformal at a level of 0.001 $mm^2$.

In preferred embodiments, the above specifications for Tip Region thickness or conformality are achieved for a step-tip hemodialysis catheter. In preferred embodiments, the above specifications for Tip Region thickness or conformality are achieved for a step-tip hemodialysis catheter. In preferred embodiments, the above specifications for Tip region thickness or conformality are achieved for a step-tip hemodialysis catheter. In preferred embodiments, the above specifications for Tip Region thickness or conformality are achieved for a curved-tip hemodialysis catheter.

In accordance with one embodiment, it is generally preferred that the exterior surfaces of the catheter 10, as well as the luminal surfaces of catheter body 12, juncture hub 14, extension line(s) 16 and connector(s) 18, as well as any other exterior and intraluminal surfaces of catheter 10 that may contact fluid administered to or withdrawn from a patient be modified with a graft-from hydrophilic polymer preferably having an Average Dry Thickness of at least about 50 nm. For some catheter components, substantially thicker grafted polymer layers may be desirable. For example, the grafted hydrophilic polymer layer may have an Average Dry Thickness of 50 micrometers. Typically, however, the grafted hydrophilic polymer layer will have an average thickness that is less. For example, in some embodiments the grafted hydrophilic polymer layer will have an Average Dry Thickness of up to 10 micrometers. By way of further example, in some embodiments the grafted hydrophilic polymer layer will have an Average Dry Thickness of up to 1 micrometer. By way of further example, in some embodiments the grafted hydrophilic polymer layer will have a Average Dry Thickness of up to 500 nm. By way of further example, in some embodiments the grafted hydrophilic polymer layer will have an Average Dry Thickness in the range of about 100 nm to about 1,000 nm. By way of further example, in some embodiments the grafted hydrophilic polymer layer will have an Average Dry Thickness in the range of about 200 nm to about 700 nm. By way of further example, in some embodiments the grafted hydrophilic polymer layer will have an Average Dry Thickness in the range of about 300 nm to about 600 nm. By way of further example, in some embodiments the grafted hydrophilic polymer layer will have an Average Dry Thickness in the range of about 100 nm to about 5,000 nm. By way of further example, in some embodiments the grafted hydrophilic polymer layer will have an Average Dry Thickness in the range of about 300 nm to about 3,000 nm. By way of further example, in some embodiments the grafted hydrophilic polymer layer will have an Average Dry Thickness in the range of about 500 nm to about 2,500 nm. In a preferred embodiment, the Average Dry Thickness of the grafted polymer layer is determined using a scanning electron microscope (SEM) under vacuum or by analyzing the intensity of the chemical signals in the polymer layer, for instance, through the use of ATR-FTIR. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

Nearly all hemodialysis catheters are of a dual lumen design, where the inner diameter of round or oval catheter body is divided equally between and arterial (inlet) and venous (outlet) lumen. The lumens of the catheter may be in a parallel configuration (round, oval or D-shaped cross section) or in a coaxial configuration (round or oval cross section). The positioning and shape of the openings of the two lumens and their position in respect to one another is the main design elements of the catheter tip design for dual lumen catheters.

Some hemodialysis catheters are of a triple lumen design, where the inner diameter of round or oval catheter body is divided into two equal sized lumens (arterial (inlet) and venous (outlet)) and one smaller lumen. The lumens of the catheter may be in a parallel configuration (round, oval or D-shaped cross section) or in a coaxial configuration (round or oval cross section). The position of the third lumen may be between the two large lumens or offset from the two larger lumens. The positioning and shape of the openings of the three lumens and their position in respect to one another are the main design elements of the catheter tip design for triple lumen catheters.

Another catheter tip geometry/configuration is the coaxial design. The arterial lumen (inlet) opens at the distal tip of the catheter body in the form of a taper or round profile and may have one or more additional openings on the side of the tip and/or catheter body. The venous lumen (outlet) opening is in line with the axis of the opening of the arterial lumen and may have one or more additional openings on the side of the catheter body. The venous lumen (outlet) openings are proximal to the openings of the arterial lumen. The catheter body diameter between the arterial and venous lumen opening is a smaller outer diameter than the catheter body outer diameter proximal of the venous lumen openings and is coaxial to the catheter body and consist solely of the arterial lumen.

Because the arterial lumen protrudes through the center axis of the catheter body, the venous lumen openings may occur at the point where the smaller arterial catheter outer diameter begins and may occur around all or part of the circumference of the small catheter body outer diameter. Examples of the coaxial tip design are Covidien HemoStream and Bard Brevia™.

Another catheter tip geometry/configuration is the symmetric design exemplified by the Covidien Palindrome™ Catheters. The arterial lumen (inlet) and venous lumen (outlet) open at the distal tip of the catheter body in the form of an angled or curvilinear shape opening where each lumen may have one or more additional openings on the side of the catheter body. The internal wall separating the catheter lumens extends fully to the distal tip of the catheter providing a separation between the arterial and venous lumen openings.

An example of a triple lumen hemodialysis catheter distal tip geometry/configuration is commonly referred to as a "taper tip" design. The arterial lumen (inlet) opens at the distal tip of the taper and may have one or more additional openings on the side of the taper and/or catheter body. The venous lumen (outlet) opening may consist of one or more openings on the side of the catheter body and are proximal to the openings of the arterial lumen. The third lumen opening may consist of one or more openings on the side of the catheter body and are proximal to the openings of the venous lumen. The taper tip portion of the catheter body may be made of a different polymer than the rest of the catheter body. Examples of catheter with this tip design are the Covidien Mahurkar™ line of 12 French, Triple Lumen acute hemodialysis catheters, Medcomp T3™, and the Medcomp Tri-Flow®.

A modified form of the triple lumen taper tip design is exemplified by the Bard Power-Trialysis™ catheter that has the arterial and venous lumen openings on opposite, but parallel sides of the proximal portion of the taper tip with the opening for the third lumen positioned distal to that of the arterial and venous lumen openings with no openings at the distal end of the taper.

In general, it is preferred that the thickness of the hydrophilic polymer on a catheter component be relatively uniform. With respect to the catheter body, for example, it is generally preferred that the Dry Thickness of the hydrophilic polymer layer on exterior surface 24 and on intraluminal surface 26 at a position located in the Midpoint Region between proximal end 23 and distal end 25 be at least 50 nm. In one such preferred embodiment, the Dry Thickness on the intraluminal surface at a position located in the Midpoint Region between proximal end 23 and distal end 25 be at least 100 nm. In another such preferred embodiment, the Dry Thickness on the intraluminal surface at a position located in the Midpoint Region between proximal end 23 and distal end 25 is at least 250 nm. In another such preferred embodiment, the Dry Thickness on the intraluminal surface at a position located in the Midpoint Region between proximal end 23 and distal end 25 is at least 300 nm. In another such preferred embodiment, the Dry Thickness on the intraluminal surface at a position located in the Midpoint Region between proximal end 23 and distal end 25 is at least 400 nm. In another such preferred embodiment, the Dry Thickness on the intraluminal surface at a position located in the Midpoint Region between proximal end 23 and distal end 25 is at least 500 nm. In another such preferred embodiment, the Dry Thickness on the intraluminal surface at a position located in the Midpoint Region between proximal end 23 and distal end 25 is at least 1,000 nm.

In certain embodiments, it is also preferred that thickness of the hydrophilic polymer on the external and intraluminal surfaces of the juncture hub be relatively uniform. For example, it is generally preferred that the Dry Thickness of the grafted zwitterionic polymer layer on the exterior surface of the juncture hub and on the juncture hub intraluminal surfaces at a position located in the Midpoint Region between proximal and distal ends of each of the juncture hub lumen(s) be at least 50 nm. In one such preferred embodiment, the Dry Thickness on the exterior surface of the juncture hub and on the juncture hub intraluminal surfaces at a position located in the Midpoint Region between the proximal and distal ends of each of the juncture hub lumen(s) be at least 100 nm. In another such preferred embodiment, the Dry Thickness on the exterior surface of the juncture hub and on the juncture hub intraluminal surfaces at a position located in the Midpoint Region between the proximal and distal ends of each of the juncture hub lumen(s) be at least 250 nm. In another such preferred embodiment, the Dry Thickness on the exterior surface of the juncture hub and on the juncture hub intraluminal surfaces at a position located in the Midpoint Region between the proximal and distal ends of each of the juncture hub lumen(s) be at least 500 nm. In another such preferred embodiment, the Dry Thickness on the exterior surface of the juncture hub and on the juncture hub intraluminal surfaces at a position located in the Midpoint Region between the proximal and distal ends of each of the juncture hub lumen(s) be at least 1,000 nm. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In certain embodiments, it is also preferred that the thickness of the hydrophilic polymer on the exterior and intraluminal surfaces of each of the extension lines be relatively uniform. For example, it is generally preferred that the Dry Thickness of the hydrophilic polymer layer on the exterior surface of each of the extension lines and on the intraluminal surfaces of the extension line(s) at a position located in the Midpoint Region between proximal and distal ends of each of the extension line lumen(s) be at least 50 nm. In one such preferred embodiment, the Dry Thickness on the exterior surface of each of the extension lines and on the intraluminal surfaces of the extension line(s) at a position located in the Midpoint Region between the proximal and distal ends of each of the extension line lumen(s) be at least 100 nm. In another such preferred embodiment, the Dry Thickness on the exterior surface of each of the extension lines and on the intraluminal surfaces of the extension line(s) at a position located in the Midpoint Region between the proximal and distal ends of each of the extension line lumen(s) be at least 250 nm. In another such preferred embodiment, the Dry Thickness on the exterior surface of each of the extension lines and on the intraluminal surfaces of the extension line(s) at a position located in the Midpoint Region between the proximal and distal ends of each of the extension line lumen(s) be at least 500 nm. In another such preferred embodiment, the Dry Thickness on the exterior surface of each of the extension lines and on the intraluminal surfaces of the extension line(s) at a position located in the Midpoint Region between the proximal and distal ends of each of the extension line lumen(s) be at least 1,000 nm. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In certain embodiments, it is also preferred that the thickness of the hydrophilic polymer on the external and intraluminal surfaces of each of the connectors be relatively uniform. For example, it is generally preferred that the Dry Thickness of the grafted zwitterionic polymer layer on the exterior surface of each of the connectors and on the intraluminal surfaces of the connector(s) at a position located in the Midpoint Region between proximal and distal ends of each of the connector lumen(s) be at least 50 nm. In one such preferred embodiment, the Dry Thickness on the exterior surface of each of the connectors and on the intraluminal surfaces of the connector(s) at a position located in the Midpoint Region between the proximal and distal ends of each of the connector(s) be at least 100 nm. In another such preferred embodiment, the Dry Thickness on the exterior surface of each of the connectors and on the intraluminal surfaces of the connector(s) at a position located in the Midpoint Region between the proximal and distal ends of each of the connector lumen(s) be at least 250 nm. In another such preferred embodiment, the Dry Thickness on the exterior surface of each of the connectors and on the intraluminal surfaces of the connector(s) at a position located in the Midpoint Region between the proximal and distal ends of each of the connector lumen(s) be at least 500 nm. In another such preferred embodiment, the Dry Thickness on the exterior surface of each of the connectors and on the intraluminal surfaces of the connector(s) at a position located in the Midpoint Region between the proximal and distal ends of each of the connector lumen(s) be at least 1,000 nm. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In one preferred embodiment, the Dry Thickness at a position located in the Midpoint Region of the intraluminal surface of a catheter component (that is, at a position located in the Midpoint Region in the axial direction along the surface of a lumen of the catheter component) such as the catheter body, juncture hub, extension line or connector is less than 500 microns. For example, in one embodiment, the Dry Thickness at a position located in the Midpoint Region of a lumen of such a catheter component is less than 250 microns. By way of further example, in one such embodiment, the Dry Thickness at a position located in the Midpoint Region of the lumen of such a catheter component is less than 100 microns. By way of further example, in one such embodiment, the Dry Thickness at a position located in the Midpoint Region of the lumen of such a catheter component is less than 50 microns. By way of further example, in one such embodiment, the Dry Thickness at a position located in the Midpoint Region of the lumen of such a catheter component is less than 25 microns. By way of further example, in one such embodiment, the Dry Thickness at a position located in the Midpoint Region of the lumen of such a catheter component is less than 10 microns. By way of further example, in one such embodiment, the Dry Thickness at a position located in the Midpoint Region of the lumen of such a catheter component is less than 5 microns.

In general, the Dry Thickness of the hydrophilic polymer layer at a position located in the Midpoint Region of the lumen of a catheter component such as the catheter body, juncture hub, extension line or connector is at least 50% as great as the Average Dry Thickness of the hydrophilic polymer layer for the full length of such lumen of that catheter component (i.e., the Average Dry Thickness of the zwitterionic polymer layer on the surface of lumen from the proximal to the distal ends of the catheter component containing such lumen). For example, in one such embodiment, the Dry Thickness of the hydrophilic polymer layer at a position located in the Midpoint Region of the lumen of such a catheter component is at least 75% as great as the Average Dry Thickness of the hydrophilic polymer layer for the full length of such lumen of that catheter component. By way of further example, in one such embodiment, the Dry Thickness at a position located in the Midpoint Region of the lumen of such a catheter component is at least 80% as great as the Average Dry Thickness of the hydrophilic polymer layer for the full length of such lumen of that catheter component. By way of further example, in one such embodiment, the Dry Thickness at a position located in the Midpoint Region of the lumen of such a catheter component is at least 90% as great as the Average Dry Thickness of the hydrophilic polymer layer for the full length of such lumen of that catheter component. By way of further example, in one such embodiment, the Dry Thickness at a position located in the Midpoint Region of the lumen of such a catheter component is at least 95% as great as the Average Dry Thickness of the hydrophilic polymer layer for the full length of such lumen of that catheter component. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

The Standard Deviation of the Average Dry Thickness of the hydrophilic polymer layer as measured along the length of a lumen of a catheter component such as the catheter body, juncture hub, extension line or connector (i.e., the Standard Deviation of the Average Dry Thickness of the hydrophilic polymer layer on the surface of lumen from the proximal to the distal ends of the catheter component containing such lumen) is also preferably less than 100% of the Average Dry Thickness as measured along the length of the lumen of that catheter component (i.e., the Average Dry Thickness of the hydrophilic polymer layer on the surface of lumen from the proximal to the distal ends of the catheter component containing such lumen). For example, in one such embodiment the Standard Deviation of the Average Dry Thickness as measured along the length of the lumen of that catheter component is less than 75% of the Average Dry Thickness as measured along the length of the lumen of that catheter component. By way of further example, in one such embodiment the Standard Deviation of the Average Dry Thickness as measured along the length of the lumen of that catheter component is less than 50% of the Average Dry Thickness as measured along the length of the lumen of that catheter component. By way of further example, in one such embodiment the Standard Deviation of the Average Dry Thickness as measured along the length of the lumen of that catheter component is less than 25% of the Average Dry Thickness as measured along the length of the lumen of that catheter component. By way of further example, in one such embodiment the Standard Deviation of the Average Dry Thickness as measured along the length of the lumen of that catheter component is less than 20% of the Average Dry Thickness as measured along the length of the lumen of that catheter component. By way of further example, in one such embodiment the Standard Deviation of the Average Dry Thickness as measured along the length of the lumen of that catheter component is less than 15% of the Average Dry Thickness as measured along the length of the lumen of that catheter component. By way of further example, in one such embodiment the Standard Deviation of the Average Dry Thickness as measured along the length of the lumen of that catheter component is less than 10% of the Average Dry Thickness as measured along the length of the lumen of that catheter component. By way of further example, in one such embodiment the Standard Deviation of the Average Dry Thickness as measured along the length of the lumen of that catheter component is less than 5% of the Average Dry Thickness as measured along the length of the lumen of that catheter component. By way of further example, in one such embodiment the Standard Deviation of the Average Dry Thickness as measured along the length of the lumen of that catheter component is less than 3% of the Average Dry Thickness as measured along the length of the lumen of that catheter component. By way of further example, in one such embodiment the Standard Deviation of the Average Dry Thickness as measured along the length of the lumen of that catheter component is less than 1% of the Average Dry Thickness as measured along the length of the lumen of that catheter component. In each such instance, the lumen of the catheter component described above may be the lumen of a catheter body, juncture hub, extension line, connector (e.g., luer hub) or other catheter component that may contact fluids administered to or removed from a patient. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In a preferred embodiment, the hydrophilic polymer layer on the lumen of a catheter component such as the lumen of a catheter body, juncture hub, extension line or connector is conformal. For example, in one embodiment, the hydrophilic polymer layer on the lumen surface of such a component is Conformal at a level of 500 $mm^2$. By way of further example, in one such embodiment, the hydrophilic polymer layer on the lumen surface of such a catheter component is Conformal at a level of 250 $mm^2$. By way of further example, in one such embodiment, the hydrophilic polymer layer on the lumen surface of such a catheter component is Conformal at a level of 100 $mm^2$. By way of further example, in one such embodiment, the hydrophilic polymer layer on the lumen surface of such a catheter component is Conformal at a level of 50 $mm^2$. By way of further example, in one such embodiment, the hydrophilic polym By way of further example, in one such embodiment, the hydrophilic polymer layer on the lumen surface of such a catheter component is Conformal at a level of 25 $mm^2$. By way of further example, in one such embodiment, the hydrophilic polymer layer on the lumen surface of such a catheter component is Conformal at a level of 10 $mm^2$. By way of further example, in one such embodiment, the hydrophilic polymer layer on the lumen surface of such a catheter component is Conformal at a level of 5 $mm^2$. By way of further example, in one such embodiment, the hydrophilic polymer layer on the lumen surface of such a catheter component is Conformal at a level of 2 $mm^2$. By way of further example, in one such embodiment, the hydrophilic polymer layer on the lumen surface of such a catheter component is Conformal at a level of 1 $mm^2$. By way of further example, in one such embodiment, the hydrophilic polymer layer on the lumen surface of such a catheter component is Conformal at a level of 0.5 $mm^2$. By way of further example, in one such embodiment, the hydrophilic polymer layer on the lumen surface of such a catheter component is Conformal at a level of 0.1 $mm^2$. In each such instance, the lumen of the catheter component described above may be the lumen of a catheter body, juncture hub, extension line, connector (e.g., luer hub) or other catheter component that may contact fluids administered to or removed from a patient. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

In some embodiments, it may be desired to modify only a portion of the lumen of a catheter component with a hydrophilic polymer. In those regions in which lumen surface modification with the hydrophilic polymer is desired, it is generally preferred that the polymer layer be conformal and have a thickness of at least 50 nm in such region. In general, however, such regions will have a length (as measured in a direction from the proximal to the distal end of the lumen region modified with the hydrophilic polymer) of at least 2 cm. For example, in one such embodiment, the Average Dry Thickness of a hydrophilic polymer layer in a region of a lumen surface having a length of at least 2 cm will be at least 50 nm. By way of further example, in one such embodiment, the Average Dry Thickness of a hydrophilic polymer layer in a region of a lumen surface having a length of at least 2 cm will be at least 100 nm. By way of further example, in one such embodiment, the Average Dry Thickness of a hydrophilic polymer layer in a region of a lumen surface having a length of at least 2 cm will be at least 250 nm. By way of further example, in one such embodiment, the Average Dry Thickness of a hydrophilic polymer layer in a region of a lumen surface having a length of at least 2 cm will be at least 500 nm. By way of further example, in one such embodiment, the Average Dry Thickness of a hydrophilic polymer layer in a region of a lumen surface having a length of at least 2 cm will be at least 1000 nm. In each such instance, the lumen of the catheter component described above may be the lumen of a catheter body, juncture hub, extension line, connector (e.g., luer hub) or other catheter component that may contact fluids administered to or removed from a patient. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

The Average Dry Thickness of the hydrophilic polymer layer as measured along the length of a lumen of a catheter component such as the catheter body, juncture hub, extension line or connector (i.e., the Average Dry Thickness of the hydrophilic polymer layer on the surface of lumen from the proximal to the distal ends of the catheter component containing such lumen) is also preferably a substantial fraction of the Average Dry Thickness of the hydrophilic polymer layer on the external surface of the catheter component comprising such lumen as measured along the length of the catheter component (i.e., the Average Dry Thickness of the hydrophilic polymer layer on the external surface of the catheter component containing such lumen from the proximal to the distal ends thereof). For example, in one such embodiment the Average Dry Thickness of the hydrophilic polymer layer as measured along the length of a lumen of a catheter component is greater than 10% of the Average Dry Thickness of the hydrophilic polymer layer as measured along the length of the external surface of that catheter component. By way of further example, in one such embodiment, the Average Dry Thickness of the hydrophilic polymer layer as measured along the length of the lumen of that catheter component is greater than 25% of the Average Dry Thickness of the hydrophilic polymer layer as measured along the length of the external surface of that catheter component. By way of further example, in one such embodiment, the Average Dry Thickness of the hydrophilic polymer layer as measured along the length of the lumen of that catheter component is greater than 50% of the Average Dry Thickness of the hydrophilic polymer layer as measured along the length of the external surface of that catheter component. By way of further example, in one such embodiment, the Average Dry Thickness of the hydrophilic polymer layer as measured along the length of the lumen of that catheter component is greater than 75% of the Average Dry Thickness of the hydrophilic polymer layer as measured along the length of the external surface of that catheter component. By way of further example, in one such embodiment, the Average Dry Thickness of the hydrophilic polymer layer as measured along the length of the lumen of that catheter component is greater than 85% of the Average Dry Thickness of the hydrophilic polymer layer as measured along the length of the external surface of that catheter component. By way of further example, in one such embodiment, the Average Dry Thickness of the hydrophilic polymer layer as measured along the length of the lumen of that catheter component is greater than 90% of the Average Dry Thickness of the hydrophilic polymer layer as measured along the length of the external surface of that catheter component. By way of further example, in one such embodiment, the Average Dry Thickness of the hydrophilic polymer layer as measured along the length of the lumen of that catheter component is greater than 95% of the Average Dry Thickness of the hydrophilic polymer layer as measured along the length of the external surface of that catheter component. By way of further example, in one such embodiment, the Average Dry Thickness of the hydrophilic polymer layer as measured along the length of the lumen of that catheter component is greater than 97% of the Average Dry Thickness of the hydrophilic polymer layer as measured along the length of the external surface of that catheter component. By way of further example, In one such embodiment, the Average Dry Thickness of the hydrophilic polymer layer as measured along the length of the lumen of that catheter component is greater than 99% of the Average Dry Thickness of the hydrophilic polymer layer as measured along the length of the external surface of that catheter component. In each such instance, the lumen of the catheter component described above may be the lumen of a catheter body, juncture hub, extension line, connector (e.g., luer hub) or other catheter component that may contact fluids administered to or removed from a patient.

In a preferred embodiment, the Dry Thickness at a position located in the Midpoint Region of the lumen of a catheter component (i.e., the Dry Thickness of the hydrophilic polymer layer on the surface of lumen at a position located in the Midpoint Region from the proximal to the distal ends of the catheter component containing such lumen) is greater than 10% of the Average Dry Thickness as measured along the length of the external surface of that catheter component (i.e., the Dry Thickness of the hydrophilic polymer layer on the external surface of the catheter component containing such lumen at a position located in the Midpoint Region from the proximal to the distal ends thereof). For example, in one such embodiment, the Dry Thickness at a position located in the Midpoint Region of the lumen of a catheter component is greater than 25% of the Average Dry Thickness as measured along the length of the external surface of that catheter component. By way of further example, in one such embodiment the Dry Thickness at a position located in the Midpoint Region of the lumen of a catheter component is greater than 50% of the Average Dry Thickness as measured along the length of the external surface of that catheter component. By way of further example, in one such embodiment the Dry Thickness at a position located in the Midpoint Region of the lumen of a catheter component is greater than 75% of the Average Dry Thickness as measured along the length of the external surface of that catheter component. By way of further example, in one such embodiment the Dry Thickness at a position located in the Midpoint Region of the lumen of a catheter component is greater than 85% of the Average Dry Thickness as measured along the length of the external surface of that catheter component. By way of further example, in one such embodiment the Dry Thickness at a position located in the Midpoint Region of the lumen of a catheter component is greater than 90% of the Average Dry Thickness as measured along the length of the external surface of that catheter component. By way of further example, in one such embodiment the Dry Thickness at a position located in the Midpoint Region of the lumen of a catheter component is greater than 95% of the Average Dry Thickness as measured along the length of the external surface of that catheter component. By way of further example, in one such embodiment the Dry Thickness at a position located in the Midpoint Region of the lumen of a catheter component is greater than 97% of the Average Dry Thickness as measured along the length of the external surface of that catheter component. By way of further example, in one such embodiment the Dry Thickness at a position located in the Midpoint Region of the lumen of a catheter component is greater than 99% of the Average Dry Thickness as measured along the length of the external surface of that catheter component. In each such instance, the lumen of the catheter component described above may be the lumen of a catheter body, juncture hub, extension line, connector (e.g., luer hub) or other catheter component that may contact fluids administered to or removed from a patient.

The lumen(s) of a catheter body, juncture hub, extension line, connector (e.g., luer hub) and/or other catheter components that are designed to contact fluids administered to or removed from a patient typically have a Lumen Aspect Ratio of at least 3:1. For example, in certain embodiments the lumen(s) of a catheter body, juncture hub, extension line, connector (e.g., luer hub) and/or other catheter components that are designed to contact fluids administered to or removed from a patient may have a Lumen Aspect Ratio of at least 5:1. By way of further example, in one such embodiment the lumen(s) of a catheter body, juncture hub, extension line, connector (e.g., luer hub) and/or other catheter components that are designed to contact fluids administered to or removed from a patient may have a Lumen Aspect Ratio of at least 10:1. By way of further example, in one such embodiment the lumen(s) of a catheter body, juncture hub, extension line, connector (e.g., luer hub) and/or other catheter components that are designed to contact fluids administered to or removed from a patient may have a Lumen Aspect Ratio of at least 25:1. By way of further example, in one such embodiment the lumen(s) of a catheter body, juncture hub, extension line, connector (e.g., luer hub) and/or other catheter components that are designed to contact fluids administered to or removed from a patient may have a Lumen Aspect Ratio of at least 50:1. By way of further example, in one such embodiment the lumen(s) of a catheter body, juncture hub, extension line, connector (e.g., luer hub) and/or other catheter components that are designed to contact fluids administered to or removed from a patient may have a Lumen Aspect Ratio of at least 100:1. By way of further example, in one such embodiment the lumen(s) of a catheter body, juncture hub, extension line, connector (e.g., luer hub) and/or other catheter components that are designed to contact fluids administered to or removed from a patient may have a Lumen Aspect Ratio of at least 250:1. By way of further example, in one such embodiment the lumen(s) of a catheter body, juncture hub, extension line, connector (e.g., luer hub) and/or other catheter components that are designed to contact fluids administered to or removed from a patient may have a Lumen Aspect Ratio of at least 500:1. By way of further example, in one such embodiment the lumen(s) of a catheter body, juncture hub, extension line, connector (e.g., luer hub) and/or other catheter components that are designed to contact fluids administered to or removed from a patient may have a Lumen Aspect Ratio of at least 1000:1. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer. Additionally, in each of the foregoing examples and embodiments recited in this paragraph, the Average Dry Thickness, Standard Deviation of the Average Dry Thickness, Conformality, Dry Thickness, fibrinogen adsorption in a fibrinogen adsorption assay, contact angle, surface roughness and each of the other parameters specified herein with respect to a non-fouling surface modification may be as provided elsewhere herein.

To tailor a catheter for a given medical procedure, a catheter tip may be subjected to a processing step comprising heating and bending, laser-cutting or the like to provide with the catheter tip with a complex geometric shape, cut-out or both. Such steps, however, may alter the chemical or physical properties of the Tip Region of the catheter body relative to other parts of the catheter body which, in turn, may affect the extent of modification of the surface by the zwitterionic polymer. In general, however, the Dry Thickness as determined for the Tip Region is at least 25% of the Average Dry Thickness as measured along the length of the lumen of that catheter component. For example, in one such embodiment the Dry Thickness as measured on the Tip Region is at least 50% of the Average Dry Thickness as measured along the length of the lumen of that catheter component. By way of further example, in one such embodiment the Dry Thickness as measured on the Tip Region is at least 80% of the Average Dry Thickness as measured along the length of the lumen of that catheter component. By way of further example, in one such embodiment the Dry Thickness as measured on the Tip Region is at least 90% of the Average Dry Thickness as measured along the length of the lumen of that catheter component. By way of further example, in one such embodiment the Dry Thickness as measured on the Tip Region is at least 95% of the Average Dry Thickness as measured along the length of the lumen of that catheter component. In one embodiment for each of the examples and embodiments recited in this paragraph, the Average Dry Thickness as measured on the Tip Region of the hydrophilic polymer is at least about 50 nm. For some Tip Regions, substantially thicker grafted polymer layers may be desirable. For example, in the Tip Region the hydrophilic polymer layer may have an Average Dry Thickness of 50 micrometers. Typically, however, the grafted hydrophilic polymer layer in the Tip Region will have an average thickness that is less. For example, in some embodiments the grafted hydrophilic polymer layer in the Tip Region will have an Average Dry Thickness of up to 10 micrometers. By way of further example, in some embodiments the grafted hydrophilic polymer layer in the Tip Region will have an Average Dry Thickness of up to 1 micrometer. By way of further example, in some embodiments the grafted hydrophilic polymer layer in the Tip Region will have a Average Dry Thickness of up to 500 nm. By way of further example, in some embodiments the grafted hydrophilic polymer layer in the Tip Region will have an Average Dry Thickness in the range of about 100 nm to about 1,000 nm. By way of further example, in some embodiments the grafted hydrophilic polymer layer in the Tip Region will have an Average Dry Thickness in the range of about 200 nm to about 700 nm. By way of further example, in some embodiments the grafted hydrophilic polymer layer in the Tip Region will have an Average Dry Thickness in the range of about 300 nm to about 600 nm. By way of further example, in some embodiments the grafted hydrophilic polymer layer in the Tip Region will have an Average Dry Thickness in the range of about 100 nm to about 5,000 nm. By way of further example, in some embodiments the grafte hydrophilic polymer layer in the Tip Region will have an Average Dry Thickness in the range of about 300 nm to about 3,000 nm. By way of further example, in some embodiments the grafted hydrophilic polymer layer in the Tip Region will have an Average Dry Thickness in the range of about 500 nm to about 2,500 nm. In a preferred embodiment, the Average Dry Thickness of the grafted polymer layer in the Tip Region is determined using a scanning electron microscope (SEM) under vacuum or by analyzing the intensity of the chemical signals in the polymer layer, for instance, through the use of ATR-FTIR. In a preferred embodiment, the hydrophilic polymer in each of the foregoing examples recited in this paragraph is non-fouling. In one embodiment, the hydrophilic polymer in each of the foregoing examples recited in this paragraph is a zwitterionic polymer. In one embodiment, the hydrophilic polymer in each of the foregoing examples and embodiments recited in this paragraph is a polymer containing neutral hydrophilic pendant groups such as alkoxylated moieties. In one embodiment, the hydrophilic polymer in each of the foregoing examples and embodiments recited in this paragraph is a polymer containing phosphorylcholine, carboxyammonium or sulfoammonium repeat units. In one embodiment, the hydrophilic polymer in each of the foregoing examples and embodiments recited in this paragraph is a polymer containing sulfobetaine or carboxybetaine repeat units. In one embodiment, the hydrophilic polymer in each of the foregoing examples and embodiments recited in this paragraph is a zwitterionic polymer and the zwitterionic polymer is grafted from a polyurethane polymer or copolymer. In one embodiment, the hydrophilic polymer in each of the foregoing examples and embodiments recited in this paragraph is a carboxyammonium or sulfoammonium polymer and the carboxyammonium or sulfoammonium polymer is grafted from a polyurethane polymer or copolymer. In one embodiment, the hydrophilic polymer in each of the foregoing examples and embodiments recited in this paragraph is a polymer containing sulfobetaine or carboxybetaine repeat units and the polymer containing sulfobetaine or carboxybetaine repeat units is grafted from a polyurethane polymer or copolymer.

Further, the Tip Region of catheters are particularly at risk for thrombus formation because of the disturbances to blood flow that may be created at the point of insertion into the vascular system during device use. To minimize the risk for thrombus formation, therefore, it is preferred that the zwitterionic polymer surface modification be relatively uniform and conformal. For example, in one embodiment the Tip Region is Conformal at a level of 0.01 mm². In some embodiments, the Tip Region is Conformal at a level of 0.05 mm². In some embodiments, the Tip Region is Conformal at a level of 0.1 mm². In some embodiments, the Tip Region is Conformal at a level of 0.25 mm². In some embodiments, the Tip Region is Conformal at a level of 0.5 mm².

In those embodiments in which the catheter body contains radio-opaque agents such as barium sulfate, one possible outcome during tip formation, particularly through laser-cutting or heat-forming is the formation of a Tip Region that has an increased level of inorganic radio-opaque agents on the exterior surface and the lumen surface of the catheter body in the Tip Region relative to the exterior surface and the lumen surface of the catheter body in the remainder of the catheter body. In some embodiments, the Tip Region or the whole catheter is exposed to a solution to dissolve some or all of the radio-opaque agents before the surface modification is applied. In one such exemplary embodiment, the catheter body is treated with an acid (e.g., 1N hydrochloric acid) or a base (e.g., 1N sodium hydroxide) to at least partially remove exposed particles of barium sulfate or other radio-opaque agent. Alternatively, a chelator solution such as 1 N ethylenedioxy-diethylene-dinitrilo-tetraacetic acid (EDTA) may be applied on the polyurethane. Acid, base, and/or chelator treatment times may be in the range of 1 hour to 24 hours, or longer; more preferably about 2 hours. Without being bound by any particular theory, acid, base, and/or chelator treatment can reduce or at least partially remove the particles from the surface by increasing their solubility in the solution, and/or by decreasing the particle's adherence to the substrate. Representative acids include, for example, hydrochloric acid, sulfuric acid, nitric acid, phosphoric acid, boric acid, hydrofluoric acid, hydrobromic acid, lactic acid, acetic acid, carbonic acid, formic acid, citric acid, oxalic acid, uric acid, carboxylic acids, sulfonic acids, sulfamic acid, chlorous acid, and the like. Representative bases include, for example, sodium hydroxide, potassium hydroxide, ammonia solution, sodium chlorite, and the like. Representative chelators include, for example, water, carbohydrates, including polysaccharides, organic acids with more than one coordination group, lipids, steroids, amino acids and related compounds, peptides, phosphates, nucleotides, tetrapyrrols, ferrioxamines, ionophores, such as gramicidin, monensin, valinomycin, phenolics, 2,2'-bipyridyl, dimercaptopropanol, ethylenediaminotetraacetic acid, EDTA, ethylenedioxy-diethylene-di nitrilo-tetraacetic acid, EGTA, ethylene glycol-bis-(2-aminoethyl)-N,N,N',N'-tetraacetic acid, nitrilotriacetic acid, NTA, ortho-phenanthroline, salicylic acid, triethanolamine, TEA, 5-sulfosalicylic acid, oxalic acid, citric acid, tartaric acid, ethylene glycol-bis(2-aminoethylether)-N,N,N',N'-tetraacetic acid, enterobactin, ethylenediaminetetra(methylenephosphonic acid) and corresponding salts, and the like. Certain preferred chelators are polyamino carboxylic acids, e.g., glycine, beta-alanine, iminodiacetic acid (IDA), nitrilotriacetic acid (NTA), ethylenediaminetetraacetic acid, (EDTA), diethylene triamine pentaacetic acid (DTPA), 1,2-bis(o-aminophenoxy) ethane-N,N,N',N'-tetraacetic acid (BAPTA), 1,4,7,10-tetraazacyclododecane-1,4,7,10-tetraacetic acid (DOTA), and the like.

As previously noted, catheter components (e.g., the catheter body, juncture hub, extension line(s) and connectors such as luer hubs) may comprise different polymers, copolymers or even different grades of the same polymer or copolymer. In such instances, it may be preferable to have a hydrophilic polymer surface modification on the exterior surfaces and/or intraluminal surfaces of these different materials but the thickness of the surface modification may be different for the different components. For example, in one embodiment the Average Dry Thickness as measured along the length of the lumen of the extension line is at least 25% of the Average Dry Thickness as measured along the length of the lumen of that catheter body. By way of further example, in one embodiment the Average Dry Thickness as measured along the length of the lumen of the extension line is at least 50% of the Average Dry Thickness as measured along the length of the lumen of that catheter body. By way of further example, in one embodiment the Average Dry Thickness as measured along the length of the lumen of the extension line is at least 80% of the Average Dry Thickness as measured along the length of the lumen of that catheter body. By way of further example, in one embodiment the Average Dry Thickness as measured along the length of the lumen of the extension line is at least 90% of the Average Dry Thickness as measured along the length of the lumen of that catheter body. By way of further example, in one embodiment the Average Dry Thickness as measured along the length of the lumen of the extension line is at least 95% of the Average Dry Thickness as measured along the length of the lumen of that catheter body. By way of further example, in one embodiment these ratios are met when the catheter body and lumen are formed from different materials.

In a preferred embodiment, some consideration is given to the combined thickness of the undercoating and the grafted polymer layer. For example, it is generally preferred that the undercoating and the grafted polymer not materially change the dimensions of the components of a device, such as lumen diameters. Thus, in some embodiments, the combined Average Dry Thickness of the undercoating and the grafted polymer layer is <1% of the diameter of a catheter lumen in which it is applied. In some embodiments, the Average Dry Thickness of the undercoating and the grafted polymer layer is <0.5% of the diameter of a catheter lumen in which it is applied. In some embodiments, the Average Dry Thickness of the undercoating and the grafted polymer layer is <0.25% of the diameter of a catheter lumen in which it is applied. In further embodiments, the Average Dry Thickness of the undercoating and the grafted polymer layer is <0.1% of the diameter of a catheter lumen in which it is applied. In certain embodiments, the Average Dry Thickness of the undercoating and the grafted polymer layer is <0.05% of the diameter of a catheter lumen in which it is applied. In further embodiments, the Average Dry Thickness of the undercoating and the grafted polymer layer is <0.01% of the diameter of a catheter lumen in which it is applied. In further embodiments, the Average Dry Thickness of the undercoating and the grafted polymer layer is <0.001% of the diameter of a catheter lumen in which it is applied.

Surface Modifications

In general, a hydrophilic, preferably non-fouling, polymeric material is grafted from a substrate into which one or more polymerization initiators have been incorporated. In one embodiment, the hydrophilic polymeric material is grafted from a substrate that is a composite of two or more materials, e.g., an underlying polymeric material with a coating of a different polymeric material thereon (e.g., an undercoating or a precoating as described elsewhere herein). For example, in one embodiment, the hydrophilic polymeric material is grafted from a polymeric undercoat layer, such as a polyurethane layer which overlies a polymeric bulk material, such as polyurethane.

Preferably, the hydrophilic polymeric material that is grafted from the substrate comprises a chain-growth polymer (that is, a polymer or polymer block formed by addition polymerization), or a combination thereof. The chain-growth polymer may be, for example, an addition polymer derived from monomer(s) incorporating double or triple bonds, e.g., an olefin. By way of further example, the chain-growth polymer may comprise an addition polymer derived from a cyclic monomer by means of a ring-opening polymerization reaction. Thus, the polymer may be a chain-growth homopolymer or copolymer. In a preferred embodiment, the polymer is a chain growth addition homopolymer or a chain growth addition copolymer comprising the residue of two or more monomers.

In accordance with one aspect of the present invention, it is generally preferred that the hydrophilic polymeric material be prepared without inordinate use of a polyfunctional crosslinking agent. For example, it is generally preferred that the hydrophilic polymeric material contain less than 50 mole % of the residue of a polyvalent crosslinker. In one such embodiment, the hydrophilic polymeric material contains less than 25 mole % of the residue of a polyvalent crosslinker. In one such embodiment, the hydrophilic polymeric material contains less than 10 mole % of a polyvalent crosslinker. In one such embodiment, the hydrophilic polymeric material contains less than 5 mole % of the residue of a polyvalent crosslinker. In one such embodiment, the hydrophilic polymeric material contain less than 3 mole % of a polyvalent crosslinker. In one such embodiment, the hydrophilic polymeric material contains less than 0.1 mole % of the residue of a polyvalent crosslinker. In one such embodiment, the hydrophilic polymeric material contains no residue of a polyvalent crosslinker.

Through grafting, step-growth or chain-growth techniques, the hydrophilic polymeric material may comprise any of a range of polymer types or combinations thereof. The polymer backbone may be neutral (e.g., polyalkylene or polyether) or contain permanently charged moieties (e.g., cyclic or acyclic quaternized nitrogen atoms), or even zwitterionic backbones (e.g., phosphorylcholine backbones). In one embodiment, therefore, the hydrophilic polymeric material comprises a polymer or copolymer selected from the group consisting of polyamide, polyamine, polyanhydride, polyazine, poly(carbonate), polyester, polyether, polyetheretherketone (PEEK), polyguanidine, polyimide, polyketal, poly(ketone), polyolefin, poly(orthoester), polyphosphazine, polysaccharide, polysiloxane, polysulfone, polyurea, polyurethane, halogenated polymer, silicone, hydrocarbon, ether-ester, ether-amide or ionized polyethylene and combinations thereof.

The polymer may also contain a wide range of pendant (side-chain) groups, hydrophilic and hydrophobic, neutral, anionic, cationic, or mixed charged. For example, the pendant groups may include neutral hydrophilic groups such as hydroxy, oligo(ethylene glycol) and/or poly(ethylene glycol) moieties, or it may include charged groups such as anionic moieties, cationic moieties, and zwitterionic moieties.

Zwitterionic Groups

Zwitterions are molecules that carry formal positive and negative charges on non-adjacent atoms within the same molecule and molecules that may be ionized by addition or removal of an electrophile or a nucleophile, or by removal of a protecting group. Both natural and synthetic polymers, containing zwitterion functionality, have been shown to resist protein adhesion. In one embodiment, the zwitterionic monomer contains a phosphorylcholine moiety, a carboxyammonium moiety, a sulfoammonium moiety, derivatives thereof, or combinations thereof. In one embodiment, the zwitterionic monomer contains a carboxyammonium moiety, a sulfoammonium moiety, derivatives thereof, or combinations thereof. In one embodiment, the zwitterionic monomer contains a sulfobetaine moiety or a carboxybetaine moiety. The zwitterionic polymer may be formed by initiating polymerization with radicals present in the polymeric substrate, in the presence of one or more monomers, such as sulfobetaine methacrylate or carboxybetaine methacrylate monomers.

Polysulfoammonium polymers such as polysulfobetaines, polycarboxyammonium polymers such as polycarboxybetaines and other natural and synthetic zwitterion chemistries can be used to design non-fouling materials for the biomedical applications described herein. Some examples of natural zwitterions chemistries that could be used for non-fouling materials include, but are not limited to, amino acids, peptides, natural small molecules including, but not limited to, N,N,N-trimethylglycine (glycine betaine), trimethylamine oxide (TMAO), dimethylsulfoniopropionate sarcosine, lysergic acid and psilocybin. Additional synthetic zwitterions that could be used to create non-fouling materials, include, but are not limited to, amino-carboxylic acids (carboxybetaines), amino-sulfonic acids (sulfo betaines), cocamidopropyl betaine, quinonoid based zwitterions, decaphenylferrocene, and non-natural amino acids. Natural and synthetic polymers also include mixed charged structures with both positive charged and negative charged moieties on the pendant groups, in the main chains, or at the terminal groups.

In one embodiment, the hydrophilic polymer contains zwitterionic pendant groups covalently attached, directly or indirectly to the polymer backbone. The zwitterionic pendant groups may have an overall net charge, for instance, by having a divalent center of anionic charge and monovalent center of cationic charge or vice versa, or by having two centers of cationic charge and one center of anionic charge or vice versa. Preferably, however, the zwitterion has no overall net charge and most preferably has a center of monovalent cationic charge and a center of monovalent anionic charge. Additionally, the center(s) of cationic charge are preferably permanent; that is, it is preferably a quaternary nitrogen, quaternary phosphonium or tertiary sulfonium group. Additionally, the center(s) of anionic charge are also permanent; that is, they are completely ionized at physiological pH and are preferably carboxylate, phosphate, phosphonic, phosphonate, sulfate, sulfinic, or sulfonate.

In another embodiment, the polymer contains zwitterionic pendant groups covalently attached, directly or indirectly, to the polymer backbone, and the zwitterion corresponds to Formula ZI-3:

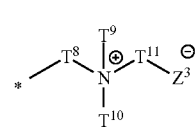

Formula ZI-3 wherein $T^8$ is a bond, hydrocarbylene, substituted hydrocarbylene, heterocyclo, or in combination with $T^9$ and $T^{10}$ and the nitrogen atom to which they are attached form a nitrogen-containing heteroaromatic ring, $T^9$ and $T^{10}$ are independently hydrogen, hydrocarbyl, substituted hydrocarbyl or heterocyclo, or, $T^9$ and $T^{10}$, in combination with $T^8$ and the nitrogen atom to which they are attached form a nitrogen-containing heteroaromatic ring, $T^{11}$ is hydrocarbylene, substituted hydrocarbylene, ether, or oxylated alkylene, $Z^3$ is carboxylate, phosphate, phosphonic, phosphonate, sulfate, sulfinic, or sulfonate, and

* designates the point of covalent attachment, direct or indirect, of the zwitterion of Formula ZI-3 to the polymer backbone.

In certain preferred embodiments in which the polymer contains zwitterionic pendant group corresponding to Formula ZI-3, $T^8$, $T^9$, $T^{10}$, and $T^{11}$ are selected from a more narrow range of substituents, $Z^3$ is carboxylate or sulfate, and the zwitterion corresponds to Formula ZI-4:

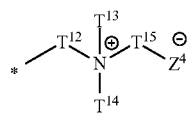

Formula ZI-4 wherein * designates the point of covalent attachment, direct or indirect, of the zwitterion of Formula ZI-4 to the polymer backbone; $T^{12}$ is a bond or —$(CH_2)_m$— with m being 1 to 3; $T^{13}$ and $T^{14}$ are independently hydrogen, alkyl, or substituted alkyl; $T^{15}$ is optionally substituted alkylene, phenylene, ether, or oxylated alkylene; and $Z^4$ is carboxylate or sulfate. For example, in this embodiment, $T^{13}$ and $T^{14}$ may independently be hydrogen or lower alkyl, e.g., methyl, ethyl, or propyl. By way of further example, in this embodiment, $T^{13}$ and $T^{14}$ may independently be hydrogen or lower alkyl, e.g., methyl, ethyl, or propyl. By way of further example, in this embodiment, $T^{15}$ may be —$(CH_2)_n$— with n being 1-8. By way of further example, in this embodiment, $T^{15}$ may be —$(CH_2)_2$— or —$(CH_2)_3$— and $T^{13}$ and $T^{14}$ may be methyl. By way of further example, in this embodiment, $T^{15}$ may be —$(CH_2)_2$— or —$(CH_2)_3$—, $T^{13}$ and $T^{14}$ may be hydrogen or alkyl. By way of further example, in this embodiment, $T^{12}$ may be —$(CH_2)_2$—, $T^{13}$ and $T^{14}$ may be methyl, $T^{15}$ may be —$(CH_2)_2$— and $Z^4$ may be carboxylate. By way of further example, in this embodiment, $T^{12}$ may be —$(CH_2)_2$—, $T^{13}$ and $T^{14}$ may be methyl, $T^{15}$ may be —$(CH_2)_3$— and $Z^4$ may be sulfate.

In certain preferred embodiments in which the polymer contains zwitterionic pendant group corresponding to Formula ZI-3, $T^8$, $T^9$ and $T^{10}$ and the nitrogen atom to which they are attached form a nitrogen-containing heteroaromatic ring. For example, $T^8$, $T^9$ and $T^{10}$ and the nitrogen atom to which they are attached may form an optionally substituted heterocycle, containing a quaternary nitrogen atom. One such embodiment corresponds to Formula ZI-5:

Formula ZI-5 wherein * designates the point of covalent attachment, direct or indirect, of the zwitterion of Formula ZI-5 to the polymer backbone; HET is a heterocycle containing a quaternary nitrogen atom, $T^{15}$ is optionally substituted alkylene, phenylene, ether, or oxylated alkylene; and $Z^4$ is carboxylate or sulfate. For example, in this embodiment, $T^{15}$ may be —$(CH_2)_n$— with n being 1-8. By way of further example, in this embodiment, $T^{15}$ may be —$(CH_2)_2$— or —$(CH_2)_3$— and $Z^4$ may be carboxylate or sulfate. By way of further example, in this embodiment, $T^{15}$ may be —$(CH_2)_3$— and $Z^4$ may be sulfate. By way of further example, in this embodiment, $T^{15}$ may be —$(CH_2)_2$— and $Z^4$ may be carboxylate. Exemplary zwitterions corresponding to Formula ZI-5 include zwitterions corresponding to Formulae ZI-6A and ZI-6B:

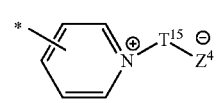

Formula ZI-6A

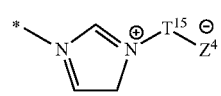

Formula ZI-6B wherein * designates the point of covalent attachment, direct or indirect, of the zwitterion of Formulae ZI-6A and ZI-6B to the polymer backbone; $T^{15}$ is optionally substituted alkylene, phenylene, ether, or oxylated alkylene; and $Z^4$ is carboxylate or sulfate. For example, in this embodiment, $T^{15}$ may be —$(CH_2)_n$— with n being 1-8. By way of further example, in this embodiment, $T^{15}$ may be —$(CH_2)_2$— or —$(CH_2)_3$— and $Z^4$ may be carboxylate or sulfate. By way of further example, in this embodiment, $T^{15}$ may be —$(CH_2)_3$— and $Z^4$ may be sulfate. By way of further example, in this embodiment, $T^{15}$ may be —$(CH_2)_2$— and $Z^4$ may be carboxylate.

In one embodiment, the polymer contains zwitterionic pendant groups covalently attached, directly or indirectly, to the polymer backbone, and the zwitterion corresponds to Formula ZI-7

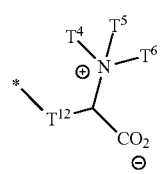

Formula ZI-7 wherein $T^4$, $T^5$ and $T^6$ are independently hydrogen, hydrocarbyl, substituted hydrocarbyl or heterocyclo; $T^{12}$ is a bond, hydrocarbylene, substituted hydrocarbylene, or heterocyclo, and * designates the point of covalent attachment, direct or indirect, of the zwitterion of Formula ZI-7 to the polymer backbone.

In one embodiment, the polymer contains zwitterionic pendant groups covalently attached, directly or indirectly, to the polymer backbone, and the zwitterion corresponds to Formula ZI-1:

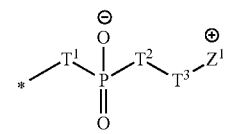

Formula ZI-1 wherein

T¹ and T² are independently oxygen, sulfur, NH or a bond,

T³ is hydrocarbylene, substituted hydrocarbylene, ether, or oxylated alkylene,

Z¹ is a moiety comprising a quaternary nitrogen, phosphonium or sulfonium cationic group, and

* designates the point of covalent attachment, direct or indirect, of the zwitterion of Formula ZI-1 to the polymer backbone.

In certain preferred embodiments in which the polymer contains zwitterionic pendant group corresponding to Formula ZI-1, T¹ and T² are oxygen, Z¹ is quaternary nitrogen, and the zwitterion corresponds to Formula ZI-2:

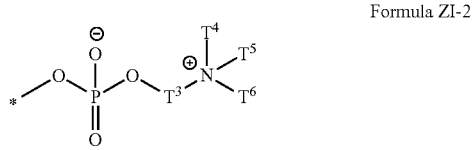

Formula ZI-2 wherein * designates the point of covalent attachment of the zwitterion of Formula ZI-2 to the polymer backbone, T³ is hydrocarbylene, substituted hydrocarbylene, or oxylated alkylene, and T⁴, T⁵ and T⁶ are independently hydrogen, hydrocarbyl, substituted hydrocarbyl or heterocyclo. For example, in this embodiment, T³ may be —(CH₂)ₙ— with n being 1-8. By way of further example, in this embodiment, T⁴, T⁵ and T⁶ may independently be lower alkyl, e.g., methyl, ethyl or propyl. By way of further example, in this embodiment, T³ may be —(CH₂)ₙ— with n being 1-3, and T⁴, T⁵ and T⁶ may independently be lower alkyl, e.g., methyl, ethyl or propyl. By way of further example, in this embodiment, T³ may be —(CH₂)ₙ— with n being 1-3, and one or more of T⁴, T⁵ and T⁶ may be substituted hydrocarbyl such as oligomeric phosphorylcholine (e.g., Formula 9).

In one embodiment, the zwitterionic polymer also contains neutral hydrophilic pendant groups covalently attached, directly or indirectly, to the polymer backbone. Exemplary neutral hydrophilic groups include hydroxy, thiol, oxylated alkyls (e.g., oligoethylene glycol, polyethylene glycol and/or polypropylene glycol), ether, thioether, and the like. In one such specific embodiment, the polymer contains pendant groups comprising alkoxylated moieties corresponding to Formula POA-1:

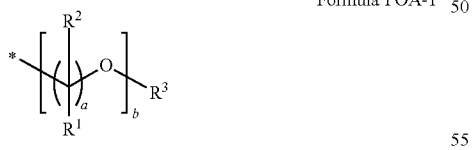

Formula POA-1 wherein a is 1-3, b is 1-8, each R¹ and R² is independently selected from the group consisting of hydrogen, halogen, and optionally substituted lower alkyl, R³ is hydrocarbyl, substituted hydrocarbyl or heterocyclo, and * designates the point of attachment of the moieties corresponding to Formula POA-1 to the remainder of the pendant group and the backbone. By way of example, in one such embodiment, each R¹ and R² are hydrogen, n is 2 or 3. By way of further example, in one such embodiment, each R¹ and R² is hydrogen, n is 2 or 3, and b is 3-5. By way of further example, in one such embodiment, each R¹ and R² is hydrogen, n is 2 or 3, b is 3-5, and R³ is alkyl. In one embodiment, the repeat units are derived from macromonomers containing 2-20 alkylene oxide units.

Neutral Hydrophilic Pendant Groups

In one embodiment, the polymer contains neutral hydrophilic pendant groups covalently attached, directly or indirectly, to the polymer backbone. Exemplary neutral hydrophilic groups include hydroxy, thiol, oxylated alkyls (e.g., oligoethylene glycol, polyethylene glycol and/or polypropylene glycol), ether, thioether, and the like. In one such specific embodiment, the polymer contains pendant groups comprising alkoxylated moieties corresponding to Formula POA-1:

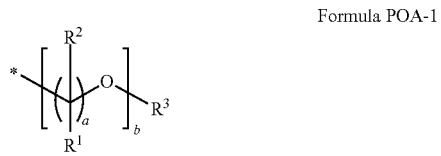

Formula POA-1 wherein a is 1-3, b is 1-8, each R¹ and R² is independently selected from the group consisting of hydrogen, halogen, and optionally substituted lower alkyl, R³ is hydrocarbyl, substituted hydrocarbyl or heterocyclo, and * designates the point of attachment of the moieties corresponding to Formula POA-1 to the remainder of the pendant group and the backbone. By way of example, in one such embodiment, each R¹ and R² are hydrogen, n is 2 or 3. By way of further example, in one such embodiment, each R¹ and R² is hydrogen, n is 2 or 3, and b is 3-5. By way of further example, in one such embodiment, each R¹ and R² is hydrogen, n is 2 or 3, b is 3-5, and R³ is alkyl. In one embodiment, the repeat units are derived from macromonomers containing 2-20 alkylene oxide units.

Repeat Units

In general, homopolymers or copolymers comprising zwitterionic pendant groups, neutral hydrophilic pendant groups, cationic pendant groups and/or anionic pendant groups may be prepared by polymerization of any of a wide range of monomers. In one preferred embodiment, the hydrophilic polymeric material is a homopolymer or copolymer comprising repeat units derived from an olefinic monomer. Thus, for example, in one embodiment the hydrophilic polymeric material comprises repeat units derived from an olefinic monomer and corresponding to Formula 1:

Formula 1 wherein

X¹ and X² are independently hydrogen, hydrocarbyl, substituted hydrocarbyl, heterocyclo, or substituted carbonyl, provided, however, X¹ and X² are not each selected from the group consisting of aryl, heteroaryl, and heterosubstituted carbonyl, X³ is hydrogen, alkyl or substituted alkyl, X⁴ is —OX⁴⁰, —NX⁴¹X⁴², —N⁺X⁴¹X⁴²X⁴³, —SX⁴⁰, aryl, heteroaryl or acyl, X⁴⁰ is hydrogen, hydrocarbyl, substituted hydrocarbyl, heterocyclo or acyl, and $X^{41}$, $X^{42}$ and $X^{43}$ are independently hydrogen, hydrocarbyl, substituted hydrocarbyl or heterocyclo.

In certain embodiments in which the hydrophilic polymeric material comprises repeat units corresponding to Formula 1, it is preferred that $X^4$ of at least a fraction of the repeat units comprise alkoxylated moieties, zwitterionic moieties, anionic moieties, or cationic moieties. In such embodiments, for example, $X^1$ and $X^2$ may be hydrogen, and the polymer comprises repeat units corresponding to Formula 2:

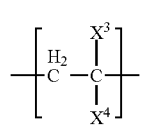

Formula 2 wherein $X^3$ is hydrogen, alkyl or substituted alkyl, and $X^4$ is a pendant group comprising an oxylated alkylene moiety, a zwitterionic moiety, an anionic moiety, or a cationic moiety. For example, $X^3$ may be hydrogen or lower alkyl. By way of further example, $X^4$ may be a pendant group comprising an oxylated alkylene moiety corresponding to Formula POA-1. By way of further example, the repeat unit of Formula 2 may be zwitterionic repeat unit comprising a zwitterionic moiety corresponding to Formula ZI-1, ZI-2, ZI-3, ZI-4, ZI-5, ZI-6A, ZI-6B, or ZI-7. By way of further example, the repeat unit of Formula 2 may be a cationic repeat unit. By way of further example, the repeat unit of Formula 2 may be an anionic repeat unit. By way of further example, $X^3$ may be hydrogen or methyl and $X^4$ may be a pendant group comprising an oxylated alkylene moiety corresponding to Formula POA-1 or a zwitterionic moiety corresponding to Formula ZI-1, ZI-2, ZI-3, ZI-4, ZI-5, ZI-6A, ZI-6B, or ZI-7.

In one presently preferred embodiment, the hydrophilic polymeric material comprises repeat units corresponding to Formula 2 wherein $X^4$ is acyl and the repeat units correspond to Formula 3:

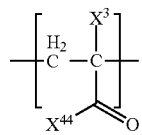

Formula 3 wherein $X^{44}$ comprises an oxylated alkylene moiety, a zwitterionic moiety, an anionic moiety, or a cationic moiety. For example, $X^{44}$ may be $-OX^{45}$, $-NX^{45}X^{46}$ or $-SX^{45}$, wherein $X^{45}$ is a substituted hydrocarbyl or heterocyclo moiety comprising an oxylated alkylene moiety, a zwitterionic moiety, an anionic moiety, or a cationic moiety, and $X^{46}$ is hydrogen, hydrocarbyl, substituted hydrocarbyl or heterocyclo. For example, $X^3$ may be hydrogen or lower alkyl. By way of further example, $X^{44}$ may be $-OX^{45}$, or $-NHX^{45}$. By way of further example, $X^{44}$ may be $-OX^{45}$, or $-NHX^{45}$ wherein $X^{45}$ comprises an oxylated alkylene moiety corresponding to Formula POA-1. By way of further example, $X^{44}$ may be $-OX^{45}$, or $-NHX^{45}$ wherein $X^{45}$ comprises a zwitterionic moiety corresponding to Formula ZI-1, ZI-2, ZI-3, ZI-4, ZI-5, ZI-6A, ZI-6B, or ZI-7. By way of further example, the repeat unit of Formula 3 may be a cationic repeat unit. By way of further example, the repeat unit of Formula 3 may be an anionic repeat unit. By way of further example, $X^3$ may be hydrogen or methyl and $X^{44}$ may comprise an oxylated alkylene moiety corresponding to Formula POA-1 or a zwitterionic moiety corresponding to Formula ZI-1, ZI-2, ZI-3, ZI-4, ZI-5, ZI-6A, ZI-6B, or ZI-7. In one particularly preferred embodiment, the polymer contains repeat units corresponding to Formula 3 and $X^{44}$ is $-O(CH_2)_2N^+(CH_3)_2(CH_2)_nSO_3^-$, $-O(CH_2)_2N^+(CH_3)_2(CH_2)_nCO_2^-$, $-NH(CH_2)_3N^+(CH_3)_2(CH_2)_nCO_2^-$, or $-NH(CH_2)_3N^+(CH_3)_2(CH_2)_nSO_3^-$, wherein n is 1-8. In one embodiment, the polymer contains repeat units corresponding to Formula 3 and $X^{44}$ is $-NH(CH_2)_mN(CH_2)_nCH_3(CH_2)_pSO_3$, $-NH(CH_2)_mN(CH_2)_nCH_3(CH_2)_pCO_2$, $-NH(CH_2)_mN^+[(CH_2)_nCH_3]_2(CH_2)_pSO_3$, $-NH(CH_2)_mN^+[(CH_2)_nCH_3]_2(CH_2)_pCO_2$, $-NH(CH_2)_mNcyclo-(CH_2)_pCO_2$, or $-NH(CH_2)_mNcyclo-(CH_2)_pSO_3$, (Ncyclo is a heterocyclic structure or a heterocyclic derivative containing at least one nitrogen element), wherein m is 1-8; n is 0-5; and p is 1-8. In one embodiment, the polymer contains repeat units corresponding to Formula 3 and $X^{44}$ is $-O(CH_2)_mN(CH_2)_nCH_3(CH_2)_pSO_3$, $-O(CH_2)_mN(CH_2)_nCH_3(CH_2)_pCO_2$, $-O(CH_2)_mN^+[(CH_2)_nCH_3]_2(CH_2)_pSO_3$, $-O(CH_2)N^+[(CH_2)_nCH_3]_2(CH_2)_pCO_2$, $-O(CH_2)_mNcyclo-(CH_2)_pCO_2$, or $-O(CH_2)_mNcyclo-(CH_2)_pSO_3$ wherein m is 1-8; n is 0-5; and p is 1-8. In one embodiment, the polymer contains repeat units corresponding to Formula 3 and $X^{44}$ is $-O(CH_2)_2N^+(CH_3)_2(CH_2)_3SO_3$, $-O(CH_2)_mN^+(CH_3)_2(CH_2)_2CO_2$, $-NH(CH_2)_2N^+(CH_3)_2(CH_2)_3SO_3$, $-NH(CH_2)_2N^+(CH_3)_2(CH_2)_2CO_2$, $-NH(CH_2)_3N^+(CH_3)_2(CH_2)_3SO_3$, $-NH(CH_2)_3N^+(CH_3)_2(CH_2)_2CO_2$, $-O(CH_2)_2N^+(CH_2CH_3)_2(CH_2)_3SO_3$, $-O(CH_2)_2N^+(CH_2CH_3)_2(CH_2)_2CO_2$, $-O(CH_2)_2N^+(CH_2CH_2CH_2CH_3)_2(CH_2)_3SO_3$, $-O(CH_2)_2N^+(CH_2CH_2CH_2CH_3)_2(CH_2)_2CO_2$ or $-NH(CH_2)_3Ncyclo-(CH_2)_3SO_3$.

In one preferred embodiment, the hydrophilic polymeric material is a zwitterionic polymer or copolymer. For example, the hydrophilic polymeric material may comprise carboxybetaine repeat units and/or sulfobetaine repeat units. Optionally, the hydrophilic polymer may contain poly(ethylene oxide) repeat units and/or other neutral olefinic repeat units. Thus, for example, in one preferred embodiment, the hydrophilic polymeric material is a zwitterionic polymer or copolymer comprising the repeat units of Formula 4:

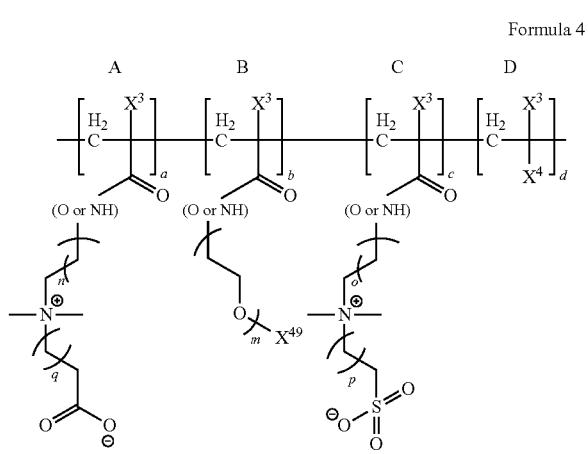

Formula 4 a is 0-1; b is 0-1; c is 0-1; d is 0-1; m is 1-20; n and o are independently 0-11; p and q are independently 0-11; $X^3$ is hydrogen, alkyl or substituted alkyl, $X^4$ is $-OX^{40}$, $-NX^{41}X^{42}$, $-SX^{40}$, aryl, heteroaryl or acyl; $X^{40}$ is hydrogen, hydrocarbyl, substituted hydrocarbyl, heterocyclo or acyl; $X^{41}$ and $X^{42}$ are independently hydrogen, hydrocarbyl, substituted hydrocarbyl or heterocyclo; and $X^{49}$ is hydrogen, hydrocarbyl or substituted hydrocarbyl, provided the sum of a, b, c and d is greater than 0 and $X^4$ of repeat unit D differs from the corresponding pendant group of repeat units A, B and C. In one such embodiment, $X^3$ is hydroxy-substituted alkyl such as hydroxypropyl.

In one embodiment, the hydrophilic polymeric material is a zwitterionic polymer corresponding to Formula 4 comprising repeat units corresponding to the A and/or the C repeat units. For example, in one embodiment, a or c is at least 0.1. By way of further example, in one embodiment a or c is at least 0.2. By way of further example, in one embodiment a or c is at least 0.3. By way of further example, in one embodiment a or c is at least 0.4. By way of further example, in one embodiment a or c is at least 0.5. By way of further example, in one embodiment a or c is at least 0.6. By way of further example, in one embodiment a or c is at least 0.7. By way of further example, in one embodiment a or c is at least 0.8. By way of further example, in one embodiment a or c is at least 0.9. By way of further example, the sum of a and c is at least 0.1. By way of further example, in one embodiment the sum of a and c is at least 0.2. By way of further example, in one embodiment the sum of a and c is at least 0.3. By way of further example, in one embodiment the sum of a and c is at least 0.4. By way of further example, in one embodiment the sum of a and c is at least 0.5. By way of further example, in one embodiment the sum of a and c is at least 0.6. By way of further example, in one embodiment the sum of a and c is at least 0.7. By way of further example, in one embodiment the sum of a and c is at least 0.8. By way of further example, in one embodiment the sum of a and c is at least 0.9.

In one embodiment, the hydrophilic polymeric material is a polymer corresponding to Formula 4 comprising repeat units corresponding to the B and/or D repeat units and, optionally the A and/or C repeat units. For example, in one embodiment the sum of a and c is at least 0.1 and b is at least 0.1. By way of further example, in one embodiment the sum of a and c is at least 0.2 and b is at least 0.1. By way of further example, in one embodiment the sum of a and c is at least 0.3 and b is at least 0.1. By way of further example, in one embodiment the sum of a and c is at least 0.4 and b is at least 0.1. By way of further example, in one embodiment the sum of a and c is at least 0.5 and b is at least 0.1. By way of further example, in one embodiment the sum of a and c is at least 0.6 and b is at least 0.1. By way of further example, in one embodiment the sum of a and c is at least 0.7 and b is at least 0.1. By way of further example, in one embodiment the sum of a and c is at least 0.8 and b is at least 0.1. By way of further example, in one embodiment the sum of a and c is at least 0.9 and b is at least 0.1. By way of further example, in one embodiment the sum of a and c is at least 0.1 and d is at least 0.1. By way of further example, in one embodiment the sum of a and c is at least 0.2 and d is at least 0.1. By way of further example, in one embodiment the sum of a and c is at least 0.3 and d is at least 0.1. By way of further example, in one embodiment the sum of a and c is at least 0.4 and d is at least 0.1. By way of further example, in one embodiment the sum of a and c is at least 0.5 and d is at least 0.1. By way of further example, in one embodiment the sum of a and c is at least 0.6 and d is at least 0.1. By way of further example, in one embodiment the sum of a and c is at least 0.7 and d is at least 0.1. By way of further example, in one embodiment the sum of a and c is at least 0.8 and d is at least 0.1. By way of further example, in one embodiment the sum of a and c is at least 0.9 and d is at least 0.1. By way of further example, in one embodiment the sum of a and c is at least 0.1, b is at least 0.1 and d is at least 0.1. By way of further example, in one embodiment the sum of a and c is at least 0.2, b is at least 0.1 and d is at least 0.1. By way of further example, in one embodiment the sum of a and c is at least 0.3, b is at least 0.1 and d is at least 0.1. By way of further example, in one embodiment the sum of a and c is at least 0.4, b is at least 0.1 and d is at least 0.1. By way of further example, in one embodiment the sum of a and c is at least 0.5, b is at least 0.1 and d is at least 0.1. By way of further example, in one embodiment the sum of a and c is at least 0.6, b is at least 0.1, and d is at least 0.1. By way of further example, in one embodiment the sum of a and c is at least 0.7, b is at least 0.1 and d is at least 0.1. By way of further example, in one embodiment the sum of a and c is at least 0.8, b is at least 0.1 and d is at least 0.1. By way of further example, in one embodiment the sum of a and c is at least 0.9, b is at least 0.1 and d is at least 0.1. In each of these exemplary embodiments, a may be 0, c may be 0, or a and c may each be greater than 0.

In one embodiment, it is preferred that the hydrophilic polymeric material is a zwitterionic polymer comprising repeat units corresponding to the A and/or the C repeat units. For example, in one embodiment the sum of a and c is at least 0.1. By way of further example, in one embodiment the sum of a and c is at least 0.2. By way of further example, in one embodiment the sum of a and c is at least 0.3. By way of further example, in one embodiment the sum of a and c is at least 0.4. By way of further example, in one embodiment the sum of a and c is at least 0.5. By way of further example, in one embodiment the sum of a and c is at least 0.6. By way of further example, in one embodiment the sum of a and c is at least 0.7. By way of further example, in one embodiment the sum of a and c is at least 0.8. By way of further example, in one embodiment the sum of a and c is at least 0.9. By way of further example, in one embodiment the sum of a and c is at least 0.1 and b is at least 0.1. By way of further example, in one embodiment the sum of a and c is at least 0.2 and b is at least 0.1. By way of further example, in one embodiment the sum of a and c is at least 0.3 and b is at least 0.1. By way of further example, in one embodiment the sum of a and c is at least 0.4 and b is at least 0.1. By way of further example, in one embodiment the sum of a and c is at least 0.5 and b is at least 0.1. By way of further example, in one embodiment the sum of a and c is at least 0.6 and b is at least 0.1. By way of further example, in one embodiment the sum of a and c is at least 0.7 and b is at least 0.1. By way of further example, in one embodiment the sum of a and c is at least 0.8 and b is at least 0.1. By way of further example, in one embodiment the sum of a and c is at least 0.9 and b is at least 0.1. By way of further example, in one embodiment the sum of a and c is at least 0.1 and d is at least 0.1. By way of further example, in one embodiment the sum of a and c is at least 0.2 and d is at least 0.1. By way of further example, in one embodiment the sum of a and c is at least 0.3 and d is at least 0.1. By way of further example, in one embodiment the sum of a and c is at least 0.4 and d is at least 0.1. By way of further example, in one embodiment the sum of a and c is at least 0.5 and d is at least 0.1. By way of further example, in one embodiment the sum of a and c is at least 0.6 and d is at least 0.1. By way of further example, in one embodiment the sum of a and c is at least 0.7 and d is at least 0.1. By way of further example, in one embodiment the sum of a and c is at least 0.8 and d is at least 0.1. By way of further example, in one embodiment the sum of a and c is at least 0.9 and d is at least 0.1. By way of further example, in one embodiment the sum of a and c is at least 0.1, b is at least 0.1 and d is at least 0.1. By way of further example, in one embodiment the sum of a and c is at least 0.2, b is at least 0.1 and d is at least 0.1. By way of further example, in one embodiment the sum of a and c is at least 0.3, b is at least 0.1 and d is at least 0.1. By way of further example, in one embodiment the sum of a and c is at least 0.4, b is at least 0.1 and d is at least 0.1. By way of further example, in one embodiment the sum of a and c is at least 0.5, b is at least 0.1 and d is at least 0.1. By way of further example, in one embodiment the sum of a and c is at least 0.6, b is at least 0.1, and d is at least 0.1. By way of further example, in one embodiment the sum of a and c is at least 0.7, b is at least 0.1 and d is at least 0.1. By way of further example, in one embodiment the sum of a and c is at least 0.8, b is at least 0.1 and d is at least 0.1. By way of further example, in one embodiment the sum of a and c is at least 0.9, b is at least 0.1 and d is at least 0.1. In each of these exemplary embodiments, a may be 0, c may be 0, or a and c may each be greater than 0.

In one preferred embodiment, the hydrophilic polymeric material is a zwitterionic polymer or copolymer comprising the repeat units of Formula 4, m is 1-8; $X^3$ is hydrogen, alkyl or substituted alkyl, $X^4$ is —$OX^{40}$, —$NX^{41}X^{42}$, —$SX^{40}$, aryl, heteroaryl or acyl; $X^{40}$ is hydrogen, hydrocarbyl, substituted hydrocarbyl, heterocyclo or acyl; $X^{41}$ and $X^{42}$ are independently hydrogen, hydrocarbyl, substituted hydrocarbyl or heterocyclo; and $X^{49}$ is hydrogen, hydrocarbyl or substituted hydrocarbyl, with the proviso that $X^4$ of the D repeat differs from the corresponding pendant groups of the A, B or C repeat units and a, b, c, and d, in combination, are selected from one of the sets of combinations appearing in Table I:

TABLE I

| Combination | a | b | c | d |
|---|---|---|---|---|
| 1 | 0.1-1.0 | 0.1-0.5 | 0.1-1.0 | 0.1-1.0 |
| 2a | >0 | >0.1 | 0 | 0 |
| 2b | >0 | 0 | 0 | >0.1 |
| 2c | >0 | >0.1 | 0 | >0.1 |
| 3a | >0.1 | >0.1 | 0 | 0 |
| 3b | >0.1 | 0 | 0 | >0.1 |
| 3c | >0.1 | >0.1 | 0 | >0.1 |
| 4a | >0.2 | >0.1 | 0 | 0 |
| 4b | >0.2 | 0 | 0 | >0.1 |
| 4c | >0.2 | >0.1 | 0 | >0.1 |
| 5a | >0.3 | >0.1 | 0 | 0 |
| 5b | >0.3 | 0 | 0 | >0.1 |
| 5c | >0.3 | >0.1 | 0 | >0.1 |
| 6a | >0.4 | >0.1 | 0 | 0 |
| 6b | >0.4 | 0 | 0 | >0.1 |
| 6c | >0.4 | >0.1 | 0 | >0.1 |
| 7a | >0.5 | >0.1 | 0 | 0 |
| 7b | >0.5 | >0 | 0 | >0.1 |
| 7c | >0.5 | >0.1 | 0 | >0.1 |
| 8a | >0.6 | >0.1 | 0 | 0 |
| 8b | >0.6 | 0 | 0 | >0.1 |
| 8c | >0.6 | >0.1 | 0 | >0.1 |
| 9a | >0.7 | >0.1 | 0 | 0 |
| 9b | >0.7 | >0.1 | 0 | >0.1 |
| 9c | >0.7 | 0 | 0 | >0.1 |
| 10a | >0.8 | >0.1 | 0 | 0 |
| 10b | >0.8 | 0 | 0 | >0.1 |
| 10c | >0.8 | >0.1 | 0 | >0.1 |
| 11a | >0.9 | >0.1 | 0 | 0 |
| 11b | >0.9 | 0 | 0 | >0.1 |
| 11c | >0.9 | >0.1 | 0 | >0.1 |
| 12a | 0 | >0.1 | >0 | 0 |
| 12b | 0 | 0 | >0 | >0.1 |
| 12c | 0 | >0.1 | >0 | >0.1 |
| 13a | 0 | >0.1 | >0.1 | 0 |
| 13b | 0 | 0 | >0.1 | >0.1 |
| 13c | 0 | >0.1 | >0.1 | >0.1 |
| 14a | 0 | >0.1 | >0.2 | 0 |
| 14b | 0 | 0 | >0.2 | >0.1 |
| 14c | 0 | >0.1 | >0.2 | >0.1 |
| 15a | 0 | >0.1 | >0.3 | 0 |
| 15b | 0 | 0 | >0.3 | >0.1 |
| 15c | 0 | >0.1 | >0.3 | >0.1 |
| 16a | 0 | >0.1 | >0.4 | 0 |
| 16b | 0 | 0 | >0.4 | >0.1 |
| 16c | 0 | >0.1 | >0.4 | >0.1 |
| 17a | 0 | >0.1 | >0.5 | 0 |
| 17b | 0 | >0 | >0.5 | >0.1 |
| 17c | 0 | >0.1 | >0.5 | >0.1 |
| 18a | 0 | >0.1 | >0.6 | 0 |
| 18b | 0 | 0 | >0.6 | >0.1 |
| 18c | 0 | >0.1 | >0.6 | >0.1 |
| 19a | 0 | >0.1 | >0.7 | 0 |
| 19b | 0 | >0.1 | >0.7 | >0.1 |
| 19c | 0 | 0 | >0.7 | >0.1 |
| 20a | 0 | >0.1 | >0.8 | 0 |
| 20b | 0 | 0 | >0.8 | >0.1 |
| 20c | 0 | >0.1 | >0.8 | >0.1 |
| 21a | 0 | >0.1 | >0.9 | 0 |
| 21b | 0 | 0 | >0.9 | >0.1 |
| 21c | 0 | >0.1 | >0.9 | >0.1 |
| 22a | >0 | >0.1 | >0.7 | 0 |
| 22b | >0 | 0 | >0.7 | >0.1 |
| 22c | >0 | >0.1 | >0.7 | >0.1 |
| 23a | >0.1 | >0.1 | >0.6 | 0 |
| 23b | >0.1 | 0 | >0.6 | >0.1 |
| 23c | >0.1 | >0.1 | >0.6 | >0.1 |
| 24a | >0.2 | >0.1 | >0.5 | 0 |
| 24b | >0.2 | 0 | >0.5 | >0.1 |
| 24c | >0.2 | >0.1 | >0.5 | >0.1 |
| 25a | >0.3 | >0.1 | >0.4 | 0 |
| 25b | >0.3 | 0 | >0.4 | >0.1 |
| 25c | >0.3 | >0.1 | >0.4 | >0.1 |
| 26a | >0.4 | >0.1 | >0.3 | 0 |
| 26b | >0.4 | 0 | >0.3 | >0.1 |
| 26c | >0.4 | >0.1 | >0.3 | >0.1 |
| 27a | >0.5 | >0.1 | >0.2 | 0 |
| 27b | >0.5 | >0 | >0.2 | >0.1 |
| 27c | >0.5 | >0.1 | >0.2 | >0.1 |
| 28a | >0.6 | >0.1 | >0.1 | 0 |
| 28b | >0.6 | 0 | >0.1 | >0.1 |
| 28c | >0.6 | >0.1 | >0.1 | >0.1 |
| 29a | >0.7 | >0.1 | >0 | 0 |
| 29b | >0.7 | >0.1 | >0 | >0.1 |
| 29c | >0.7 | 0 | >0 | >0.1 |

In one embodiment, the hydrophilic polymeric material is a polyampholyte zwitterionic polymer or copolymer comprising repeat units corresponding to repeat unit D of Formula 4. That is, d is greater than 0 and a fraction of the repeat units corresponding to repeat unit D are anionic repeat units ($X^4$ for such units is an anionic pendant group) and a fraction of the repeat units corresponding of Formula 4 are cationic repeat units ($X^4$ for such units is a cationic pendant group). For example, in one such embodiment, d is at least 0.1 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.2 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.3 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.4 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.5 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.6 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.7 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.8 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in one such embodiment, d is at least 0.9 and approximately one-half the repeat units corresponding to repeat unit D are anionic repeat units ($X^4$ for such units is an anionic pendant group) and approximately one-half of the repeat units corresponding of Formula 4 are cationic repeat units ($X^4$ for such units is a cationic pendant group). By way of further example, in each of said examples in this paragraph, the remaining repeat units may correspond to repeat unit A. By way of further example, in each of said examples in this paragraph, the remaining repeat units may correspond to repeat unit B. By way of further example, in each of said examples in this paragraph, the remaining repeat units may correspond to repeat unit C.

More preferably, the hydrophilic polymeric material is a zwitterionic polymer or copolymer comprising repeat units corresponding to repeat unit A and/or repeat unit C of Formula 4.

In certain embodiments, the hydrophilic polymeric material is a homopolymer or copolymer comprising repeat units corresponding to Formula 5, Formula 6, Formula 7, Formula 8, or Formula 9:

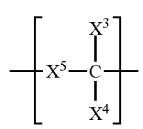

Formula 5

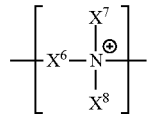

Formula 6

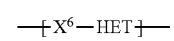

Formula 7

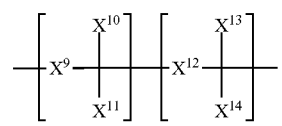

Formula 8

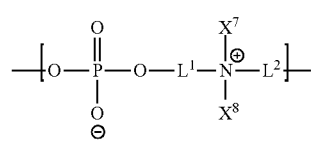

Formula 9

HET is part of a heterocyclic structure,
$X^3$ is hydrogen, alkyl or substituted alkyl,
$X^4$ is $-OX^{40}$, $-NX^{41}X^{42}$, $-SX^{40}$, aryl, heteroaryl or acyl,
$X^5$ is ester, anhydride, imide, amide, ether, thioether, thioester, hydrocarbylene, substituted hydrocarbylene, heterocyclo, urethane, or urea;
$X^6$ is hydrocarbylene, substituted hydrocarbylene, heterocyclo, amide, anhydride, ester, imide, thioester, thioether, urethane, or urea;
$X^7$ is hydrogen, alkyl or substituted alkyl;
$X^8$ is an anionic moiety;
$X^9$ is hydrocarbylene, substituted hydrocarbylene, heterocyclo, amide, anhydride, ester, imide, thioester, thioether, urethane, or urea;
$X^{10}$ is hydrogen, alkyl or substituted alkyl;
$X^{11}$ is a cationic moiety;
$X^{12}$ is hydrocarbylene, substituted hydrocarbylene, heterocyclo, amide, anhydride, ester, imide, thioester, thioether, urethane, or urea;
$X^{13}$ is hydrogen, alkyl or substituted alkyl;
$X^{14}$ is an anionic moiety;
$L^1$ and $L^2$ are independently hydrocarbylene, substituted hydrocarbylene, heterocyclo, amide, anhydride, ester, imide, thioester, thioether, urethane, or urea; and
$X^{40}$ is hydrogen, hydrocarbyl, substituted hydrocarbyl, heterocyclo or acyl, and
$X^{41}$ and $X^{42}$ are independently hydrogen, hydrocarbyl, substituted hydrocarbyl or heterocyclo.

In one embodiment, the hydrophilic polymeric material comprises repeat units corresponding to Formula 7 wherein the heterocycle, HET corresponds to Formulae 10, 11 or 12:

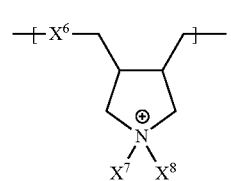

Formula 10

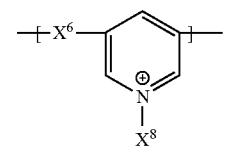

Formula 11

-continued

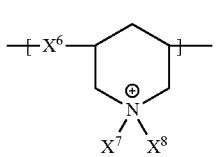

Formula 12 wherein $X^6$ is hydrocarbylene, substituted hydrocarbylene, heterocyclo, amide, anhydride, ester, imide, thioester, thioether, urethane, or urea; $X^7$ is hydrogen, alkyl or substituted alkyl; and $X^8$ is an anionic moiety.

Suitable comonomers include, but are not limited to, acrylates, acrylamides, vinyl compounds, multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams, and combination thereof. In the interests of brevity, exemplary methacrylate monomers are listed below (but it should be understood that analogous acrylate, acrylamide and methacrylamide monomers may be similarly listed and are similarly included):

Charged methacrylates or methacrylates with primary, secondary or tertiary amine groups, such as, 3-sulfopropyl methacrylate potassium salt, (2-dimethylamino)ethyl methacrylate) methyl chloride quaternary salt, [2-(methacryloyloxy)ethyl]trimethyl-ammonium chloride, methacryloyl chloride, [3-(methacryloylamino)propyl]-trimethylammonium chloride), 2-aminoethyl methacrylate hydrochloride, 2-(diethylamino)ethyl methacrylate, 2-(dimethylamino)ethyl methacrylate, 2-(tert-butylamino)ethyl methacrylate, and 2-(tert-butylamino-ethyl methacrylate.

Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, 2-naphthyl methacrylate, 2,2,3,3-tetrafluoropropyl methacrylate, 1,1,1,3,3,3-hexafluoroisopropyl methacrylate, 2,2,2-trifluoroethyl methacrylate, 2,2,3,3,3-pentafluoropropyl methacrylate, 2,2,3,4,4,4-hexafluorobutyl methacrylate, 2,2,3,3,4,4,4-heptafluorobutyl methacrylate, 2,2,3,3,4,4,5,5-octafluoropentyl methacrylate, 3,3,4,4,5,5,6,6,7,7,8,8,8-tridecafluorooctyl methacrylate, and 3,3,4,4,5,5,6,6,7,7,8,8,9,9,10,10,10-heptadecafluorodecyl methacrylate.

Reactive or crosslinkable methacrylates, such as 2-(trimethylsilyloxy)ethyl methacrylate, 3-(trichlorosilyl)propyl methacrylate, 3-(trimethoxysilyl)propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate 3-(dimethylchlorosilyl)propyl methacrylate 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

Other methacrylates, such as ethylene glycol methyl ether methacrylate, di(ethylene glycol) methyl ether methacrylate, ethylene glycol phenyl ether methacrylate, 2-butoxyethyl methacrylate, 2-ethoxyethyl methacrylate, and ethylene glycol dicyclopentenyl ether methacrylate.

In one embodiment, the hydrophilic material is a polymer containing repeat units derived from sulfobetaine-containing and/or carboxybetaine-containing monomers. Examples of monomers include sulfobetaine methacrylate (SBMA), sulfobetaine acrylamide, sulfobetaine methacrylamide, carboxybetaine methacrylate (CBMA), carboxybetaine acrylamide and carboxybetaine methacrylamide. Examples of such polymers include, but are not limited to, poly(carboxybetaine methacrylate) (polyCBMA), poly(carboxybetaine acrylamide), poly(carboxybetaine methacrylamide) poly(sulfobetaine methacrylate) (polySBMA), poly(sulfobetaine acrylamide), and poly(sulfobetaine methacrylamide). In another embodiment, the hydrophilic material polymer is a polymer containing the residue of CBMA or SBMA and one or more additional monomers. The additional monomers can be zwitterionic or non-zwitterionic monomers.

In some embodiments, it is preferred to have use zwitterionic polymers that possess permanently charged groups, which, without being bound by any theory, may improve non-fouling performance because the charged groups are ionically solvated with water. The presence of commonly used groups which can have permanent charges in the zwitterionic polymers can be detected by using XPS to analyze the elements present in the top approximately 1-50 nm of the surface. One representative group commonly used in zwitterions is nitrogen in quaternary amine groups. In sulfobetaine, elemental signal of nitrogen may be approximately equivalent to a signal for sulfur. Further, techniques such as TOF-SIMS may be used to identify zwitterionic groups in the grafted polymer layer. In some preferred embodiments, the grafted polymer layer contains XPS signals of nitrogen, and optionally sulfur.

In general, the grafted polymeric material may comprise repeat units corresponding to any of Formulae 1 to 12. By way of further example, the grafted polymeric material may comprise a zwitterionic polymer. By way of further example, polymeric material may comprise repeat units corresponding to Formula 1. By way of further example, the grafted polymeric material may comprise repeat units corresponding to Formula 2. By way of further example, the grafted polymeric material may comprise repeat units corresponding to Formula 3. By way of further example, the grafted polymeric material may comprise repeat units corresponding to Formula 4. Additionally, the grafted polymeric material may comprise, as pendant groups, any of the pendant groups disclosed herein. Thus, for example, the grafted polymeric material may comprise pendant groups corresponding to any of Formulae ZI-1 to ZI-7 or POA-1. In one particularly preferred embodiment, the grafted polymeric material corresponds to Formula 1 and comprises zwitterionic pendant groups. In another particularly preferred embodiment, the grafted polymeric material corresponds to Formula 3 and comprises sulfobetaine or carboxybetaine pendant groups. In one especially preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In general, the height and any branching of the grafted polymeric material can help to overcome surface irregularities and defects, and increased branching may reduce the ability of fouling materials to penetrate the non-fouling layer.

In one embodiment, the grafted polymeric material is a polymer containing repeat units derived from hydrophilic monomers. For example, in one embodiment at least 30% of the repeat units of the grafted polymeric material are derived from hydrophilic monomers, By way of further example, in one embodiment at least 50% of the repeat units of the grafted polymeric material are derived from hydrophilic monomers, By way of further example, in one embodiment at least 75% of the repeat units of the grafted polymeric material are derived from hydrophilic monomers, By way of further example, in one embodiment at least 90% of the repeat units of the grafted polymeric material are derived from hydrophilic monomers, By way of further example, in one embodiment at least 99% of the repeat units of the grafted polymeric material are derived from hydrophilic monomers, Examples of hydrophilic monomers include acrylic acid, polyvinyl alcohol, 2-hydroxyethyl methacrylate ("HEMA"), phosphorylcholine, oligoethylene glycol, polyethylene glycol, polyvinylpyrrolidone, sulfobetaine methacrylate (SBMA), sulfobetaine acrylamide, sulfobetaine methacrylamide, carboxybetaine methacrylate (CBMA), carboxybetaine acrylamide and carboxybetaine methacrylamide.

In one preferred embodiment, the grafted polymeric material corresponds to Formula 1 and comprises zwitterionic pendant groups and the surface modification has a thickness which is at least equal to the surface roughness of the substrate surface. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers.

In another preferred embodiment, the grafted polymeric material corresponds to Formula 1 and comprises zwitterionic pendant groups and the surface modification, i.e., the grafted polymeric material, has an Average Dry Thickness of at least 50 nm. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and has an Average Dry Thickness of at least about 50 nm, as measured by SEM under vacuum. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an Average Dry Thickness of at least about 50 nm, as measured by SEM under vacuum. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an Average Dry Thickness of at least about 50 nm, as measured by SEM under vacuum. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an Average Dry Thickness of at least about 50 nm, as measured by SEM under vacuum. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an Average Dry Thickness of at least about 50 nm, as measured by SEM under vacuum. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and has an Average Dry Thickness of at least about 50 nm, as measured by SEM under vacuum. By way of further example, in each of the foregoing embodiments, the Average Dry Thickness may be even greater, e.g., at least about 200 nm, at least about 300 nm, at least about 400 nm, or at least about 500 nm.

In another preferred embodiment, the grafted polymeric material corresponds to Formula 1 and comprises zwitterionic pendant groups and the surface modification, i.e., the grafted polymeric material, has a relatively uniform thickness. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the standard deviation of the Average Dry Thickness of the hydrophilic grafted polymer layer not exceed 100% of the Average Dry Thickness of the hydrophilic grafted polymer layer. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the Average Dry Thickness of the hydrophilic grafted polymer layer not exceed 100% of the Average Dry Thickness of the hydrophilic grafted polymer layer. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the Average Dry Thickness of the hydrophilic grafted polymer layer not exceed 100% of the Average Dry Thickness of the hydrophilic grafted polymer layer. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the Average Dry Thickness of the hydrophilic grafted polymer layer not exceed 100% of the Average Dry Thickness of the hydrophilic grafted polymer layer. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the Average Dry Thickness of the hydrophilic grafted polymer layer not exceed 100% of the Average Dry Thickness of the hydrophilic grafted polymer layer. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the standard deviation of the thickness of the hydrophilic grafted polymer layer not exceed 100% of the Average Dry Thickness of the hydrophilic grafted polymer layer. By way of further example, in each of the foregoing embodiments, the standard deviation of thickness may be even less, e.g., less than 50% of the Average Dry Thickness of the hydrophilic grafted polymer layer, less than 20% of the Average Dry Thickness of the hydrophilic grafted polymer layer, or less than 10% of the Average Dry Thickness of the hydrophilic grafted polymer layer.

In another preferred embodiment, the grafted polymeric material corresponds to Formula 1, comprises zwitterionic pendant groups, the substrate surface and the grafted polymeric material, in combination, constitute a modified surface, and the modified surface exhibits a static contact angle of less than 40 degrees. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the modified surface exhibits a static contact angle of less than 25 degrees. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a static contact angle of less than 25 degrees. By way of further example, in each of the foregoing embodiments, the modified surface exhibits a static contact angle may be even less, e.g., less than 24, less than 23, less than 22, less than 21, less than 20, less than 19, less than 18, less than 17, less than 16, or less than 15.

In another preferred embodiment, the grafted polymeric material corresponds to Formula 1, comprises zwitterionic pendant groups and the grafted polymeric material, i.e., the grafted polymer layer, has a volumetric swelling capacity, as measured by the magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM), that is less than 200% of the Average Dry Thickness. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the grafted polymer layer has a volumetric swelling capacity, as measured by the magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM), that is less than 200% of the Average Dry Thickness. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM), that is less than 200% of the Average Dry Thickness. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM), that is less than 200% of the Average Dry Thickness. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM), that is less than 200% of the Average Dry Thickness. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM), that is less than 200% of the Average Dry Thickness. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the grafted polymer layer has a volumetric swelling capacity measured by the magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM), that is less than 200% of the Average Dry Thickness. By way of further example, in each of the foregoing embodiments, the grafted polymer layer has a volumetric swelling capacity that may be less than 200%, e.g., less than 100%, less than 50%, less than 25%, less than 10%, less than 5%, less than 1%, or even 0, as measured by the magnitude of the difference between the Average Dry Thickness of the grafted polymer layer as determined by standard scanning electron microscopy (SEM) or by analyzing the intensity of the chemical signals in the polymer layer, for instance, through the use of ATR-FTIR and the global average humidified thickness of the grafted polymer layer as determined by environmental scanning electron microscopy (ESEM).

In another preferred embodiment, the grafted polymeric material corresponds to Formula 1, comprises zwitterionic pendant groups, the substrate surface and the grafted polymeric material, in combination, constitute a modified surface, and the modified surface exhibits a relatively low affinity for proteins. For example, the modified surface may exhibit a fibrinogen adsorption of less than 125 ng/cm$^2$ in a fibrinogen adsorption assay. By way of further example, in one embodiment the modified surface may exhibit a fibrinogen adsorption of less than 90 ng/cm$^2$ in a fibrinogen adsorption assay. By way of further example, in one embodiment the modified surface may exhibit a fibrinogen adsorption of less than 70 ng/cm$^2$ in a fibrinogen adsorption assay. By way of further example, it is generally preferred that the modified surface exhibit a fibrinogen adsorption of less than 50 ng/cm$^2$ in a fibrinogen adsorption assay. In one such preferred embodiment, the grafted polymeric material corresponds to Formula 3 and comprises sulfobetaine or carboxybetaine pendant groups. In one such preferred embodiment, the grafted polymeric material comprises repeat units derived from sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers. In one such preferred embodiment, polymeric material is a homopolymer of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide monomers and the modified surface exhibits a fibrinogen adsorption of less than 30 ng/cm$^2$. In one such preferred embodiment, the grafted polymeric material is a copolymer, at least 50% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. In one such preferred embodiment, the grafted polymeric material is a copolymer, at least 60% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. In one such preferred embodiment, the grafted polymeric material is a copolymer, at least 70% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. In one such preferred embodiment, the grafted polymeric material is a copolymer, at least 80% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. In one such preferred embodiment, the grafted polymeric material is a copolymer, at least 90% of the monomeric residues of which are residues of sulfobetaine methacrylate, sulfobetaine acrylate, sulfobetaine acrylamide, sulfobetaine methacrylamide, carboxybetaine methacrylate, carboxybetaine acrylate, carboxybetaine acrylamide, or carboxybetaine methacrylamide and the modified surface exhibits a fibrinogen adsorption of less than 30 ng/cm$^2$. By way of further example, in each of the foregoing embodiments, the modified surface exhibits a fibrinogen adsorption that may be less than 20 ng/cm$^2$, e.g., less than 15 ng/cm$^2$, less than 12 ng/cm$^2$, less than less than 10, less than 8 ng/cm$^2$, less than 6 ng/cm$^2$, less than 4, less than 2 ng/cm$^2$, less than 1 ng/cm$^2$, less than 0.5 ng/cm$^2$, or less than less than 0.25 ng/cm$^2$.

A broad range of antimicrobial or antiseptic agents may be incorporated in the substrate or the non-fouling polymer to enhance antimicrobial activity at the surface or be released to provide antimicrobial activity in the environment surrounding the article. Suitable agents include silver metals, silver salts such as silver sulfadiazine, silver oxide, silver carbonate, silver acetate, silver alginate, silver azide, silver citrate, silver lactate, silver nitrate, silver sulfate, silver chloride, silver thiocyanate, silver-sodium-hydrogen-zirconium phosphate, silver sulfadiazine, silver cyclohexanediacetic acid and disilver 2,5-dichloro-3,6-dihydroxy-2,5-cyclohexadiene-1,4-dione, among others, a bismuth salt such as bismuth nitrate, bismuth citrate or bismuth salicylate among others, a zinc salt, a cerium salt, triclosan, combinations of chlorhexidine free base and chlorhexidine acetate, benzalkonium chloride, citrate, povidoneiodine, parachlorometaxylene, gramicidin, polymixin, norfloxacin, tobramycin, sulfamylon, polyhexamethylene biguanide, alexidine, iodine, rifampicin, miconazole, bacitracin, and minocycline, ciprofloxacin, clindamycin, erythromycin, gentamycin, tetracycline and vancomycin.

Biguanide compounds which may be used according to the invention include poly (hexamethylene biguanide) hydrochloride and chlorhexidine compounds. Chlorhexidine is the term denoting the chemical compound 1,6 bis(N5-p-chlorophenyl-N1-biguanido)hexane). Chlorhexidine compounds include chlorhexidine free base ("CHX") as well as chlorhexidine salts, such as chlorhexidine diphosphanilate, chlorhexidine digluconate ("CHG"), chlorhexidine diacetate ("CHA"), chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine mono-diglycolate, chlorhexidine dilactate, chlorhexidine di-a-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxy-napthoate, and chlorhexidine embonate.

Bismuth salts which may be used according to the invention include bismuth nitrate, bismuth citrate, bismuth salicylate, bismuth borate, bismuth mandelate, bismuth palmitate, bismuth benzoate, and bismuth sulfadiazine.

Cerium salts which may be used according to the invention include cerium nitrate and other cerium salts having a water solubility similar to cerium nitrate.

The term silver-containing compound, as used herein, refers to a compound comprising silver, either in the form of a silver atom or a silver ion unlinked or linked to another molecule via a covalent or noncovalent (e.g., ionic) linkage, including but not limited to covalent compounds such as silver sulfadiazine ("AgSD") and silver salts such as silver oxide ("Ag$_2$O"), silver carbonate ("Ag$_2$CO$_3$"), silver deoxycholate, silver salicylate, silver iodide, silver nitrate ("AgNO$_3$"), silver paraaminobenzoate, silver paraaminosalicylate, silver acetylsalicylate, silver ethylenediaminetetraacetic acid ("Ag EDTA"), silver picrate, silver protein, silver citrate, silver lactate and silver laurate.

Zinc salts which may be used according to the invention include zinc acetate and other zinc salts having a water solubility similar to zinc acetate.

The catheter body may comprise one or more permeabilization agents in addition to one or more antimicrobial agents. The permeabilization agents may enhance the penetration of antimicrobials into surrounding tissue. One class of suitable permeabilization agents is vegetable oils. Suitable vegetable oils include almond oil, babassu oil, caster oil, Clark A oil, coconut oil, corn oil, cotton seed oil, jojoba oil, linseed oil, mustard oil, olive oil, palm oil, peanut oil, safflower oil, sesame oil, soybean oil, sunflower-seed oil and wheat germ oil. Another suitable permeabilization agent is *eucalyptus* oil. Suitable permeabilization agents also include terpenes or terpenoids. In one embodiment, the substrate contains 0.01-10 wt % of one or more permeabilization agents and one or more antimicrobial agents. In one embodiment, the substrate contains 0.1-1 wt % of one or more permeabilization agents and one or more antimicrobial agents.

In one embodiment, the catheter comprising as component parts thereof a catheter body and at least one connector, the catheter body having an exterior surface and at least one lumen having an aspect ratio of at least 3:1 and an intraluminal surface comprising a hydrophilic polymer layer thereon, the hydrophilic polymer layer having an Average Dry Thickness wherein the Average Dry Thickness is at least about 200 nanometers, wherein the catheter body comprises 0.01-10 wt % of one or more permeablilization agents and at least one antimicrobial agent.

In some embodiments the catheter body comprises one or more permeabilization agent and a chlorhexidine salt, and a hydrophilic polymer is present on the surface of the catheter. In one embodiment, the catheter body comprises a chlorhexidine salt before a hydrophilic polymer is added. Thereafter, a hydrophilic polymer is added to the catheter surface through either a graft-to or graft from method, and thereafter, the catheter body is swollen with an solvent containing a permeabilization agent which is imbibed into the wall of the catheter. In some embodiments, the hydrophilic polymer is created with a redox chemistry. In some embodiments, the solvent used to imbibe the permeabilization agent is an alcohol, heptane, acetone, or mixes thereof. In preferred embodiments, the solvent is selected to have substantially greater solubility for the permeabilization agent than the for the antimicrobial agent, which may limit the loss of the antimicrobial agent from the device wall while the permeabilization agent is being imbibed. In preferred embodiments, the solubility of the permeabilization agent is at least 3 times greater than the solubility of the antimicrobial agent. In further preferred embodiments, the solubility of the permeabilization agent is at least 10 times greater than the solubility of the antimicrobial agent. In further preferred embodiments, the solubility of the permeabilization agent is at least 25 times greater than the solubility of the antimicrobial agent.

Polymerization

The polymeric surface modifications of the present invention may be formed by synthetic means including, but not limited to, free radical polymerization, ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET), and UV, thermal, or redox free radical initiated polymerization. In a preferred embodiment, the polymer is formed using an oxidizing agent and a reducing agent, in combination, i.e., a redox pair, as the polymerization initiator in a redox free radical polymerization.

In some embodiments, it is preferable that initiators and ligands often used in ATRP such as bromine-containing initiators and ligands such as bipyridine are not used in the process as they may be non-biocompatible at certain levels. In further embodiments, it is preferred not to have a detectable level of bipyridine in the polymer modified article or in aqueous or organic extractions of the polymer modified article. In further embodiments, it is preferred not to have a detectable level of bromine in the polymer modified article or in aqueous or organic extractions of the polymer modified article. Bipyridine and bromine can be detected with HPLC or UV analysis.

The general procedure described herein can be modified as necessary to accommodate different substrate materials, initiators systems, and/or monomer compositions and to incorporate high concentrations of the initiator into and/or onto the substrate or undercoating layer. High initiator concentrations may result in highly densely coated surfaces which improves the non-fouling activity of the composition. For example, highly densely coated surfaces contain polymer chains that reduce penetration of fouling molecules into the coating. Without being bound to any particular theory it is presently theorized that a reservoir of initiator incorporated in the substrate may enhance re-initiation and branching of hydrophilic polymer from the surface and near the surface of the substrate. This re-initiation, in turn, may increase the thickness of the hydrophilic polymer (in other words, the distance the hydrophilic polymer stretches above the substrate in a direction normal to the substrate surface) as well as the degree of branching.

In general, and as described in greater detail elsewhere herein, incorporation of initiator into the substrate enables polymeric material to be grafted from the substrate surface and from within the near-surface zone beneath the substrate surface. In general, however, it is preferred that the grafted polymeric material not extend too far into the substrate; thus, in one embodiment grafted polymeric material is present in the near-surface zone but not at greater depths, i.e., not in the substrate bulk. The maximum depth to which near-surface zone extends, i.e., the distance of the lower boundary of the near-surface zone as measured from the substrate surface is, at least in part, a function of the initiator and the technique used to incorporate initiator in the substrate. Typically, however, it is generally preferred that the lower boundary not be greater than 20 micrometers from the substrate surface. By way of example, the lower boundary may not be greater than 15 micrometers from the substrate surface. By way of further example, the lower boundary may not be greater than 10 micrometers from the substrate surface. Similarly, the minimum depth of near-surface zone, i.e., the distance of the upper boundary of the near-surface zone from the substrate surface is, at least in part, also a function of the initiator and the technique used to incorporate initiator in the substrate. Typically, however, the upper boundary will be at least 0.1 micrometers from the substrate surface. By way of example, the upper boundary may be at least 0.2 micrometers from the substrate surface. By way of further example, the upper boundary may be at least 0.3 micrometers from the substrate surface.

In an alternative embodiment, a redox process is used that does not require imbibing of an initiator into the device. For example, potassium persulfate may be added in combination with a hydrophilic monomer to graft the monomer from the substrate surface. In another embodiment, Fenton's reagent is added in combination with a hydrophilic monomer to graft the monomer from the substrate surface.

The quality of the surface modification formed in the polymerization process is, at least in part, influenced by the quality of the surface of the substrate prior to polymerization. For example, prior to polymerization, the surface may be contaminated, intentionally or otherwise, with particles, waxes and other compositions that may remain on the surface of the substrate as an artifact of the manufacturing process, subsequent handling of the substrate, and/or as part of the intended substrate composition. The substrate surface may also include significant surface roughness, physical defects such as scratches, pinholes, or voids, and chemical defects, such as particle(s) of radiopacifing agents (such as barium sulfate, bismuth oxychloride, bismuth subcarbonate, bismuth trioxide, lanthanum oxide, tantalum pentoxide, and metallic gold, silver, platinum, palladium, tungsten, and tantalum) that are only partially contained within the substrate. For example, substrates containing barium sulfate typically have some barium sulfate particles that are partially contained within the substrate and partially exposed; the exposed portions of such barium sulfate particles may extend from the surface of a substrate to a height of as much as 1 micrometer (as measured from the surface of the substrate using SEM).

In accordance with one embodiment, the substrate surface (i.e., the catheter or one or more components thereof) is preferably pre-treated prior to polymerization. For example, the substrate surface may be cleaned using water, solvents, surfactants, enzymes, or other cleaning solutions or gases to remove particles, waxes or other foreign compositions that may be on or near the surface of the substrate. Alternatively, or additionally, the substrate surface may be mechanically, chemically or chemomechanically treated to reduce the incidence and/or the severity of physical and chemical defects.

In one embodiment, the substrate is treated prior to polymerization with a composition such as an acid, base, chelator or reactant that dissolves or chemically reacts with and reduces the concentration of any compositions that are included as chemical defects, or even swells the substrate allowing the particles to be released from the substrate. For example, exposed portions of barium sulfate particles may be partially or completely dissolved using a mineral or organic acid and optionally, a chelator. In one such exemplary embodiment, polyurethane comprising particles of barium sulfate may be treated with hydrochloric acid to at least partially remove exposed barium sulfate particles.

In one embodiment, the substrate is treated prior to polymerization with a surfactant to remove particles, waxes or other foreign compositions that may be on or near the surface of the substrate. Some preferred surfactants include anionic surfactants, such as alkyl sulfates: ammonium lauryl sulfate, sodium lauryl sulfate (SDS, sodium dodecyl sulfate, another name for the compound); alkyl ether sulfates: sodium laureth sulfate, also known as sodium lauryl ether sulfate (SLES), sodium myreth sulfate; sulfonates: for example docusates: dioctyl sodium sulfosuccinate; sulfonate fluorosurfactants: perfluorooctanesulfonate (PFOS), perfluorobutanesulfonate; alkyl benzene sulfonates; phosphates: for example alkyl aryl ether phosphate, alkyl ether phosphate; carboxylates: for example alkyl carboxylates: fatty acid salts (soaps): sodium stearate; sodium lauroyl sarcosinate; carboxylate fluorosurfactants: perfluorononanoate, perfluorooctanoate (PFOA or PFO). Some preferred surfactants also include cationic surfactants, such as octenidine dihydrochloride; alkyltrimethylammonium salts: cetyl trimethylammonium bromide (CTAB) a.k.a. hexadecyl trimethyl ammonium bromide, cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB). Some preferred surfactants also include zwitterionic (amphoteric) surfactants: such as CHAPS (3-[(3-Cholamidopropyl)dimethylammonio]-1-propanesulfonate); cocamidopropyl hydroxysultaine; amino acids; Imino acids; cocamidopropyl betaine; lecithin. Some preferred surfactants also include nonionic surfactants such as fatty alcohols: cetyl alcohol, stearyl alcohol, cetostearyl alcohol (consisting predominantly of cetyl and stearyl alcohols), oleyl alcohol; polyoxyethylene glycol alkyl ethers (Brij): $CH_3(CH_2)_{10-16}(OC_2H_4)_{1-25}OH$: octaethylene glycol monododecyl ether, pentaethylene glycol monododecyl ether; Polyoxypropylene glycol alkyl ethers: $CH_3(CH_2)_{10-16}(OC_3H_6)_{1-25}OH$; Glucoside alkyl ethers: $CH_3(CH_2)_{10-16}(O\text{-Glucoside})_{1-3}OH$; Decyl glucoside, Lauryl glucoside, Octyl glucoside; Polyoxyethylene glycol octylphenol ethers: $C_8H_{17}(C_6H_4)(OC_2H_4)_{1-25}OH$; Triton X-100; Polyoxyethylene glycol alkylphenol ethers: $C_9H_{19}(C_6H_4)(OC_2H_4)_{1-25}OH$: Nonoxynol-9; Glycerol alkyl esters: Glyceryl laurate; Polyoxyethylene glycol sorbitan alkyl esters: Polysorbates; Sorbitan alkyl esters: Spans; Cocamide MEA, cocamide DEA; Dodecyldimethylamine oxide; Block copolymers of polyethylene glycol and polypropylene glycol: Poloxamers.

Alternatively, or additionally, the substrate may be chemically, mechanically or chemomechanically polished prior to polymerization to reduce surface roughness, reduce the incidence and/or severity of cracks, pinholes and other structural defects in the surface of the catheter (or a component thereof). For example, the substrate may be solvent polished by exposing the substrate to a vapor of a solvent such as chloroform, dioxane or tetrahydrofuran. After polishing the substrate surface preferably has a global average $R_{rms}$ surface roughness that is less than the global average $R_{rms}$ surface roughness of the unpolished substrate. By way of further example, in one embodiment the polished substrate surface has a global average $R_{rms}$ surface roughness that is no more than 90% of the global average $R_{rms}$ surface roughness of the unpolished substrate surface. By way of further example, in one embodiment the polished substrate surface has a global average $R_{rms}$ surface roughness that is no more than 75% of the global average $R_{rms}$ surface roughness of the unpolished substrate surface. By way of further example, in one embodiment the polished substrate surface has a global average $R_{rms}$ surface roughness that is no more than 50% of the global average $R_{rms}$ surface roughness of the unpolished substrate surface.

Alternatively, or additionally, in one embodiment the substrate is precoated prior to polymerization with any of the compositions identified herein as a precoating or undercoating compositions to cover physical defects and/or reduce the surface roughness of the substrate surface. In general, the precoat preferably has an average thickness that equals or exceeds the global average $R_{rms}$ surface roughness of the uncoated substrate. For example, in one embodiment, the precoat has an average thickness that is at least 110% of the global average $R_{rms}$ surface roughness of the uncoated substrate. By way of further example, in one embodiment, the precoat has an average thickness that is at least 200% of the global average $R_{rms}$ surface roughness of the uncoated substrate. By way of further example, in one embodiment, the precoat has an average thickness that is at least 300% of the global average $R_{rms}$ surface roughness of the uncoated substrate. By way of further example, in one embodiment, the precoat has an average thickness that is at least 400% of the global average $R_{rms}$ surface roughness of the uncoated substrate. In addition, the precoating preferably reduces the global average $R_{rms}$ surface roughness of the substrate surface. Stated differently, the precoated substrate surface preferably has an average thickness that equals or exceeds the global average $R_{rms}$ surface roughness of the uncoated substrate and a global average $R_{rms}$ surface roughness that is less than the global average $R_{rms}$ surface roughness of the substrate prior to the application of the precoat. For example, in one embodiment the precoated substrate surface has an average thickness that is at least 110% of the global average $R_{rms}$ surface roughness of the uncoated substrate and a global average $R_{rms}$ surface roughness that is no more than 90% of the global average $R_{rms}$ surface roughness of the substrate prior to the application of the precoat. By way of further example, in one embodiment the precoated substrate surface has an average thickness that is at least 110% of the global average $R_{rms}$ surface roughness of the uncoated substrate and a global average $R_{rms}$ surface roughness that is no more than 75% of the global average $R_{rms}$ surface roughness of the substrate prior to the application of the precoat. By way of further example, in one embodiment the precoated substrate surface has an average thickness that is at least 110% of the global average $R_{rms}$ surface roughness of the uncoated substrate and a global average $R_{rms}$ surface roughness that is no more than 50% of the global average $R_{rms}$ surface roughness of the substrate prior to the application of the precoat.

Regardless of the pre-treatment steps, or even whether pre-treatment steps are employed, the surface of the substrate from which the hydrophilic material is to be grafted has a global average $R_{rms}$ surface roughness that is preferably no more than 100 nm. In certain embodiments, the surface is even smoother. For example, the surface may have a global average $R_{rms}$ surface roughness of less than 50 nm. In some embodiments, the surface may have a global average $R_{rms}$ surface roughness of less than 20 nm.

Additionally, or alternatively, and regardless of the pre-treatment steps, or even whether pre-treatment steps are employed, the surface of the substrate from which the hydrophilic material is to be grafted has a visually observable surface defect density (i.e., visually observable number over a field size of 20×20 micrometers) of defects having a size (i.e., a longest dimension) greater than about 0.5 micrometers that is less than 0.1 defects/$\mu m^2$. For example, the surface of the substrate from which the hydrophilic material is to be grafted may have a surface defect density of defects having a size greater than about 0.5 micrometers that is less than 0.05 defects/$\mu m^2$. By way of further example, the surface of the substrate from which the hydrophilic material is to be grafted may have a surface defect density of defects having a size greater than about 0.5 micrometers that is less than 0.01 defects/$\mu m^2$. By way of further example, the surface of the substrate from which the hydrophilic material is to be grafted may have a surface defect density of defects having a size greater than about 0.5 micrometers that is less than 0.002 defects/$\mu m^2$. By way of further example, the surface of the substrate from which the hydrophilic material is to be grafted may have a surface defect density of defects having a size greater than about 0.5 micrometers that is less than 0.001 defects/$\mu m^2$.

In one presently preferred embodiment, the substrate is precoated with any of the precoating or undercoating materials described elsewhere herein. In one such embodiment, the precoat typically has an average thickness of at least about 100 nm. In some embodiments, the precoat will be substantially thicker; for example, the precoat may have an average thickness of as much as 500 micrometers. In general, however, the precoat will be thinner. For example, the precoat may have an average thickness of about 1-50 micrometers. By way of further example, the precoat may have an average thickness of about 10-30 micrometers.

In some instances, the substrate will have a complex shape or geometry with intraluminal and exterior surfaces to be coated. For example, multi-lumen catheters have an exterior surface and two or more longitudinal lumens that may be coated. Polymeric primer coatings may be applied by simultaneously dipping the external portion in a polymer solution or dispersion to coat the external portion and flowing a polymer solution or dispersion through the intraluminal portion to coat the intraluminal portion. Coating application parameters utilized to effect coating control include the solvent system, percent solids and viscosity, and cure temperature and time. Suitable solvents for the polymer primer layer include, but are not limited to, alcohols, such as methanol or ethanol. Application and cure temperature can vary, for example between ambient and 50° C. so as not to affect physical properties of the underlying substrate, for example, a polyurethane substrate. Solids content can vary between 0.5-10%, with solution viscosity no higher than 12 cP for ease of handling and application.

The average thickness of a polymeric surface modification or coating on a substrate can be approximated using attenuated total reflectance (ATR) infrared spectrometry if the infrared spectra and refractive indices of the typical polymeric surface material and the typical substrate material can be determined independently and if the range of the modification or coating thickness is between 10 nm and 5000 nm. A matrix of synthetic infrared absorbance spectra can be constructed using the principal component spectra (those of the coating material and the substrate material) and Beer's law ($A=cbC$) where b, the optical pathlength, is replaced by the exponentially decaying and wavelength dependent depth of penetration of the ATR evanescent wave. An empirically measured sample is then compared across all the synthetic spectra in the matrix and the closest match, determined by the minimum n-dimensional cosine statistical distance, is the one of the sample's polymeric surface modification or coating thickness.

In one embodiment, for example, the average thickness of a homopolymeric SBMA (N-(3-sulfpropyl)-n-methacryloxyethyl-n,n-dimethylammonium betaine) hydrogel surface modification or coating on a polyetherurethane plus 10% to 50% $BaSO_4$ substrate can be determined using attenuated total reflectance (ATR) infrared spectrometry if the range of the modification or coating thickness is between 10 nm and 5000 nm and the $BaSO_4$ content of the substrate is constant to within +1-5%. The value of the absorbance of the vibrational SO3 stretch at 1037.0 $cm^{-1}$ (point baseline corrected by subtracting the absorbance value at 994.7 $cm^{-1}$) divided by the value of the absorbance of the urethane peak at 1309.5 $cm^{-1}$ (point baseline corrected by subtracting the absorbance value at 1340.0 $cm^{-1}$) equals a value relative to the concentration of SBMA present. By taking the natural log of the relative value, adding 0.1641 and then multiplying by 500 yields a value that correlates to the thickness of the homopolymeric hydrogel surface modification or coating as determined by the synthetic ATR IR matrix described above.

By way of further example, the average thickness of a homopolymeric SBMA (N-(3-sulfpropyl)-n-methacryloxyethyl-n,n-dimethylammonium betaine) hydrogel surface modification or coating on a polyetherurethane substrate can be determined using attenuated total reflectance (ATR) infrared spectrometry if the range of the modification or coating thickness is between 10 nm and 5000 nm. The value of the absorbance of the vibrational SO3 stretch at 1037.0 $cm^{-1}$ (point baseline corrected by subtracting the absorbance value at 994.7 $cm^{-1}$) divided by the value of the absorbance of the urethane peak at 1309.5 $cm^{-1}$ (point baseline corrected by subtracting the absorbance value at 1340.0 $cm^{-1}$) equals a value relative to the concentration of SBMA present. By taking the natural log of the relative value, adding 0.9899 and then multiplying by 500 yields a value that correlates to the thickness of the homopolymeric hydrogel surface modification or coating as determined by the synthetic ATR IR matrix described above.

In a preferred embodiment, some consideration is given to the combined thickness of the undercoating and the grafted polymer layer. For example, it is generally preferred that the undercoating and the grafted polymer not materially change the dimensions of the components of a devices, such as lumen diameters. Thus, in some embodiments, the combined Average Dry Thickness of the undercoating and the grafted polymer layer is <1% of the diameter of a catheter lumen in which it is applied. In some embodiments, the Average Dry Thickness of the undercoating and the grafted polymer layer is <0.5% of the diameter of a catheter lumen in which it is applied. In some embodiments, the Average Dry Thickness of the undercoating and the grafted polymer layer is <0.25% of the diameter of a catheter lumen in which it is applied. In further embodiments, the Average Dry Thickness of the undercoating and the grafted polymer layer is <0.1% of the diameter of a catheter lumen in which it is applied. In certain embodiments, the Average Dry Thickness of the undercoating and the grafted polymer layer is <0.05% of the diameter of a catheter lumen in which it is applied. In further embodiments, the Average Dry Thickness of the undercoating and the grafted polymer layer is <0.01% of the diameter of a catheter lumen in which it is applied. In further embodiments, the Average Dry Thickness of the undercoating and the grafted polymer layer is <0.001% of the diameter of a catheter lumen in which it is applied.

To induce small polymerization initiator molecules to concentrate at or near the substrate surface, where polymerization is initiated and propagated, polymerization mixture solvent systems with surface tensions of a magnitude differing from the surface energy of the substrate and one or more polymerization initiators having limited solubility in the polymerization mixture solvent system are selected. The surfaces of the substrate from which the hydrophilic material is to be grafted may be hydrophobic or hydrophilic, and the polymerization mixture solvent system may be aqueous, comprise polar organic solvents, aqueous mixtures of polar organic solvents, or aqueous mixtures of any organic compound designed to modify the surface tension of aqueous solutions. Optionally, for hydrophobic substrates, hydrophobic initiator(s) and hydrophilic solvent systems, e.g., aqueous media are selected. Preferably, if the substrate is hydrophilic, at least one hydrophilic initiator and a non-polar organic solvent system is selected.

Preferably, the catheter substrate (or at least the portion of the catheter substrate into which the polymerization initiator is incorporated) is not significantly swelled by the polymerization mixture (e.g., by the polymerization mixture solvent system, the polymerization monomers, or both) and the initiator(s) incorporated into the substrate has/have limited solubility in the solvent system. As a result, the interface between substrate surface and the polymerization mixture can have a relatively high local concentration of initiator(s) to initiate hydrophilic polymer growth from or near the substrate surface and to (re)initiate polymer growth from the grafted hydrophilic polymer. Without being bound to any particular theory, it is presently believed that this approach leads to the grafting of a relatively highly branched hydrophilic polymer from the substrate.

In a preferred embodiment, the substrate polymer from which the hydrophilic polymer will be grafted will not swell more than 30% by volume at 25° C. under equilibrium conditions in the polymerization mixture solvent system. In certain embodiments, the substrate polymer from which the hydrophilic polymer will be grafted will not swell more than 15% by volume at 25° C. under equilibrium conditions in the polymerization mixture solvent system. In certain embodiments, the substrate polymer from which the hydrophilic polymer will be grafted will not swell more than 5% by volume at 25° C. under equilibrium conditions in the polymerization mixture solvent system. In certain embodiments, the substrate polymer from which the hydrophilic polymer will be grafted will not swell or may even shrink at 25° C. under equilibrium conditions in the polymerization mixture solvent system. As previously noted, the substrate may be a composite of materials. In such instances, it is preferred that the near-surface region of the substrate into which the polymerization initiator is incorporated satisfy the swelling criteria recited herein. For example, in those embodiments in which the substrate comprises a coating of a precoat material overlying a metal, ceramic, glass or semi-metallic material, it is preferred that the coating of the precoat material not swell more than 30% by volume at 25° C. under equilibrium conditions in the polymerization mixture solvent system.

The initiator(s) incorporated into the substrate preferably have limited solubility in the solvent system comprised by the polymerization mixture and include any of the initiators identified herein. In general, it is preferred that the incorporated initiator(s) have a 10 hour T1/2 decomposition temperature of 25-175° C. In one particular embodiment, the incorporated initiator(s) have a 10 hour T1/2 decomposition temperature of 70-130° C. Advantageously, having a 10 hour T1/2 decomposition temperature of 70-130° C. tends to increase the density of interfacial initiation events from the redox reaction and effectively outcompete thermal initiation.

As described elsewhere herein, the initiator may comprise a redox pair; in such embodiments, at least one member of such pair have such a limited solubility in the polymerization mixture solvent system. In one embodiment, both members of the redox pair have limited solubility in the polymerization mixture solvent system. In an alternative embodiment, one member of the pair is soluble in the polymerization mixture solvent system but the other has limited solubility in the polymerization mixture solvent system. Without being bound to any particular theory, it is presently believed that when one member of a redox pair is soluble in the polymerization mixture solvent system and the other has limited solubility in the polymerization mixture solvent system, the two are phase separated and initiation is enhanced at the interface of the two phases which tends to decrease solution polymerization and increase grafting at or near the substrate surface. Thus, for example, either member of the redox pair may be hydrophobic and either member of the pair may be hydrophilic, provided at least one of the members has limited solubility in the polymerization mixture solvent system. In one preferred embodiment, a hydrophobic oxidizer is paired with a hydrophilic reducing agent. In another preferred embodiment, a hydrophilic oxidizer is paired with a hydrophobic reducing agent. For example, in one embodiment, the redox pair comprises a peroxide and a reducing agent wherein the peroxide has limited solubility in the polymerization solvent system and the reducing agent has high solubility in the polymerization solvent system. By way of further example, in certain embodiments, the peroxide has a log P partition coefficient greater than or equal to 3 for hydrophobic substrates and phases and a log P partition coefficient less than 3 for hydrophilic substrates and phases. By way of further example, in certain embodiments, the peroxide has a log P partition coefficient greater than or equal to 5 for hydrophobic substrates and phases and a log P partition coefficient less than 1 for hydrophilic substrates and phases. By way of further example, in certain embodiments, the peroxide has a log P partition coefficient greater than or equal to 7 for hydrophobic substrates and phases and a log P partition coefficient less than −1 for hydrophilic substrates and phases. By way of further example, in certain embodiments, the peroxide has a log P partition coefficient greater than or equal to 9 for hydrophobic substrates and phases and a log P partition coefficient less than −3 for hydrophilic substrates and phases.

In one embodiment, an initiator is incorporated into the substrate by initially incorporating an initiator-precursor into the substrate and activating the initiator-precursor to an initiator.

In accordance with one aspect of the present invention, the polymerization initiator(s) may be incorporated into and/or onto the substrate by various techniques. In one such method, the substrate (including substrates having precoat or undercoat as previously described) is imbibed with the polymerization initiator; that is, the polymerization initiator is absorbed into the substrate. In one embodiment, the initiator(s), i.e., an initiator or a mixture of different initiators, is introduced into and/or onto the substrate's surface by physio-adsorption, wherein the initiator is dissolved in a solvent or combination of solvents and the substrate (with or without an undercoating layer) is submerged in the mixture for a time and at a temperature to achieve sufficient absorption by the substrate. The substrate is allowed to swell ultimately imbibing initiator into the substrate. In general, the amount of initiator incorporated into a substrate during the soak will, at least in part, be a function of the, solubility of the initiator in the solvent system, solubility of the initiator in the substrate as well as the soak time, temperature and concentration of the initiator in the solution, as well as the chemical composition of the substrate and the initiator.

The quantity of initiator introduced to the substrate can be controlled by changing the concentration of the initiator in the solvent solution and/or by changing the amount of time the substrate is allowed to soak in the initiator solution during one initiator imbibing period or by repeating any number of initiator imbibing periods as required. Temperature is not narrowly critical, with temperatures in the range of room temperature to elevated temperatures being typical. When utilizing multiple periods of initiator imbibing, the initiator used in the subsequent imbibing periods can be the same as, different from, or a mixture with the initiator used in the previous initiator imbibing period. In general, the substrate is immersed in the initiator-containing solution for at least several seconds before polymerization is initiated. In some embodiments, the substrate is immersed in the initiator-containing solution for longer times. For example, the substrate may be immersed in the initiator-containing solution for at least several minutes. By way of further example, the substrate may be immersed in the initiator-containing solution for at least about 15 minutes before polymerization is initiated. In some embodiments, the substrate will be immersed in the initiator-containing solution for at least 1 hour at room temperature or elevated temperatures for initiators having a 10 hour T1/2 decomposition temperature of 70-130° C. before polymerization is initiated. In further embodiments, the substrate will be immersed in the initiator-containing solution for at least 2 hour before polymerization is initiated. In yet further embodiments, the substrate will be immersed in the initiator-containing solution for at least 16 hour before polymerization is initiated. Depending upon the time, temperature and concentration of initiator in the initiator-containing solution, a concentration gradient of initiator in the substrate may be established. In some embodiments, it may be preferable to have a higher concentration of initiator in the substrate nearer to the surface. As noted, the initiator may be present in a range of concentrations in the initiator-containing solution. In general, the concentration of the initiator in the initiator-containing solution will be at least 0.01% by weight. For example, in some embodiments, the concentration of the initiator will generally be at least 0.1% by weight. In some embodiments, the concentration will be even greater, e.g., at least 0.5% by weight. In some embodiments, the concentration will be even greater, e.g., at least 1% by weight. In some embodiments, the concentration will be even greater, e.g., at least 10% by weight. In certain exemplary embodiments, the concentration of the initiator in the initiator-containing solution will be in the range of about 0.2 to about 1% by weight. In certain exemplary embodiments, the concentration of the initiator in the initiator-containing solution will be in the range of about 0.2 to about 10% by weight. In certain exemplary embodiments, the concentration of the initiator in the initiator-containing solution will be in the range of about 0.5 to about 5% by weight. In certain exemplary embodiments, the concentration of the initiator in the initiator-containing solution will be in the range of about 0.75 to about 3% by weight. In each of these embodiments, the initiator is preferably one of the UV, thermal or redox initiators described elsewhere herein.

As a result of the imbibing process, the imbibed substrate may contain about 0.001% by weight initiator. In some embodiments, the imbibed substrate will contain greater amounts of initiator, e.g., at least about 0.01% by weight. For example, in some embodiments the imbibed substrate will contain at least about 0.1% by weight. By way of further example, in some embodiments the imbibed substrate will contain about 0.05% to about 2% by weight initiator. By way of further example, in some embodiments the imbibed substrate will contain about 0.1% to about 1% by weight initiator. By way of further example, in some embodiments the imbibed substrate will contain about 0.2% to about 0.5% by weight initiator. By way of further example, in some embodiments the imbibed substrate will contain about 1% to about 10% by weight initiator. Typically, however, the imbibed substrate will contain less than about 20% by weight initiator. In each of these embodiments, the initiator is preferably one of the UV, thermal or redox initiators described elsewhere herein. The solvent used to imbibe the substrate with initiator may have the capacity to swell the substrate (or at least the portion of the substrate to be imbibed with initiator) to various degrees. Typically, the imbibing solvent has a capacity to swell the substrate (or at least the portion of the substrate to be imbibed with initiator) less than 900% by volume at room temperature and ambient pressure. For example, in one such embodiment, the imbibing solvent has a capacity to swell the substrate (or at least the portion of the substrate to be imbibed with initiator) less than 750% by volume. By way of further example, in one such embodiment, the imbibing solvent has a capacity to swell the substrate (or at least the portion of the substrate to be imbibed with initiator) less than 500% by volume. By way of further example, in one such embodiment, the imbibing solvent has a capacity to swell the substrate (or at least the portion of the substrate to be imbibed with initiator) less than 250% by volume. By way of further example, in one such embodiment, the imbibing solvent has a capacity to swell the substrate (or at least the portion of the substrate to be imbibed with initiator) less than 100% by volume. By way of further example, in one such embodiment, the imbibing solvent has a capacity to swell the substrate (or at least the portion of the substrate to be imbibed with initiator) less than 100% by volume. By way of further example, in one such embodiment, the imbibing solvent has a capacity to swell the substrate (or at least the portion of the substrate to be imbibed with initiator) less than 25% by volume.

In a preferred embodiment, the imbibed substrate is preferably washed using a solvent, optionally with a solvent that swells that substrate, and optionally dried. In other embodiments, the substrate is washed with solvents, which may be the same or different from the imbibing solvents, or the substrate may not be washed. For example, the wash solvent may swell the substrate, shrink the substrate, or neither. In one embodiment, the substrate is dried, partially dried or not dried. Optionally, there may be a solvent exchange.

In an alternative method, the initiator(s) is/are incorporated into the substrate by co-deposition of the initiator(s) as a component of a coating, i.e., a precoating or undercoating as described herein, on the surface of the substrate. For example, a thin film of polymer and initiator are deposited onto the substrate by dipping the substrate in a solution of initiator(s) and polymer. Alternatively, a precoat layer of a flowable mixture of the initiator(s) and a second material such as a polymeric material are deposited onto the surface of the substrate.

In one embodiment, the amount of initiator co-deposited with the polymer is relatively great. In certain embodiments, for example, the weight ratio of initiator to polymer co-deposited will be at least 1:1000, respectively. In some embodiments, the weight ratio of initiator to polymer co-deposited will be even greater, e.g., at least 1:100, 1:10, 1:1, 10:1, 100:1, or 1000:1 respectively. Typically, the ratio of initiator to polymer will be in the range of about 1:1 to about 20:1. In addition, the co-deposited layers (i.e., the layers containing co-deposited initiator and polymer) will have a thickness of at least 100 nm. For example, in one embodiment, the co-deposited layer will have a thickness of about 100 nm to about 500 micrometers. In each of these embodiments, the initiator is preferably one of the UV, thermal or redox initiators described elsewhere herein.

In certain preferred embodiments, the co-deposited layer will contain, as the co-deposited polymer, polyurethane, polystyrene, polyester, sol-gels, or a combination thereof. Thus, for example, in one embodiment, the co-deposited layer will have a thickness of about 100 nm to about 50 micrometers, and the weight ratio of initiator to polymer in the co-deposited layer will be at least 1:1000, respectively. In certain more specific embodiments, the co-deposited layer will contain polyurethane as the co-deposited polymer, and will have a thickness of about 1-50 micrometers. By way of further example, the co-deposited layer may have an average thickness of about 10-30 micrometers. By way of further example, in each of these exemplary embodiments the co-deposited layer may have a weight ratio of initiator to polymer of about 1:1,000 to about 20:1, respectively. In addition, in each of these exemplary embodiments, the initiator is preferably one of the UV, thermal or redox initiators described elsewhere herein.

The solvent and/or solvent mixtures used to co-deposit the initiator(s) and the polymer as a precoat may have the capacity to swell the substrate to various degrees. Typically, the co-deposition solvent swells the substrate (or at least the portion of the substrate to be imbibed with initiator) less than 900% by volume at room temperature and ambient pressure. For example, in one such embodiment, the co-deposition solvent swells the substrate (or at least the portion of the substrate to be imbibed with initiator) less than 100% by volume. By way of further example, in one such embodiment, the co-deposition solvent swells the substrate (or at least the portion of the substrate to be imbibed with initiator) less than 100% by volume. By way of further example, in one such embodiment, the co-deposition solvent swells the substrate (or at least the portion of the substrate to be imbibed with initiator) less than 25% by volume. In a preferred embodiment, the co-deposited layer is preferably washed using a solvent and/or solvent mixture, optionally with a solvent that swells that substrate, and optionally dried. Alternatively, the co-deposited layer is preferably washed using a solvent and/or solvent mixture, optionally with a solvent and/or solvent mixture that has limited swelling of the substrate, and optionally dried. Alternatively, the co-deposited layer is not washed using a solvent and optionally dried.

In one exemplary embodiment, a solution containing 1% to 5% (wt/wt) urethane can be prepared by dissolving the appropriate weight of urethane pellets in a suitable organic solvent, such as tetrahydrofuran, and diluting the solution with a second solvent, such as methanol. The final methanol concentration is preferably between 10%-90%, more preferably between 15%-85%, most preferably 60%. One or more suitable initiator molecules, such as benzoyl peroxide or dicumyl peroxide, are added to the polymer solution at a concentration typically from about 0.25% to about 10%. However, concentrations below 0.25% and above 10% can be used. Any desired substrate can be exposed to the polymer/initiator solution once or multiple times until a desired coating thickness and/or initiator surface concentration has been achieved. The solvent is typically removed, for example by evaporation, from the coated substrate between each exposure to the solution, in a case where the substrate is exposed multiple times. After the final exposure, the substrate is optionally allowed to sit for at least 10 minutes to allow any residual solvent to evaporate, prior to placing in a polymerization reaction mixture.

In another alternative method, the initiator(s) is/are incorporated into and/or onto the substrate by means of a aerosol deposition or spray coating process. The initiator(s) is/are mixed with a monosolvent, co-solvent, or mixed solvent system and applied to the substrate surface by means of a directed, charged or non-charged aerosol deposition method. For example, the initiator(s) is/are mixed with organic solvent mixture and deposited onto the substrate surface as an aerosol by means of a compressed air spray. The amount of initiator physio-adsorbed into and/or onto the surface of the substrate can be controlled by varying the amount of time the aerosol stays on the surface of substrate before the solvent evaporates and thus affecting the amount of initiator absorbed into the bulk of the substrate (e.g., the longer the dwell time on the surface the more initiator can move into the substrate bulk and visa versa). The dwell time of the aerosol on the substrate can be controlled by varying the boiling point of the aerosol which is done by varying the proportion of low and high boiling point solvents in the solvent system. Additionally, the amount of initiator applied onto and/or into the substrate can be controlled by varying the aerosol flow rate, aerosol gas mixture, aerosol droplet size, aerosol charge, substrate charge, aerosol deposition environment (temperature, pressure, and/or atmosphere), and the amount of aerosol applied. The aerosol deposition may be applied to any of the substrates described herein, including metals, ceramics, glasses, polymers, biological tissues, living or dead, woven and non-woven fibers, semi-metals such as silicon.

Regardless of the method of incorporation, initiator is incorporated into the substrate by imbibing the substrate or depositing a coating containing the initiator onto the substrate. The incorporated initiator may comprise one initiator species, or more than one initiator species. For example, one or more species of ultraviolet (UV) initiators, one or more species of thermal initiators, and/or one or more species of redox initiators may be incorporated into the substrate. More specifically, in one presently preferred embodiment, the initiator(s) are/is incorporated into the near-surface zone between its upper and lower boundaries as described elsewhere herein. Based upon experimental evidence to date, and without being bound to any particular theory, it appears that the incorporated initiator permits a grafting of the polymeric material from within the near-surface zone as well as the substrate surface.

Monomers can be selected such that their reactivity ratios give alternating copolymers, periodic copolymers with a pre-specified ratio of each monomer, random copolymers, block copolymers or homopolymers. Inclusion of more than two reactive groups on each monomer unit allows for the formation of star polymers, dendrimers, regularly branched polymers, randomly branched polymers, and brush polymers. In general, the monomer may be selected from any of the monomers disclosed herein. Thus, for example, the monomers may contain any of the pendant groups corresponding to Formulae ZI-1 to ZI-7. By way of further example, upon polymerization the monomers may provide the polymer with repeat units corresponding to any of Formula 1-12. In a preferred embodiment, the monomers are miscible with the polymerization mixture solvent system.

In processes for modification of the surface of a hydrophobic substrate, a hydrophilic solvent system preferably is employed. Aqueous solutions preferably are used as the solvent system, optionally containing ions or buffers, such as sodium, ammonium, potassium, chloride, phosphate, or acetate. In processes for modifying hydrophilic substrates, a hydrophobic solvent system preferably is used. In such processes, the preferred media is an organic solvent, typically a non-polar organic solvent, or a mixture thereof. Exemplary organic solvents include one or more of toluene, hexane, cyclohexane, benzene, xylene, tetrahydrofuran, and aliphatic alcohols. In a preferred embodiment, the solvent system does not swell the substrate (or at least that portion of the substrate from which the polymer will be grafted) by more than 25% by volume. For example, in one such embodiment, the solvent system does not swell the substrate (or at least that portion of the substrate from which the polymer will be grafted) by more than 10% by volume. In a preferred embodiment, the solvent system does not swell the substrate (or at least that portion of the substrate from which the polymer will be grafted) by more than 5% by volume. In one embodiment, the solvent system may even shrink the substrate (or at least that portion of the substrate from which the polymer will be grafted).

In one particularly preferred embodiment, the hydrophilic polymeric materials are grafted from the substrate by chain growth addition polymerization. The polymerization conditions described herein are generally mild compared to other methods of polymerization and thus do not significantly alter the mechanical properties, flexibility, or dimensional properties of the underlying substrate. In one preferred embodiment, for example, polymerization is carried out at a temperature not in excess of 60° C. The polymerization may be carried out over a relatively wide pH range, e.g., about 0-10. In one embodiment, the polymerization reaction is carried out at a pH of about 2-8. For example, when DCP and ferrous gluconate are used as redox pair, the polymerization reaction may be carried out at a pH of about 6-8. By way of further example, when benzoyl peroxide and ferrous gluconate are used as redox pair, the polymerization reaction may be carried out at a pH of about 4-6. By way of further example, when O,O-t-Butyl-O-(2-ethylhexyl) mono-peroxycarbonate ("TBEC") and ferrous gluconate are used as redox pair, the polymerization reaction may be carried out at a pH of about 5-7.

Examples of radical polymerization processes include, but are not limited to, UV, thermal, and redox initiated processes. In particular embodiments, the polymer is grafted from the substrate, by first incorporating one or more initiators, such as an ultraviolet (UV), thermal, or redox initiator into the substrate and initiating polymerization of one or more monomers from the surface. Preferably, the initiator is incorporated into the substrate by imbibing the substrate with initiator or coating the substrate with a layer, e.g., an undercoating layer (sometimes referred to herein as the co-deposited layer), comprising the initiator. The polymerization is typically initiated by exposing the initiator-imbibed substrate with a solution or suspension of the monomer or monomers to be polymerized. The quantity of polymer introduced to the substrate can be controlled by changing the concentration of the polymer in the solvent solution, surface tension of the polymer solution, polymerization temperature, pH of the polymer solution, polymerization solution agitation or flow conditions, by changing the amount of time the substrate is allowed to be in the polymer solution during one polymerization period, and/or by repeating any number of polymerization periods as required. When utilizing multiple polymerization periods, the polymer(s) used in the subsequent polymerization periods can be the same as, different from, or a mixture with the polymer(s) used in the previous polymerization period.

Chain transfer agents can be added to the monomer solution to mediate the graft-from radical polymerization reaction kinetics. Chain transfer agents include, but are not limited to, molecules containing halocarbons, thiols, dithiocarbamates, trithiocarbonates, dithioesters, xanthates, primary or secondary alcohols. Examples of chain transfer agents are bromotrichloromethane, 4-methylbenzenethiol, benzyl alcohol, methanol, ethanol, ethyleneglycol, glycerol, and isopropanol. In one embodiment the radical polymerization graftings are mediated using 2,2,6,6-tetramethylpiperidinie-1-oxyl (TEMPO). In one embodiment the radical polymerization graftings are mediated using reversible addition fragmentation transfer (RAFT) agents. Examples of RAFT agents include 2-(Dodecylthiocarbonothioylthio)-2-methylpropionic acid, 2-Cyano-2-propyl benzodithioate, 2-Cyano-2-propyl dodecyl trithiocarbonate, 4-Cyano-4-(phenylcarbonothioylthio)pentanoic acid, 4-Cyano-4-[(dodecylsulfanylthiocarbonyl)sulfanyl]pentanoic acid, Bis(dodecylsulfanylthiocarbonyl) disulfide, Bis(thiobenzoyl) disulfide, Cyanomethyl dodecyl trithiocarbonate, Cyanomethyl methyl(phenyl)carbamodithioate, and their analogues and derivatives In addition to monomer and a solvent system, the polymerization mixture may optionally contain a free radical inhibitor to encourage surface grafting. Without being bound to any particular theory, it is presently believed that the addition of a free radical inhibitor, including, hydroquinone, hydroquinone monomethyl ether, phenothiazine, 3,7-bis(dimethylamino)phenazathionium chloride, triethylene diamine, t-butylcatechol, butylated hydroxytoluene, and 4-t-butylphenol to the grafting solution decreases solution polymerization, thereby allowing more monomer to be available for grafting at or near the substrate surface/polymerization mixture interface.

Plasticizers can be incorporated into the grafted polymer at any time during and/or subsequent to surface polymerization. In the preferred embodiment, a hydrophilic plasticizer (such as citrated esters, ethylene glycol, propylene glycol, and/or polyethylene glycol [<2000 $M_w$]) is incorporated into the grafted polymer in a post-polymerization aqueous wash period.

i. UV Initiators

In one embodiment, the initiator is an ultraviolet (UV) initiator. The substrate and initiator are typically placed into an aqueous, degassed, solution containing a zwitterionic monomer and exposed to UV light, initiating the radical polymerization. In one exemplary embodiment, the UV light has a peak wavelength of 365 nm, generated by a 100 W UV.

Examples of UV radical initiators include, but are not limited to, 1-Hydroxycyclohexyl phenyl ketone, 2,2-Diethoxyacetophenone, 2-Benzyl-2-(dimethylamino)-4'-morpholinobutyrophenone, 2-Hydroxy-2-methylpropiophenone, 2-Hydroxy-4'-(2-hydroxyethoxy)-2-methylpropiophenone, 2-Methyl-4'-(methylthio)-2-morpholinopropiophenone, 3'-Hydroxyacetophenone, 4'-Ethoxyacetophenone, 4'-Hydroxyacetophenone, 4'-Phenoxyacetophenone, 4'-tert-Butyl-2',6'-dimethylacetophenone, Diphenyl(2,4,6-trimethylbenzoyl)phosphine oxide/2-hydroxy-2-methylpropiophenone, 2,2-Dimethoxy-2-phenylacetophenone, 4,4'-Dimethoxybenzoin, 4,4'-Dimethylbenzil, Benzoin ethyl ether, Benzoin isobutyl ether, Benzoin methyl ether, Benzoin, 2-Methylbenzophenone, 3,4-Dimethylbenzophenone, 3-Hydroxybenzophenone, 3-Methylbenzophenone, 4,4'-Bis(diethylamino)benzophenone, 4,4'-Dihydroxybenzophenone, 4,4'-Bis[2-(1-propenyl)phenoxy]benzophenone, 4-(Diethylamino)benzophenone, 4-Benzoylbiphenyl, 4-Hydroxybenzophenone, 4-Methylbenzophenone, Benzophenone-3,3',4,4'-tetracarboxylic dianhydride, Benzophenone, Methyl benzoylformate, Michler's ketone, Sulfoniums, iodiums, 2-(4-Methoxystyryl)-4,6-bis(trichloromethyl)-1,3,5-triazine, Diphenyliodonium p-toluenesulfonate, N-Hydroxy-5-norbornene-2,3-dicarboximide perfluoro-1-butanesulfonate, N-Hydroxynaphthalimide triflate, 2-tert-Butylanthraquinone, 9,10-Phenanthrenequinone, Anthraquinone-2-sulfonic acid sodium salt monohydrate, Camphorquinone, Diphenyl (2,4,6-trimethylbenzoyl)phosphine oxide, 10-Methylphenothiazine, thioxanthones, and IRGRCURE 2959.

ii. Thermal Initiators

In another embodiment a heat activated (thermal) initiator is used, in place of the UV initiator described above, and the graft-from polymerization is initiated by heating the aqueous monomer solution temperature to a desired temperature and holding the temperature constant until the desired degree of polymerization is achieved.

Suitable thermal initiators include, but are not limited to, tert-Amyl peroxybenzoate, 4,4-Azobis(4-cyanovaleric acid), 2,2'-Azobis[(2-carboxyethyl)-2-methylpropionamidine], 2,2'-Azobis(4-methoxy-2,3,-dimethylvaleronitrile), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy)cyclohexane, 2,5-Bis (tert-butylperoxy)-2,5-dimethylhexane, 2,5-Bis(tert-Butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, Cumene hydroperoxide, Cyclohexanone peroxide, Dicumyl peroxide, Lauroyl peroxide, 2,4-Pentanedione peroxide, Peracetic acid, Potassium persulfate.

The temperature to which the solution is heated is dependent, among other things, on the monomer and/or the initiator, and and/or the substrate. Examples of thermal radical initiators include, but are not limited to, azo-compounds such as azobisisobutyronitrile (AIBN) and 1,1'-Azobis(cyclohexanecarbonitrile) (ABCN). Preferable grafting temperatures are near the 10 hour T1/2 of the initiator selected. The graft-from radical polymerization reaction can be thermally quenched by heating beyond the initiators half life.

iii. Redox Initiators

In another embodiment, a redox initiator system is used to initiate polymerization from the surface of the substrate. The redox initiator system typically includes a pair of initiators: an oxidant and a reducing agent. The redox chemistry described herein can be modified to prepare hydrophilic polymeric materials, for example, such as zwitterionic polymeric materials. Redox initiation is regarded as a one-electron transfer reaction to effectively generate free radicals under mild conditions. Suitable oxidants include, but are not limited to, peroxide, hydroperoxide, persulfates, peroxycarbonates, peroxydisulfates, peroxydiphosphate, permanganate, salts of metals such as Mn(III), Ce(IV), V(V), Co(III), Cr(VI) and Fe(III).

Suitable reducing agents include, but are not limited to, metal salts such as Fe(II), Cr(II), V(II), Ti(III), Cu(II), and Ag(I) salts, and oxyacids of sulfur, hydroxyacids, alcohols, thiols, ketones, aldehydes, amine, and amides. For example, in some embodiments, the reducing agent is an iron(II) salt, such as iron(II) L-ascorbate, ferrous sulfate, iron(II) acetate, iron(II) acetylacetonate, iron(II) ethylenediammonium sulfate, iron(II) gluconate, iron(II) lactate, iron(II) oxalate, or iron(II) sulfate.

Polymerization can be initiated by radicals formed directly from the redox reaction and/or by macroradicals formed by the abstraction of a hydrogen atom from the substrate by the transient radicals formed during the redox reaction.

In one embodiment, the substrate is coated with a undercoating coating and the hydrophilic material is grafted from the undercoating layer by redox polymerization. The undercoating coating contains oxidants or reducing agents. In a preferred embodiment, the undercoating layer contains one or more reducing agents, such as acids, alcohol, thiols, ketones, aldehydes, amines and amides. An oxidant is used to react with one or more functional groups of the undercoating layer to form radicals which initiate the graft-from polymerization.

In a particular embodiment, the undercoating layer is a copolymer with pendant groups of aliphatic chains containing silanol and/or hydroxyl groups. Such materials can be used to form a undercoating layer on polymeric substrates, such as polyurethane (PU). An oxidant, such as a salt of Ce(IV), reacts with the hydroxyl group under mild conditions to form hydroxyl radicals in the undercoating layer to grow the zwitterionic polymers.

In still another embodiment, a pair of peroxides and metal salts (such as Fe(II) as used in the Fenton Reaction) is used in the redox polymerization to graft zwitterionic polymers from polymers such as polyurethane. Peroxides for use in the redox polymerization include diacyl peroxides, dialkyl peroxides, diperoxyketals, hydroperoxides, ketone peroxides, peroxydicarbonates, and peroxyesters. Exemplary diacyl peroxides include decanoyl peroxide, lauroyl peroxide, succinic acid peroxide, and benzoyl peroxide, Exemplary dialkyl peroxides include dicumyl peroxide, 2,5-di(t-butylperoxy)-2,5-dimethylhexane, t-butyl cumyl peroxide, a,a'-bis (t-butylperoxy)diisopropylbenzene mixture of isomers, di(t-amyl) peroxide, di(t-butyl) peroxide and 2,5-di(t- butylperoxy)-2,5-dimethyl-3-hexyne. Exemplary diperoxyketals include 1,1-di(t-butylperoxy)-3,3,5-trimethylcyclohexane, 1,1-di(t-butylperoxy)cyclohexane, 1,1-di(t-amylperoxy)cyclohexane, n-butyl 4,4-di(t-butylperoxy)valerate, ethyl 3,3-di-(t-amyl peroxy)butanoate and ethyl 3,3-di-(t-butylperoxy)butyrate. Exemplary hydroperoxides include cumene hydroperoxide and t-butyl hydroperoxide. Exemplary ketone peroxides include methyl ethyl ketone peroxide mixture and 2,4-pentanedione peroxide. Exemplary peroxydicarbonates include di(n-propyl)peroxydicarbonate, di(sec-butyl)peroxydicarbonate, and di(2-ethylhexyl)peroxydicarbonate. Exemplary peroxyesters include 3-hydroxy-1,1-dimethylbutyl peroxyneodecanoate alpha-cumyl peroxyneodecanoate, t-amyl peroxyneodecanoate, t-butyl peroxyneodecanoate, t-amyl peroxypivalate, t-butyl peroxypivalate, 2,5-di(2-ethylhexanoylperoxy)-2,5-dimethylhexane, t-amyl peroxy-2-ethylhexanoate, t-butyl peroxy-2-ethylhexanoate, t-amyl peroxyacetate, t-butyl peroxyacetate, t-butyl peroxyacetate, t-butyl peroxybenzoate, 00-(t-amyl)O-(2-ethylhexyl) monoperoxycarbonate, 00-(t-butyl)-O-isopropyl monoperoxycarbonate, 00-(t-butyl)-O-(2-ethyl hexyl) monoperoxycarbonate, polyether poly-t-butylperoxy carbonate, and t-butyl peroxy-3,5,5-trimethylhexanoate.

In some embodiments, any of the aforementioned peroxides such as benzoyl peroxide, lauroyl peroxide, hydrogen peroxide, or dicumyl peroxide can be imbibed into the polymer such as polyurethane by dipping the polymer into a peroxide solution in an organic solvent for a predetermined period of time and dried. The peroxide-containing polymer is put into a solution of monomer. The redox polymerization is initiated by the addition of a reducing agent, for example salts of Fe(II), such as Fe(II) chloride, Fe(II) sulfate, ammonium Fe(II) sulfate, or Fe(II) gluconate, at room temperature or elevated temperature, to the monomer solution.

In accordance with one suitable process, for example, a Fenton reaction is used to initiate the surface modification reaction. In one embodiment, oxidation by a mixture of an iron(II) species and hydrogen peroxide is performed under mild conditions, for example, room temperature, in an aqueous solution, and relatively low concentrations of hydrogen peroxide (e.g., less than in some commercially marketed contact lens cleaning solutions). The surface modification initiated by the Fenton reaction is fast and a simple, one-step reaction, and unlike other initiator systems, residual initiator is non-toxic and easily extracted as described elsewhere herein. In one particular embodiment, the iron(II) species is present in the reaction mixture at a concentraiotn of from about 0.1 mM to about 0.5 M (e.g., 0.5 mM, 10 mM, 25 mM, 50 mM, 100 mM, or 250 mM). In these and other embodiments, the peroxide (e.g., hydrogen peroxide) is present at a concentration of from about 0.05% to about 10% of the reaction mixture. Suitable solvents and solvent systems for the reaction mixture, as well as representative temperatures for carrying out the reaciton, are as described elsewhere herein.

For modifying the surface of a catheter component by graft polymerization, it has been found particularly useful to use hydrophobic-hydrophilic redox initiator pairs. For example, in one embodiment the hydrophobic member of a hydrophobic-hydrophilic redox initiator pair is incorporated into a hydrophobic substrate as previously described. The substrate surface is then treated with an aqueous polymerization mixture containing monomers, typically hydrophilic monomers, and the hydrophilic member of the redox pair. This method offers particular advantages when polymers are being grafted from components having exposed external and internal surfaces to be modified (such as catheters) and any substrate that cannot readily be exposed to light. Additionally, such a system tends to minimize the extent of non graft polymerization in the bulk polymerization mixture away from the polymerization mixture/substrate surface interface.

In a preferred embodiment, the hydrophilic-hydrophobic redox pair is a hydrophobic oxidizing agent/hydrophilic reducing agent pair wherein (i) the hydrophobic oxidizing agent is tert-amyl peroxybenzoate, O,O -t-Butyl-O-(2-ethylhexyl) mono-peroxycarbonate, benzoyl peroxide, 2,2-bis (tert-butylperoxy)butane, 1,1-bis(tert-butylperoxy)cyclohexane, 2,5-bis(tert-butylperoxy)-2,5-dimethylhexane, 2,5-Bis(tert-Butylperoxy)-2,5-dimethyl-3-hexyne, bis(1-(tert-butylperoxy)-1-methylethyl)benzene, 1,1-bis(tert-butylperoxy)-3,3,5-trimethylcyclohexane, tert-butyl hydroperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, 4,4-azobis(4-cyanovaleric acid), or 1,1'-Azobis(cyclohexanecarbonitrile), 2,2'-Azobisisobutyronitrile (AIBN) and (ii) the hydrophilic reducing agent is $Fe^{2+}$, $Cr^{2+}$, $V^{2+}$, $Ti^{3+}$, $Co^{2+}$, $Cu^+$, or an amine; transition metal ion complexes, e.g., copper (II) acetylacetonate, $HSO_3^-$, $SO_3^{2-}$, $S_2O_3^{2-}$, or $S_2O_5^2$. Exemplary combinations include any of the aforementioned peroxides and $Fe^{2+}$. In some preferred embodiments, benzoyl peroxide, dicumyl peroxide, or O,O-t-Butyl-O-(2-ethylhexyl) mono-peroxycarbonate are used in combination with $Fe^{2+}$.

In an alternative embodiment, the hydrophilic-hydrophobic redox pair is a hydrophilic oxidizing agent/hydrophobic reducing agent pair wherein (i) the hydrophilic oxidizing agent is peracetic acid, a persulfate such as potassium persulfate, $Fe^{3+}$, $ClO^{3-}$, $H_2O_2$, $Ce^{4+}$, $V^{5+}$, $Cr^{6+}$, or $Mn^{3+}$, or their combinations; and (ii) the hydrophobic reducing agent is an alcohol, carboxylic acid, amine, or a boronalkyl or their combinations.

In accordance with one suitable process, for example, potassium persulfate can be used to initiate the surface modification reaction, similar to the Fenton reaction protocol described above. Unlike many redox reactions which require a redox pair, potassium persulfate alone can efficiently initiate the one-step reaction in aqueous solution. In one particular embodiment, potassium persulfate is present in the reaction mixture at a concentraiotn of from about 0.1 mM to about 0.5 M (e.g., 0.5 mM, 10 mM, 25 mM, 50 mM, 100 mM, or 250 mM). Suitable solvents and solvent systems for the reaction mixture, as well as representative times and temperatures for carrying out the reaction, are as described elsewhere herein.

Other suitable redox systems include (1) organic-inorganic redox pairs, such as oxidation of an alcohol by $Ce^{4+}$, $V^{5+}$, $Cr^{6+}$, $Mn^{3+}$; (2) monomers which can act as a component of the redox pair, such as thiosulfate plus acrylamide, thiosulfate plus methacrylic acid, and N,N-dimethylaniline plus methyl methacrylate, and (3) boronalkyl-oxygen systems.

iv. Exemplary Initiators

Exemplary initiators include, but are not limited to, diacyl peroxides such as benzoyl peroxide, dichlorobenzoyl peroxide, dilauroyl peroxide, didecanoyl peroxide, diacetyl peroxide succinic acid peroxide, disuccinic peroxide and di(3,5,5-trimethylhexanoyl) peroxide. In a preferred embodiment, the diacyl peroxide is an aromatic diacyl peroxide, such as benzoyl peroxide.

Other exemplary initiators include, but are not limited to, peroxydicarbonates such as diethyl peroxydicarbonate, di-n-butyl peroxydicarbonate, diisobutyl peroxydicarbonate, di-4-tert-butylcyclohexyl peroxydicarbonate, di-sec-butyl peroxydicarbonate, di-2-ethylhexyl peroxydicarbonate, di-n-propyl peroxydicarbonate and diisopropyl peroxydicarbonate; peroxyesters, such as t-butyl perneodecanoate, t-butyl and t-amyl peroxy 2-ethylhexanoate, and t-butyl peroxybenzoate; monoperoxycarbonates based on t-butyl and t-amyl monoperoxy 2-ethylhexyl carbonates; persulfates, such as potassium persulfate, ammonium persulfate, and sodium persulfate; cumene hydroxide, tert-butyl hydroperoxide, di(tert-amyl) peroxide, tert-butyl peroxide, 2,5-Bis(tert-butylperoxy)-2,5-dimethylhexane, 1,1-Bis(tert-butylperoxy)-3,3,5-trimethylcyclohexane; 1,1-Bis(tert-amylperoxy)cyclohexane, 1,1-Bis(tert-butylperoxy)-3,3,5-trimethylcyclohexane, 1,1-Bis(tert-butylperoxy)cyclohexane, 2,2-Bis(tert-butylperoxy)butane, 2,4-Pentanedione peroxide, 2,5-Bis(tert-butylperoxy)-2,5-dimethylhexane, 2,5-Di(tert-butylperoxy)-2,5-dimethyl-3-hexyne, 2-Butanone peroxide, cumene hydroperoxide, di-tert-amyl peroxide, dicumyl peroxide, lauroyl peroxide, tert-butyl peracetate, tert-butyl peroxide, tert-butyl peroxybenzoate, tert-butylperoxy 2-ethylhexyl carbonate, tert-Butylperoxy isopropyl carbonate, 4-nitro-bezenecarboperoxoic acid t-butyl ester, cyclohexanone peroxide, [(methylperoxy)(diphenyl)methyl]benzene, bis(t-butylcyclohexyl)peroxydicarbonate, and 2, 4, 6-triphenylphenoxyl dimer.

For substrates requiring coating on both internal and external surfaces, additional considerations are required for initiating polymerization. Thermal initiators can be used; however, the elevated temperature typically required can adversely affect the substrate material. UV based approaches must be designed such that they can penetrate through the material or can be applied intraluminally, for instance from a fiber optic source threaded into the lumen. This may be achieved by selecting a photoactive initiator which is labile at a UV wavelength not absorbed by the substrate polymer. Generally, lower wavelength UV irradiation is less absorbed and penetrates more readily than higher wavelength UV.

In contrast, redox chemistries generally do not require a direct line of sight to a light source to initiate polymerization since polymerization is not initiated photolytically and therefore may be advantageous for coating substrates that have one or more surfaces that are difficult to expose to the UV source, such as catheter lumens. Further, redox polymerization typically can be done at low temperatures, for example less than 60° C., less than 55° C., less than 50° C., less than 45° C., less than 40° C., less than 35° C., or less than 30° C.

The graft-from polymerization can propagate through a cationic or anionic reaction, where the substrate surface acts as the cation or anion initiator or a cationic or anionic initiator is immobilized on the substrate and the monomer contains a reactive olefin. Examples of anionic polymerization are anionic ring opening, as in the case of synthesizing polycaprolactone or polycaprolactam, where the polymerization proceeds through a lactone or lactam moiety in a ring structure containing a pendant zwitterion group. Alternatively, an organic ring containing one or more units of unsaturation and a pendant zwitterionic group are polymerized. In one embodiment a pendant olefin is included in the monomer unit and is used for crosslinking, such as in ring opening metathesis polymerization (ROMP).

A particular challenge in modifying catheters is in delivering the reagents for modification to the lumens of the device without changing lumen dimensions or causing blockages in one of the lumens. Traditional graft-to approaches require a polymer to be created in solution and flowed into lumen for coating. Depending on the concentration of polymer, molecular weight, and solvent, the viscosity of this solution may be difficult to flow uniformly into a lumen. In some cases, the polymer may deposit in the lumen unevenly and even lead to lumen blockage. A preferred approach would be to deliver only small molecule reagents rather than pre-polymers or polymers in the polymerization reaction.

In a preferred embodiment, the hydrophilic polymer is created within or applied to the lumens of a device using a coating solution. In preferred embodiments, this coating solution is periodically or continuously exchanged with a larger reservoir or replaced with new solution. Periodically or continuously replacing this coating solution allows the levels of monomer or soluble initiator to be replenished. Further replacing the fluid in the lumens during the coating process allows free polymer formed in solution to be removed from the lumen during the reaction. Finally, exchanging this solution may also aid in temperature control inside the lumen. In some embodiments it is desired not to have a flow rate sufficient to damage the surface or to reduce conformality by having high shear.

In a preferred embodiment, the coating solution is flowed at a sufficient rate to displace the coating solution in the lumen at least once per hour. In a further preferred embodiment, the coating solution is flowed at a sufficient rate to achieve a residence time of the coating solution in the lumen of 30 minutes. In a further preferred embodiment, the coating solution is flowed at a sufficient rate to achieve a residence time of the coating solution in the lumen of 15 minutes. In a further preferred embodiment, the coating solution is flowed at a sufficient rate to achieve a residence time of the coating solution in the lumen of 10 minutes. In a further preferred embodiment, the coating solution is flowed at a sufficient rate to achieve a residence time of the coating solution in the lumen of 5 minutes. In a further preferred embodiment, the coating solution is flowed at a sufficient rate to achieve a residence time of the coating solution in the lumen of 1 minute. In a further preferred embodiment, the coating solution is flowed at a sufficient rate to achieve a residence time of the coating solution in the lumen of 30 seconds. In a further preferred embodiment, the coating solution is flowed at a sufficient rate to achieve a residence time of the coating solution in the lumen of 15 seconds.

In a preferred embodiment the coating solution is periodically replaced in the lumen of a catheter at discrete time points. In a preferred embodiment the coating solution is replaced in the lumen of a catheter at least every hour. In a preferred embodiment the coating solution is replaced in the lumen of a catheter at least every 30 minutes. In a preferred embodiment the coating solution is replaced in the lumen of a catheter at least every 15 minutes. In a preferred embodiment the coating solution is replaced in the lumen of a catheter at least every 10 minutes. In a preferred embodiment the coating solution is replaced in the lumen of a catheter at least every 5 minutes. In a preferred embodiment the coating solution is replaced in the lumen of a catheter at least every 1 minute. In a preferred embodiment the coating solution is replaced in the lumen of a catheter at least every 30 seconds. In a preferred embodiment the coating solution is replaced in the lumen of a catheter at least every 15 seconds.

In a preferred embodiment, the hydrophilic polymer is applied to the lumen of the device using a reaction mixture having a viscosity at the polymerization temperature of less than 30 cP. For example, in one embodiment the reaction mixture has a viscosity at the polymerization temperature of less than 25 cP. By way of further example, in one embodiment the reaction mixture has a viscosity at the polymerization temperature of less than 20 cP. By way of further example, in one embodiment the reaction mixture has a viscosity at the polymerization temperature of less than 15 cP. By way of further example, in one embodiment the reaction mixture has a viscosity at the polymerization temperature of less than 10 cP. By way of further example, in one embodiment the reaction mixture has a viscosity at the polymerization temperature of less than 7.5 cP. By way of further example, in one embodiment the reaction mixture has a viscosity at the polymerization temperature of less than 5 cP. By way of further example, in one embodiment the reaction mixture has a viscosity at the polymerization temperature of less than 4 cP. By way of further example, in one embodiment the reaction mixture has a viscosity at the polymerization temperature of less than 3 cP. By way of further example, in one embodiment the reaction mixture has a viscosity at the polymerization temperature of less than 2.5 cP. By way of further example, in one embodiment the reaction mixture has a viscosity at the polymerization temperature of less than 2 cP. By way of further example, in one embodiment the reaction mixture has a viscosity at the polymerization temperature of less than 1.5 cP. By way of further example, in one embodiment the reaction mixture has a viscosity at the polymerization temperature of less than 1 cP. In general, the polymerization reaction will be carried out a temperature in the range of 20-80° C. More typically, and in certain embodiments, the polymerization reaction will be carried out a temperature less than about 60° C. Depending upon the materials of construction, the size of the catheter, solvents and other reaction conditions, the polymerization reaction may be carried out at a temperature in the range of about 30 to 50° C.

Having a high hydrophilic fouling polymer concentration in the coating solution may create uneven deposition of coating in the lumen or may require extensive washing to remove hydrophilic polymer that is not tightly bound. Delivering a coating solution initially containing only monomers and initiators may be preferred to delivering a solution containing high polymer concentrations. In a preferred embodiment, the hydrophilic polymer concentration in the coating solution is less than 5 mg/ml. In a preferred embodiment, the hydrophilic polymer concentration in the coating solution is less than 2.5 mg/ml. In a preferred embodiment, the hydrophilic polymer concentration in the coating solution is less than 1 mg/ml. In a preferred embodiment, the hydrophilic polymer concentration in the coating solution is less than 0.5 mg/ml. In a preferred embodiment, the hydrophilic polymer concentration in the coating solution is less than 0.25 mg/ml. In a preferred embodiment, the hydrophilic polymer concentration in the coating solution is less than 0.1 mg/ml. In a preferred embodiment, the hydrophilic polymer concentration in the coating solution is less than 0.05 mg/ml. In a preferred embodiment, the hydrophilic polymer concentration in the coating solution is less than 0.01 mg/ml. The polymer concentrations may be measured by separations and analysis techniques including HPLC.

In a preferred embodiment, imbibing conditions for an initiator are sufficient to create a hydrophilic layer on multiple materials of a medical device when a common reaction solution is used for polymerizing a hydrophilic layer.

As a result of the imbibing process, multiple components imbibed under the same conditions may contain about 0.001% by weight initiator. In some embodiments, multiple components imbibed under the same conditions will contain greater amounts of initiator, e.g., at least about 0.01% by weight. For example, in some embodiments multiple components imbibed under the same conditions will contain at least about 0.1% by weight. By way of further example, in some embodiments multiple components imbibed under the same conditions will contain about 0.05% to about 2% by weight initiator. By way of further example, in some embodiments multiple components imbibed under the same conditions will contain about 0.1% to about 1% by weight initiator. By way of further example, in some embodiments multiple components imbibed under the same conditions will contain about 0.2% to about 0.5% by weight initiator. By way of further example, in some embodiments multiple components imbibed under the same conditions will contain about 1% to about 10% by weight initiator. Typically, however, multiple components imbibed under the same conditions will contain less than about 20% by weight initiator. In each of these embodiments, the initiator is preferably one of the UV, thermal or redox initiators described elsewhere herein.

The solvent used to imbibe multiple components of the catheter with initiator may have the capacity to swell multiple components of the catheter (or at least the portion of those components to be imbibed with initiator) to various degrees. Typically, the imbibing solvent has a capacity to swell multiple components of the catheter (or at least the portion of those components to be imbibed with initiator) less than 900% by volume at room temperature and ambient pressure. For example, in one such embodiment, the imbibing solvent has a capacity to swell multiple components of the catheter (or at least the portion of those components to be imbibed with initiator) less than 750% by volume. By way of further example, in one such embodiment, the imbibing solvent has a capacity to swell multiple components of the catheter (or at least the portion of those components to be imbibed with initiator) less than 500% by volume. By way of further example, in one such embodiment, the imbibing solvent has a capacity to swell multiple components of the catheter (or at least the portion of those components to be imbibed with initiator) less than 250% by volume. By way of further example, in one such embodiment, the imbibing solvent has a capacity to swell multiple components of the catheter (or at least the portion of those components to be imbibed with initiator) less than 100% by volume. By way of further example, in one such embodiment, the imbibing solvent has a capacity to swell multiple components of the catheter (or at least the portion of those components to be imbibed with initiator) less than 100% by volume. By way of further example, in one such embodiment, the imbibing solvent has a capacity to swell multiple components of the catheter (or at least the portion of those components to be imbibed with initiator) less than 25% by volume.

Preferably, the two or more catheter components are not significantly swelled by the polymerization mixture (e.g., by the polymerization mixture solvent system, the polymerization monomers, or both) and the initiator(s) incorporated into the substrates has/have limited solubility in the solvent system.

In a preferred embodiment, two or more catheter components from which the hydrophilic polymer will be grafted will not swell more than 30% by volume at 25° C. under equilibrium conditions in the polymerization mixture solvent system. In certain embodiments, two or more catheter components from which the hydrophilic polymer will be grafted will not swell more than 15% by volume at 25° C. under equilibrium conditions in the polymerization mixture solvent system. In certain embodiments, two or more catheter components from which the hydrophilic polymer will be grafted will not swell more than 5% by volume at 25° C. under equilibrium conditions in the polymerization mixture solvent system. In certain embodiments, the two or more catheter components from which the hydrophilic polymer will be grafted will not swell or may even shrink at 25° C. under equilibrium conditions in the polymerization mixture solvent system. As previously noted, the component substrate may be a composite of materials. In such instances, it is preferred that the near-surface region of the substrate into which the polymerization initiator is incorporated satisfy the swelling criteria recited herein. For example, in those embodiments in which the substrate comprises a coating of a precoat material overlying a metal, ceramic, glass or semi-metallic material, it is preferred that the coating of the precoat material not swell more than 30% by volume at 25° C. under equilibrium conditions in the polymerization mixture solvent system.

As described elsewhere herein, the initiator may comprise a redox pair; in such embodiments, at least one member of such pair have such a limited solubility in the polymerization mixture solvent system. In one embodiment, the redox pair comprises a peroxide and a reducing agent wherein the peroxide has limited solubility in the polymerization solvent system and the reducing agent has high solubility in the polymerization solvent system. By way of further example, in certain embodiments, the peroxide has a log P partition coefficient greater than or equal to 3 for two or more hydrophobic components and a log P partition coefficient less than 3 for hydrophilic substrates and phases. By way of further example, in certain embodiments, the peroxide has a log P partition coefficient greater than or equal to 5 for two or more hydrophobic components and a log P partition coefficient less than 1 for hydrophilic substrates and phases. By way of further example, in certain embodiments, the peroxide has a log P partition coefficient greater than or equal to 7 for two or more hydrophobic components and a log P partition coefficient less than −1 for hydrophilic substrates and phases. By way of further example, in certain embodiments, the peroxide has a log P partition coefficient greater than or equal to 9 for two or more hydrophobic components and a log P partition coefficient less than −3 for hydrophilic substrates and phases.

Having described the invention in detail, it will be apparent that modifications and variations are possible without departing from the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Surface Modification of PICC Catheter

PICC catheters comprising polyurethane (Tecothane®)-30% $BaSO_4$-5FR DD lumen catheter bodies, polyurethane (Pellethane®) junction hubs, and polyurethane (Pellethane®) extension lines were surface modified. The lumens of the PICC body had an aspect ratio of approximately 500:1. First, the entire catheter was imbibed with O,O-t-Butyl-O-(2-ethylhexyl) mono-peroxycarbonate ("TBEC"). Next the catheters were modified with SBMA monomer and Fe(II) reaction solution. The imbibing and reaction solutions were flowed through the lumen of the catheter using a pumping system. The modified samples were washed and dried. In this example, SBMA was the only monomer introduced during the polymerization reaction.

Example 2

Surface Modification of PICC Catheter—Body Lumen

Three PICC catheters modified in Example 1 were cut into 11 sections spaced along the axial length of the body. Data from the corresponding segments from each of the three were averaged. The hydrophilic surface modification had an Average Dry Thickness across the axial length of the PICC body of >200 nm on the luminal wall, exterior, and septum. The hydrophilic surface modification had a Standard Deviation of Thickness across the axial length of the PICC body of <25% of the Average Dry Thickness of the corresponding surface for the luminal wall, exterior, and septum.

Example 3

Surface Modification of PICC Catheter—Midpoint Region of Body Lumen

Three PICC catheters modified in Example 1 were cut into 11 sections spaced along the axial length of the body. Data from the corresponding segment from each of the three were averaged. The hydrophilic surface modification had a Dry Thickness at the Midpoint Region of the body luminal wall of >200 nm. The Dry Thickness at the Midpoint Region of the body lumen was >80% of the Average Dry Thickness across the axial length of the body lumen.

Example 4

Surface Modification of PICC Catheter—Body Conformality

PICC bodies modified as in example 1 were examined by confocal laser profilometry under conditions that distinguish modified from unmodified regions of the surface. The luminal wall of the catheter body was found to be conformal at a level of 0.01 $mm^2$.

Example 5

Surface Modification of PICC Catheter—Extension Lines

Seventeen PICC catheters were modified as in Example 1 and the extension lines were cut open to expose the lumen walls for IR analysis. Data from the corresponding segment from each of the seventeen were averaged. The hydrophilic surface modification had an Average Dry Thickness across the axial length of the extension line of >200 nm on the luminal wall and exterior. Further, the hydrophilic surface modification had an Average Dry Thickness of >200 nm on the exterior wall of the extension lines, luminal wall of the extension lines, exterior wall of the catheter body, luminal wall of the catheter body, and septum of the catheter body. Additionally, the hydrophilic surface modification had an Average Dry Thickness of <1000 nm on the luminal wall of the extension lines, luminal wall of the catheter body, and septum of the catheter body.

Example 6

Surface Modification of PICC Catheter—Uniformity of Extension Lines

Seventeen PICC catheters were modified as in Example 1 and the extension lines were cut open to expose the lumen walls for IR analysis. Data from the corresponding segment from each of the seventeen were averaged. The hydrophilic surface modification had a Standard Deviation of Thickness across the axial length of the extension line of <25% of the Average Dry Thickness of the corresponding surface for the luminal wallor exterior.

Example 7

Surface Modification of PICC Catheter—Extension Lines Conformality

PICC extension line lumens modified in example 1 were examined by confocal laser profilometry under conditions that distinguish modified from unmodified regions of the surface. The luminal surface of the extension line was found to be conformal at a level of 0.01 mm$^2$.

Example 8

Surface Modification of PICC Catheter—Junction Hub

A PICC catheter was modified as in Example 1 and the junction hub was cut open to expose the lumen walls for IR analysis. The hydrophilic surface modification had an Average Dry Thickness on the lumen of the junction hub of >200 nm. Catheters made in the same process also had an Average Dry Thickness on the luminal surface of the catheter body and in the extension line of >200 nm.

Example 9

Mechanical and Dimensional Impact of Process on A PICC Catheter

The PICC catheters modified in Example 1 were assessed for mechanical properties relative to the unmodified device using an Instron tester to measure the break strength of individual catheter components or across junctions of two components. The Modified PICCs did not show a decrease in catheter body break force, catheter body elongation before breakage, extension line break force, body/juncture hub break force, extension line/juncture hub break force, or extension line/luer hub break force relative to the unmodified PICC.

Example 10

Surface Modification of Martech® Hemodialsyis Catheter

Martech® 14.5FRX55 cm MOREFLOW CARBO-BLUE catheters were surface modified. First, entire catheters were imbibed with Dicumyl Peroxide ("DCP"). Next the catheters were statically modified with SBMA monomer and Fe(II) reaction solution. The modified samples were washed and dried.

Example 11

Surface Modification of Martech® Hemodialsyis Catheter

Martech® 14.5FRX55 cm MOREFLOW CARBO-BLUE catheters were surface modified. First, entire catheters were imbibed with O,O-t-Butyl-O-(2-ethylhexyl) mono-peroxycarbonate ("TBEC"). Next the catheters were statically modified with SBMA monomer and Fe(II) reaction solution. The modified samples were washed and dried.

Example 12

Surface Modification of Martech® Catheter-Uniformity of Tip

The tips of the Martech® catheters modified in Example 10 were cut from the axial length of the body. The hydrophilic surface modification was found to be conformal at a level of 0.01 mm$^2$ through twenty two images captured by scanning electron microscopy.

Example 13

Surface Modification of Martech® Catheter-Uniformity of Tip

The tips of the Martech® catheters modified in Example 10 were cut from the axial length of the body. The hydrophilic surface modification was found to be conformal at a level of 0.01 mm$^2$ through twenty two images captured by scanning electron microscopy.

Example 14

Surface Modification of Martech® Catheter-Thickness of Tip(MWS1-2492)

The tips of the Martech® catheters modified in Example 10 were cut from the axial length of the body. The hydrophilic polymer surface had a Dry Thickness of approximately 3 μm.

Example 15

Addition of *Eucalyptus* Oil to an Antimicrobial Catheter Modified with a Hydrophilic Surface A catheter body comprising chlorhexidine is modified as in Example 1 and is placed in a solution of 1-10% *Eucalyptus* oil in isopropyl alcohol at 37° C. for 2 hours.

What is claimed is:

1. A method of inhibiting microbial contamination in a catheter, the method comprising the step of:
   infusing a lumen of the catheter with a hydrochloric acid solution having a concentration of 0.3 Molar to 1.0 Molar.

2. The method according to claim 1, wherein the hydrochloric acid solution has a hydrochloric acid concentration of 0.3 Molar to 0.5 Molar.

3. The method according to claim 1, further comprising the step of:
   allowing the hydrochloric acid solution to dwell within the lumen for about an hour.

4. The method according to claim 3, further comprising the step of:
   drawing the hydrochloric acid solution from the lumen following the hour dwell time.

5. The method according to claim 4, further comprising the step of:
   flushing the catheter with a saline solution following the withdrawal of the hydrochloric acid solution.

6. The method according to claim 1, wherein the hydrochloric acid solution further includes an antimicrobial agent.

7. The method according to claim 6, wherein the antimicrobial agent includes silver sulfadiazine.

8. The method according to claim 7, wherein the silver sulfadiazine is eluted from the catheter and configured to provide a concentration of at least 128 ppm of the silver sulfadiazine adjacent to a surface of the catheter.

9. The method according to claim 6, wherein the antimicrobial agent includes Rifampin and Minocycline.

10. The method according to claim 1, wherein the hydrochloric acid solution further includes an anti-coagulant.

11. The method according to claim 10, wherein the anti-coagulant is heparin.

12. A method of treating a patient having a microbial contamination of an indwelling catheter, the method comprising the steps of:
    infusing a lumen of the catheter with a hydrochloric acid solution having a concentration of 0.3 Molar to 1.0 Molar.

13. The method according to claim 12, wherein the hydrochloric acid solution has a hydrochloric acid concentration of 0.3 Molar to 0.5 Molar.

14. The method according to claim 12, further comprising the step of:
    selecting a hydrochloric acid concentration of 0.4 Molar to 1.0 Molar in response to a biofilm of microbial contamination being present in the catheter.

15. The method according to claim 12, further comprising the step of:
    allowing the hydrochloric acid solution to dwell within the lumen for about 30 minutes.

16. The method according to claim 15, further comprising the step of:
    drawing the hydrochloric acid solution from the lumen following the hour dwell time.

17. The method according to claim 16, further comprising the step of:
    flushing the catheter with a saline solution following the withdrawal of the hydrochloric acid solution.

18. The method according to claim 12, wherein the hydrochloric acid solution further includes an antimicrobial agent.

19. The method according to claim 18, wherein the antimicrobial agent includes silver sulfadiazine.

20. The method according to claim 19, wherein the silver sulfadiazine is eluted from the catheter and configured to provide a concentration of at least 128 ppm of the silver sulfadiazine adjacent to a surface of the catheter.

21. The method according to claim 18, wherein the antimicrobial agent includes Rifampin and Minocycline.

22. The method according to claim 12, wherein the hydrochloric acid solution further includes an anti-coagulant.

23. The method according to claim 22, wherein the anti-coagulant is heparin.

* * * * *

Disclaimer

9,694,114 B2 — David Lucchino, Charlestown, MA (US); Christopher R. Loose, Cambridge, MA (US). ANTIMICROBIAL CATHETERS WITH PERMEABILIZATION AGENTS. Patent dated July 4, 2017. Disclaimer filed June 8, 2020, by the assignee, Arrow International, Inc.

Hereby disclaim complete entire claims 1-23 of said patent.

*(Official Gazette, July 21, 2020)*